(12) United States Patent
Dobak, III

(10) Patent No.: US 9,844,520 B2
(45) Date of Patent: Dec. 19, 2017

(54) REDUCTION OF ADIPOSE TISSUE

(71) Applicant: John Daniel Dobak, III, La Jolla, CA (US)

(72) Inventor: John Daniel Dobak, III, La Jolla, CA (US)

(*) Notice: Subject to any disclaimer, the term of this patent is extended or adjusted under 35 U.S.C. 154(b) by 0 days.

(21) Appl. No.: 15/133,079

(22) Filed: Apr. 19, 2016

(65) Prior Publication Data

US 2016/0310444 A1 Oct. 27, 2016

Related U.S. Application Data

(62) Division of application No. 14/796,686, filed on Jul. 10, 2015, now Pat. No. 9,351,945.

(60) Provisional application No. 62/165,716, filed on May 22, 2015, provisional application No. 62/121,927, filed on Feb. 27, 2015.

(51) Int. Cl.
*A61K 31/08* (2006.01)
*A61K 47/10* (2017.01)
*A61K 9/00* (2006.01)

(52) U.S. Cl.
CPC ............ *A61K 31/08* (2013.01); *A61K 9/0019* (2013.01); *A61K 47/10* (2013.01)

(58) Field of Classification Search
CPC ...................................................... A61K 31/08
See application file for complete search history.

(56) References Cited

U.S. PATENT DOCUMENTS

| | | |
|---|---|---|
| 5,614,178 A | 3/1997 | Bloom et al. |
| 5,681,552 A | 10/1997 | Shevade et al. |
| 5,756,119 A | 5/1998 | Deckner et al. |
| 5,874,095 A | 2/1999 | Deckner et al. |
| 6,572,873 B1 | 6/2003 | Osman et al. |
| 6,846,412 B2 | 1/2005 | Hogan et al. |
| 6,942,165 B1 | 9/2005 | Osman et al. |
| RE38,919 E | 12/2005 | Garrido et al. |
| 7,025,290 B2 | 4/2006 | Osman et al. |
| 7,026,360 B1 | 4/2006 | Festo |
| 7,166,570 B2 | 1/2007 | Hunter et al. |
| 7,357,336 B2 | 4/2008 | Osman et al. |
| RE40,640 E | 2/2009 | Garrido et al. |
| 7,494,488 B2 | 2/2009 | Weber |
| 7,604,185 B2 | 10/2009 | Osman et al. |
| 7,622,130 B2 | 11/2009 | Kolodney et al. |
| 7,727,537 B2 | 6/2010 | Modi |
| 7,731,986 B2 | 6/2010 | Wright et al. |
| 7,754,230 B2 | 7/2010 | Kolodney et al. |
| 7,814,943 B2 | 10/2010 | Harman et al. |
| 7,842,282 B2 | 11/2010 | Harman et al. |
| 7,842,283 B2 | 11/2010 | Harman et al. |
| 7,902,387 B2 | 3/2011 | Prasad et al. |
| 7,994,351 B2 | 8/2011 | Prasad et al. |
| 8,101,593 B2 | 1/2012 | Hodge et al. |
| 8,122,917 B2 | 2/2012 | Harman et al. |
| 8,242,294 B2 | 8/2012 | Moriarty et al. |
| 8,298,556 B2 | 10/2012 | Kolodney et al. |
| 8,323,677 B2 | 12/2012 | Wright et al. |
| 8,362,285 B2 | 1/2013 | Prasad et al. |
| 8,367,649 B2 | 2/2013 | Hodge et al. |
| 8,367,852 B2 | 2/2013 | Prasad et al. |
| 8,734,833 B2 | 5/2014 | Wright et al. |
| 8,808,716 B2 | 8/2014 | Loupenok |
| 8,846,066 B2 | 9/2014 | Kolodney et al. |
| 9,351,945 B1 | 5/2016 | Dobak |
| 2003/0147928 A1 | 8/2003 | Zelle et al. |
| 2003/0216364 A1 | 11/2003 | Johnson |
| 2005/0089555 A1 | 4/2005 | Boderke et al. |
| 2005/0106544 A1 | 5/2005 | Joshi et al. |
| 2005/0143347 A1 | 6/2005 | Boderke et al. |
| 2005/0238705 A1 | 10/2005 | Hu et al. |
| 2005/0255149 A1 | 11/2005 | Narui et al. |
| 2006/0110448 A1 | 5/2006 | Grassberger et al. |
| 2006/0127468 A1 | 6/2006 | Kolodney et al. |
| 2006/0154906 A1 | 7/2006 | Kolodney et al. |
| 2006/0190299 A1 | 8/2006 | Joshi et al. |
| 2006/0264515 A1* | 11/2006 | Dejovin .................. A61K 31/00 514/649 |
| 2008/0069779 A1 | 3/2008 | Tamarkin et al. |
| 2008/0187595 A1 | 8/2008 | Jordan et al. |
| 2008/0193541 A1 | 8/2008 | Mentrup et al. |
| 2008/0206155 A1 | 8/2008 | Tamarkin et al. |
| 2008/0268055 A1 | 10/2008 | Mentrup et al. |
| 2008/0286349 A1 | 11/2008 | Nomoto et al. |
| 2008/0294072 A1 | 11/2008 | Crutchfield, III |
| 2009/0202467 A1 | 8/2009 | Bock |

(Continued)

FOREIGN PATENT DOCUMENTS

| | | | |
|---|---|---|---|
| CA | 2741334 A1 | 4/2010 | |
| CH | WO 2006133876 A1 * | 12/2006 | ........... A61K 8/4953 |
| EP | 1748780 A1 | 2/2007 | |
| EP | 1758590 A1 | 3/2007 | |
| EP | 1845938 A1 | 10/2007 | |
| EP | 1946746 A1 | 7/2008 | |
| EP | 1970051 A1 | 9/2008 | |
| EP | 2369956 A1 | 10/2011 | |
| EP | 2380576 A2 | 10/2011 | |
| EP | 2422789 A1 | 2/2012 | |

(Continued)

OTHER PUBLICATIONS

"Alcohols." (c) 2016. Available from: < http://goldbook.iupac.org/A00204.html >.*
Rowe, R.C., et al. "Handbook of Pharmaceutical Excipients." 6th ed. (c) 2009. pp. i-888.*
Human Prescription Drug Label for ASCLERA—polidocanol injection, solution; Updated Jul., 2014; Accessed from:; http://dailymed.nlm nih.gov/dailymed/drugInfo.cfm?setid=90550274-6605-44de-8c25-c5591080270f on Sep. 30, 2014.

(Continued)

*Primary Examiner* — Noble E Jarrell
*Assistant Examiner* — John S Kenyon
(74) *Attorney, Agent, or Firm* — Mintz, Levin, Cohn, Ferris, Glovsky and Popeo, PC

(57) ABSTRACT

Described herein, inter alia, are compositions, formulations, methods, and systems for reducing regional fat deposits and treating fat-related conditions.

9 Claims, 14 Drawing Sheets

(56) References Cited

U.S. PATENT DOCUMENTS

| | | |
|---|---|---|
| 2009/0214657 A1 | 8/2009 | Qazi et al. |
| 2010/0011890 A1 | 1/2010 | Tseng |
| 2010/0062067 A1 | 3/2010 | Tonge et al. |
| 2010/0098766 A1 | 4/2010 | Mentrup et al. |
| 2010/0137747 A1 | 6/2010 | Thomas et al. |
| 2010/0144890 A1 | 6/2010 | Boderke et al. |
| 2010/0166681 A1 | 7/2010 | Franke |
| 2010/0292650 A1 | 11/2010 | Kolodney et al. |
| 2011/0002896 A1 | 1/2011 | Kolodney et al. |
| 2012/0009285 A1 | 1/2012 | Wei et al. |
| 2012/0016347 A1 | 1/2012 | Shipp et al. |
| 2012/0141531 A1 | 6/2012 | Coulter et al. |
| 2012/0283328 A1 | 11/2012 | Modi |
| 2012/0329765 A1 | 12/2012 | Boderke et al. |
| 2013/0143869 A1 | 6/2013 | Kiehm et al. |
| 2013/0190282 A1 | 7/2013 | Hodge et al. |
| 2013/0190517 A1 | 7/2013 | Prasad et al. |
| 2013/0267721 A1 | 10/2013 | Prasad et al. |
| 2013/0331332 A1 | 12/2013 | Barg et al. |
| 2014/0004206 A1 | 1/2014 | Kolodney et al. |
| 2014/0155364 A1 | 6/2014 | Hodge et al. |
| 2014/0276384 A1 | 9/2014 | Schwab et al. |

FOREIGN PATENT DOCUMENTS

| | | |
|---|---|---|
| EP | 2550968 A1 | 1/2013 |
| EP | 2572718 A1 | 3/2013 |
| WO | WO-98/12228 A1 | 3/1998 |
| WO | WO-2005/041919 | 5/2005 |
| WO | WO-2008/067060 A2 | 6/2008 |
| WO | WO-2008/067060 A3 | 6/2008 |
| WO | WO-2008/067060 A8 | 6/2008 |
| WO | WO-2008/113421 A1 | 9/2008 |
| WO | WO-2010/048409 A1 | 4/2010 |
| WO | WO-2013/079211 A1 | 6/2013 |
| WO | WO-2016/138136 A1 | 9/2016 |

OTHER PUBLICATIONS

INEOS Oxide (lauryl Alcohol Ethoxylates, http://www.ineos.com/Show-Document/?Grade=Alkyr/020Ether)/020AE7&BU=INEOS°/0200xide&DocumentType=Technic ar/020Date/020Sheet, obtained from internet Mar. 19, 2015).

International Search Report dated May 3, 2016, for PCT Application No. PCT/US2016/19366, filed on Feb. 24, 2016, 2 pages.

Scientific Committee on Consumer Products (Opinion on polidocanol, SCCP 13th plenary meeting, published Oct. 2, 2007).

Olson, S. "Weight Loss Drug Destroys Fat, Thanks to Bladder Medication: Finally a Treatment for Obesity?" © 2014. Available from: < http://www.medicaldaily.com/weight-loss-drug-destroys-fat-thanks-bladder-medication-finally-treatment-obesity-316452 >.

National Library of Medicine—PubMed Health. "Polidocanol (injection)." (c)Jan. 19, 2014. Available from: <http://web.archive.org/web/20140119010808/http://www.ncbi.nlm.nih.gov/pubmedhealth/PMH T0011772>.

Written Opinion dated May 3, 2016, for PCT Application No. PCT/US2016/19366, filed on Feb. 24, 2016, 5 pages.

* cited by examiner

Inguinal crease enhancement

Group 2A, ID 321
Left: Placebo
Right: Polidocanol (1.25%)

Group 3B, ID 319
Left: Placebo
Right: Polidocanol (2%)

Moderate skin necrosis 1 of 9 animals
(11%)

2 of 9 animals
(22%)

Group 4, ID 311
Left: Placebo
Right: Deoxycholate (1%)

Severe skin necrosis 3 of 5 animals
(60%)

FIG. 9A

| Sample | Lot | Condition | T0 | 1M | 2M |
|---|---|---|---|---|---|
| Polidocanol 0.5% | CPR7482p17_0.5% | (-)20C | clear colorless | clear colorless | clear colorless |
| | | 25C | | clear colorless | clear colorless |
| | | 60C | | clear colorless | clear colorless |
| Polidocanol 1.25% | CPR7482p18_1.25% | (-)20C | clear colorless | clear colorless | clear colorless |
| | | 25C | | clear colorless | clear colorless |
| | | 60C | | clear colorless | clear colorless |
| Polidocanol 2% | CPR7482p19_2% | (-)20C | clear colorless | clear colorless | clear colorless |
| | | 25C | | clear colorless | clear colorless |
| | | 60C | | clear colorless | clear colorless |
| Placebo | CPR7482p20_0% | (-)20C | clear colorless | clear colorless | clear colorless |
| | | 25C | | clear colorless | clear colorless |
| | | 60C | | clear colorless | clear colorless |

FIG. 9B

| Sample | Lot | Condition | T0 | 1M | 2M |
|---|---|---|---|---|---|
| Polidocanol 0.5% | CPR7482p17_0.5% | (-)20C | 7.34 | 7.36 | 7.33 |
| | | 25C | | 7.35 | 7.35 |
| | | 60C | | 6.79 | 6.76 |
| Polidocanol 1.25% | CPR7482p18_1.25% | (-)20C | 7.32 | 7.33 | 7.33 |
| | | 25C | | 7.33 | 7.19 |
| | | 60C | | 6.78 | 6.68 |
| Polidocanol 2% | CPR7482p19_2% | (-)20C | 7.34 | 7.34 | 7.35 |
| | | 25C | | 7.33 | 7.06 |
| | | 60C | | 6.72 | 6.66 |
| Placebo | CPR7482p20_0% | (-)20C | 7.35 | 7.36 | 7.45 |
| | | 25C | | 7.36 | 7.36 |
| | | 60C | | 7.35 | 7.29 |

FIG. 9C

| Sample | Lot | Condition | T0 | 1M | 2M |
|---|---|---|---|---|---|
| Polidocanol 0.5% | CPR7482p17_0.5% | (-)20C | 342 | 359 | 353 |
| | | 25C | | 345 | 347 |
| | | 60C | | 368 | 362 |
| Polidocanol 1.25% | CPR7482p18_1.25% | (-)20C | 354 | 349 | 355 |
| | | 25C | | 356 | 356 |
| | | 60C | | 367 | 391 |
| Polidocanol 2% | CPR7482p19_2% | (-)20C | 358 | 354 | 354 |
| | | 25C | | 357 | 364 |
| | | 60C | | 368 | 366 |
| Placebo | CPR7482p20_0% | (-)20C | 339 | 343 | 340 |
| | | 25C | | 341 | 342 |
| | | 60C | | 343 | 350 |

FIG. 10

| Lot# | Sample Polidocanol conc | Condition | AUC | Calculated conc., mg/mL |
|---|---|---|---|---|
| CPR7482p20_0% | 0.0 | (-)20C | 0 | 0.0 |
| | | 25C | 0 | 0.0 |
| | | 60C | 0 | 0.0 |
| CPR7482p17_0.5% | 5.0 | (-)20C | 437,139,117 | 4.9 |
| | | 25C | 427,881,089 | 4.8 |
| | | 60C | 343,617,169 | 3.8 |
| CPR7482p18_1.25% | 12.5 | (-)20C | 769,665,182 | 11.9 |
| | | 25C | 742,836,530 | 11.4 |
| | | 60C | 707,180,250 | 10.9 |
| CPR7482p19_2% | 20.0 | (-)20C | 1,007,786,002 | 19.3 |
| | | 25C | 971,513,399 | 18.6 |
| | | 60C | 969,361,213 | 18.5 |

FIG. 11A

| Name | 0.5% (-20C) | 0.5% (25C) | 0.5% 60C |
|---|---|---|---|
| Peak1 | 10.45 | 10.82 | 11.81 |
| Peak2 | 3.90 | 3.64 | 3.66 |
| Peak3 | 4.57 | 4.59 | 3.88 |
| Peak4 | 5.82 | 5.48 | 5.16 |
| Peak5 | 6.25 | 6.51 | 6.03 |
| Peak6 | 7.65 | 7.42 | 6.95 |
| Peak7 | 8.37 | 8.55 | 7.88 |
| Peak8 | 8.92 | 9.08 | 8.91 |
| Peak9 | 9.48 | 9.43 | 8.92 |
| Peak10 | 9.23 | 9.31 | 9.17 |
| Peak11 | 8.63 | 8.62 | 8.65 |
| Peak12 | 7.52 | 7.44 | 7.87 |
| Peak13 | 5.92 | 5.83 | 6.78 |
| Peak14 | 2.89 | 2.87 | 3.69 |
| Peak15 | 0.41 | 0.41 | 0.65 |

FIG. 11B

| Name | 1.25% (-20C) | 1.25% (25C) | 1.25% 60C |
|---|---|---|---|
| Peak1 | 9.65 | 9.50 | 9.93 |
| Peak2 | 3.14 | 3.44 | 3.33 |
| Peak3 | 3.61 | 3.56 | 4.17 |
| Peak4 | 5.40 | 5.37 | 4.21 |
| Peak5 | 5.62 | 5.94 | 5.67 |
| Peak6 | 7.08 | 6.54 | 6.76 |
| Peak7 | 8.10 | 8.12 | 7.56 |
| Peak8 | 8.69 | 8.54 | 8.90 |
| Peak9 | 9.29 | 9.08 | 9.39 |
| Peak10 | 9.37 | 9.81 | 9.61 |
| Peak11 | 9.38 | 9.23 | 9.11 |
| Peak12 | 8.49 | 8.28 | 8.43 |
| Peak13 | 7.23 | 7.23 | 7.46 |
| Peak14 | 4.17 | 4.21 | 4.56 |
| Peak15 | 0.77 | 1.16 | 0.92 |

FIG. 11C

| Name | 2% (-20C) | 2% (25C) | 2% 60C |
|---|---|---|---|
| Peak1 | 8.41 | 9.05 | 8.79 |
| Peak2 | 2.76 | 3.38 | 3.01 |
| Peak3 | 4.55 | 3.12 | 4.09 |
| Peak4 | 4.60 | 5.16 | 4.10 |
| Peak5 | 5.85 | 5.53 | 5.64 |
| Peak6 | 6.61 | 6.62 | 6.70 |
| Peak7 | 7.80 | 7.42 | 7.25 |
| Peak8 | 8.48 | 8.32 | 8.73 |
| Peak9 | 9.21 | 8.97 | 9.52 |
| Peak10 | 9.42 | 10.04 | 9.75 |
| Peak11 | 9.73 | 9.52 | 9.51 |
| Peak12 | 8.87 | 8.73 | 8.77 |
| Peak13 | 7.85 | 7.64 | 7.90 |
| Peak14 | 4.83 | 4.87 | 5.07 |
| Peak15 | 1.01 | 1.64 | 1.16 |

REDUCTION OF ADIPOSE TISSUE

CROSS-REFERENCES TO RELATED APPLICATIONS

This application is a divisional of U.S. patent application Ser. No. 14/796,686, filed Jul. 10, 2015, now issued at U.S. Pat. No. 9,351,945, which claims the benefit of U.S. Provisional Patent Application No. 62/121,927, filed Feb. 27, 2015 and U.S. Provisional Patent Application No. 62/165,716, filed May 22, 2015, each of which is incorporated herein by reference in its entirety and for all purposes.

BACKGROUND

Procedures for removing fat from the human body have increased in prevalence as the general population has increased in weight and age. Lipoplasty and other surgical methods for removing fat present significant risks including death, high rates of complications, infection, seromas, skin damage, thromboembolism and fluid imbalances. Thus, there is a need in the art for alternative procedures for removal of fat deposits is needed.

Disclosed herein, inter alia, are solutions to these and other problems in the art.

BRIEF SUMMARY

Provided herein, inter alia, are pharmaceutical compositions, formulations, methods, and systems to reduce regional fat, adipose tissue, adipocyte and regional or localized adiposity.

In an aspect is provided a pharmaceutical formulation including: (i) polidocanol in an amount from about 0.1% W/V to about 2.0% W/V; and (ii) a $C_3$-$C_6$ alcohol in an amount from about 0.5% W/V to about 10% W/V. The polidocanol may be from about 0.25% W/V to about 2.0% W/V. In embodiments, the polidocanol may be from about 0.5% W/V to about 2.0% W/V.

In an aspect is provided a method of reducing subcutaneous adipose tissue in a subject in need thereof, the method including administering to the subject a pharmaceutical formulation described herein.

In an aspect is provided a method of reducing subcutaneous adipose tissue in a subject in need thereof. The method includes administering to the subject an effective amount of a pharmaceutical formulation including polidocanol and a co-solvent, where the pharmaceutical formulation is administered within a plurality of treatment sessions, wherein each treatment session is spaced by at least 14 days.

BRIEF DESCRIPTION OF THE DRAWINGS

FIG. 4A: marked sites before injection; FIG. 4B: after trypan blue injection; FIG. 4C: inguinal fat pads after injection. Legends: R: right; L: left.

(FIG. 8A) Group 2A; ID #321 (1 of 9 animals); left: placebo; right: Polidocanol (1.25%); (FIG. 8B) Group 3B; ID #319 (2 of animals); left: placebo; right: Polidocanol (2%). Moderate skin necrosis notes in FIGS. 8A-8B; (FIG. 8C) Group 4; ID #311 (3 of 5 animals); left: placebo; right: Deoxycholate (1%).

FIGS. 9A-9C. Appearance, pH and osmolality stability at time zero (T0) and 1 month (1M); (FIG. 9A) appearance, (FIG. 9B) pH, (FIG. 9C) osmolality.

FIG. 10. Potency (STD curve from top 3 concentrations was used). AUC: area under the curve.

FIGS. 11A-11C. Homologue profile; (FIG. 11A) 0.5% polidocanol, (FIG. 11B) 1.25% polidocanol, (FIG. 11C) 2% polidocanol.

DETAILED DESCRIPTION

Figure 1:
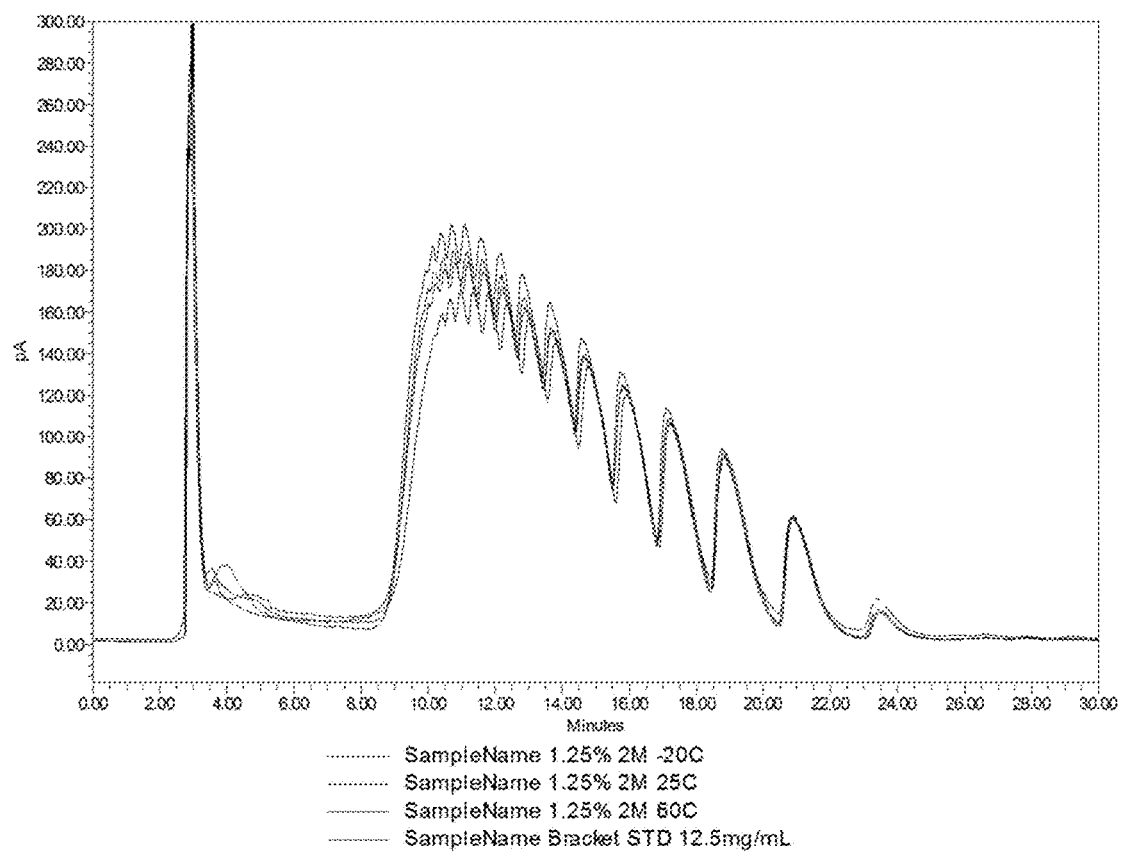
FIG. 1. HPLC profile of the 0.5% polidocanol formulation produced by reacting 1 mole of C12 alcohol with 9 moles of ethylene oxide in the presence of a potassium hydroxide catalyst (HPLC Chromatogram; lower temperatures are at higher PA levels on chromatogram (e.g. 60° C. sample at lowest PA level).

Described herein, inter alia, are adipolytic formulations, non-invasive methods and systems, and kits for body contouring, including reducing, emulsifying, and/or eliminating subcutaneous adipose tissue, including fat deposits. These formulations have been shown to be beneficial, for example, for emulsifying and destroying cell membranes of adipose tissue. Also, described herein is the identification of formulations that contain appropriate excipients that can provide important temperature stability and anti-foaming properties without the drawbacks associated with currently used excipients (e.g., ethanol).

In embodiments, excipients are provided that avoid reduction in the detergent/emulsifying activity of the polidocanol and impediment of the fat destruction effect. In embodiments, certain surfactant excipients do not improve the temperature stability and may worsen problems with foaming. In embodiments, the excipients identified herein have suitable solubility in buffered, isotonic saline solution. Excipients provided herein may have a high safety profile where used for localized destruction of fat, which may be considered an aesthetic indication for which an increased showing of safety may be desired.

Polidocanol and polidocanol-like compounds are disclosed herein. Polidocanol is usually soluble in water and typically does not require an emulsion, such as a microemulsion, formulation for administration. Polidocanol typically does not denature proteins like ionic detergents. Polidocanol may solubilize cell membranes thereby disrupting the cell and tissue leading to cellular and tissue death. In embodiments, this solubilization leads to a more selective and targeted effect on fat tissue and minimizes collateral effects on non-targeted tissues and structures. In embodiments, polidocanol has an average HLB of approximately 13. In embodiments, polidocanol has an average HLB of approximately 12. In embodiments, polidocanol has an average HLB of approximately 12, a critical micelle concentration of approximately 0.07-0.10 millimolar, and an aggregate number of 75-100 and is considered a mild detergent or surfactant. In embodiments, a cosolvent may be used to improve long term stability of polidocanol solution formulation in the range of about 2-40% (W/V).

Definitions

Unless otherwise indicated, concentration percentages are provide as W/V percentage.

The term "polidocanol" is used herein in accordance with its plain, ordinary meaning and includes the active pharmaceutical ingredient by the same name. Polidocanol includes a terminal alcohol connected to a hydrophilic polyethoxylate portion (ethylene glycol units) and a non-polar hydrophobic carbon chain. Polidocanol is typically provided as a synthetic mixture of alkyl ethoxylate homologues. The ethoxylate homologues may have an average carbon chain length from about 10 to about 14 (e.g. about 12). The average number of ethoxylate units may be from about 6 to about 12 (e.g. about 6, 7, 8 or 9). The average number of ethoxylate units may be from about 7 to about 11 (e.g. about 6, 7, 8 or 9). In embodiments, the average number of ethoxylate units is about 6. In embodiments, the average number of ethoxylate units is about 7. In embodiments, the average number of ethoxylate units is about 8. In embodiments, the average number of ethoxylate units is about 9. In embodiments, the polidocanol may be the mixture produced by reacting 1 mole of the corresponding C12 alcohol with 9 moles of ethoxide equivalents (e.g. ethylene oxide). In embodiments, the polidocanol is the product of reacting 1 mole of the corresponding C12 alcohol with 9 moles of ethoxide equivalents under basic conditions (e.g. with a metal base such as potassium hydroxide).

In embodiments, the average molecular weight of the polidocanol (the mixture of alkyl ethoxylates) is about 400 g/mol to about 800 g/mole. In embodiments, the average molecular weight of the polidocanol is about 400 g/mol to about 700 g/mole. In embodiments, the average molecular weight of the polidocanol is about 400 g/mol to about 650 g/mole. In embodiments, the average molecular weight of the polidocanol is about 480 g/mol to about 620 g/mole. In embodiments, the average molecular weight of the polidocanol is about 480 g/mol to about 600 g/mole. In embodiments, the average molecular weight of the polidocanol is about 450 g/mol to about 750 g/mole. In embodiments, the average molecular weight of the polidocanol is about 450 g/mol. In embodiments, the average molecular weight of the polidocanol is about 460 g/mol. In embodiments, the average molecular weight of the polidocanol is about 470 g/mol. In embodiments, the average molecular weight of the polidocanol is about 480 g/mol. In embodiments, the average molecular weight of the polidocanol is about 490 g/mol. In embodiments, the average molecular weight of the polidocanol is about 500 g/mol. In embodiments, the average molecular weight of the polidocanol is about 510 g/mol. In embodiments, the average molecular weight of the polidocanol is about 520 g/mol. In embodiments, the average molecular weight of the polidocanol is about 530 g/mol. In embodiments, the average molecular weight of the polidocanol is about 540 g/mol. In embodiments, the average molecular weight of the polidocanol is about 550 g/mol. In embodiments, the average molecular weight of the polidocanol is about 560 g/mol. In embodiments, the average molecular weight of the polidocanol is about 570 g/mol. In embodiments, the average molecular weight of the polidocanol is about 580 g/mol. In embodiments, the average molecular weight of the polidocanol is about 590 g/mol. In embodiments, the average molecular weight of the polidocanol is about 600 g/mol. In embodiments, the average molecular weight of the polidocanol is about 625 g/mol. In embodiments, the average molecular weight of the polidocanol is about 650 g/mol. In embodiments, the average molecular weight of the polidocanol is about 493 g/mol. In embodiments, the average molecular weight of the polidocanol is 493 g/mol.

In embodiments, the polidocanol contains a mixture of C12 ethoxylates (e.g. with homologues) ranging from 3-18 ethoxide units. In embodiments, the polidocanol contains a mixture of C12 ethoxylates ranging from 1-23 ethoxide units. In embodiments, the polidocanol contains a mixture of C12 ethoxylates ranging from 15-20 ethoxide units. In embodiments, there are approximately 15 ethoxylated C12 molecular species. In embodiments, no one ethoxylated species is present at more than 20% of the total alkyl ethoxylates, in some not more than 15% and in some not more than 10%. In embodiments, the average degree of ethoxylation is 7. In embodiments, the average degree of ethoxylation is 8, 9, 10 or 11. In embodiments, C14 alkyl ethoxylate units are present in the polidocanol mixture. In embodiments, the average ethoxylation is 6, in some it is 7, in others it is 8 and in others it is 9. In embodiments, a polidocanol with a narrow range of ethoxylate units is produced from a reaction involving catalysts, such as metal oxide, that produces ethoxylated alcohols in the range of 6-11. In embodiments, the average molecular weight of the alkyl ethoxylated homologues is approximately 440 g/mole. In embodiments, the average molecular weight of the alkyl ethoxylated homologues is 500 g/mol, in some embodiments 600 g/mole.

A "$C_3$-$C_6$ alcohol," as used herein, refers to a compound having from 1 to 3 carbons and at least one hydroxyl moiety. In embodiments, the $C_3$-$C_6$ alcohol contains an alkyl chain of from 3 to 6 carbons, wherein each carbon is substituted with hydrogen or hydroxyl. In embodiments, the $C_3$-$C_6$ alcohol contains an alkyl chain of from 3 to 6 carbons, wherein each carbon is substituted with hydrogen or hydroxyl, and the $C_3$-$C_6$ alcohol contains 1 to 6 hydroxyl moieties. In embodiments, the $C_3$-$C_6$ alcohol contains an alkyl chain of from 3 to 6 carbons, wherein each carbon is substituted with hydrogen or hydroxyl, and the $C_3$-$C_6$ alcohol contains 1 to 3 hydroxyl moieties. In embodiments, the $C_3$-$C_6$ alcohol contains an alkyl chain of from 3 to 6 carbons, wherein each carbon is substituted with hydrogen or hydroxyl, and the $C_3$-$C_6$ alcohol contains 1 or 2 hydroxyl moieties. In embodiments, the $C_3$-$C_6$ alcohol contains an alkyl chain of from 3 to 6 carbons, wherein each carbon is substituted with hydrogen or hydroxyl, and the $C_3$-$C_6$ alcohol contains 2 hydroxyl moieties. In embodiments, the $C_3$-$C_6$ alcohol contains an alkyl chain of 3 carbons (i.e. a $C_3$ alcohol), wherein each carbon is substituted with hydrogen or hydroxyl, and the $C_3$ alcohol contains 1 to 3 hydroxyl moieties. In embodiments, the $C_3$-$C_6$ alcohol contains an alkyl chain of 3 carbons (i.e. a $C_3$ alcohol), wherein each carbon is substituted with hydrogen or hydroxyl, and the $C_3$ alcohol contains 1 or 2 hydroxyl moieties. In embodiments, the $C_3$-$C_6$ alcohol contains an alkyl chain of 3 carbons (i.e.

a $C_3$ alcohol), wherein each carbon is substituted with hydrogen or hydroxyl, and the $C_3$ alcohol contains 2 hydroxyl moieties. In embodiments, the $C_3$-$C_6$ alcohol is a propane-diol. In embodiments, the $C_3$-$C_6$ alcohol is a propane-1,2-diol (propylene glycol).

As used herein, the term "polidocanol-like compound" refers to a compound of Formula I or Formula II described herein, including embodiments thereof.

An "effective amount" is an amount sufficient to accomplish a stated purpose (e.g. achieve the effect for which it is administered, treat a disease, reduce adipose tissue or cells, lyse cells, reduce one or more symptoms of a disease or condition). An example of an "effective amount" is an amount sufficient to contribute to the treatment, prevention, or reduction of a symptom or symptoms of a disease or condition, which could also be referred to as a "therapeutically effective amount." A "therapeutically effective amount," as used herein, refers to a sufficient amount of an agent (e.g., polidocanol) or other compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses may be the amount of the composition including a compound as disclosed herein required to provide a clinically significant decrease in disease symptoms without undue adverse side effects. An appropriate "effective amount" in any individual case can be determined using techniques, such as a dose escalation study. The term "therapeutically effective amount" includes, for example, a prophylactically effective amount. An "effective amount" of a compound disclosed herein, such as polidocanol used alone or in combination with other compounds, is an amount effective to achieve a desired pharmacologic effect or therapeutic improvement without undue adverse side effects. It is to be understood that "an effective amount" or "a therapeutically effective amount" can vary from subject to subject, due to variation in metabolism of a compound of Formula I or Formula II as described herein (such as polidocanol), age, weight, general condition of the subject, the condition being treated, the severity of the condition being treated, and the judgment of the prescribing physician. A "cosmetically effective amount" as used herein refers to the amount of a compound sufficient to improve the outward physical appearance of a subject. The outward physical appearance of a subject includes, for example, the reduction of fat deposition in certain regions of the body including, for example, the midsection of the body. In embodiments, a cosmetically effective amount refers to a sufficient amount of an agent (e.g., polidocanol) which will improve the cosmetic appearance at the localized site of treatment. A cosmetically effective amount of polidocanol may be an amount effective to achieve a cosmetically desirable improvement. It is to be understood that a cosmetically effective amount can vary from subject to subject, due to numerous factors including for example age, weight, general condition of the subject, the condition being treated, the severity of the condition being treated, and the judgment of the prescribing physician. For example, a cosmetically effective amount of an agent (e.g., polidocanol) may be an amount capable of improving the cosmetic appearance at the localized site of treatment by reducing the amount of adipose tissue or cells at the localized size or an area adjacent to the localized site of treatment.

In certain embodiments, the phrase "pharmaceutically acceptable salt(s) and other suitable forms", and similar language as used herein, means those salts, solvates, hydrates, and other suitable forms of compounds described herein that are safe and effective for administration in mammals. Pharmaceutically acceptable salts include salts of acidic or basic groups present in compounds described herein. In certain embodiments, the pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. In certain embodiments, one or more compounds described herein form pharmaceutically acceptable salts with various amino acids. In certain embodiments, the base salts include, but are not limited to, aluminum, calcium, lithium, magnesium, potassium, sodium, zinc, and diethanolamine salts. Pharmaceutically acceptable salts in certain embodiments of the formulations described herein, are as described in BERGE ET AL., 66 J. PHARM. SCI. 1-19 (1977), incorporated in entirety by reference herein.

In certain embodiments, the term "cosmetically acceptable salt and other suitable forms" and similar language used herein means any salt, hydrate, solvate, or other suitable form that is cosmetically tolerated if used appropriately for a cosmetic treatment especially if used on or applied to humans and/or mammals. In certain embodiments, these salts include, but are not restricted to the salts used to form base addition salts, either inorganic, such as for example and in a non-limiting sense, lithium, sodium, potassium, calcium, magnesium or aluminium, among others, or organic such as for example and in a non-limiting sense, ethylamine, diethylamine, ethylenediamine, ethanolamine, diethanolamine, arginine, lysine, histidine, or piperazine among others; or acid addition salts, either organic, such as for example and in a non-limiting sense, acetate, citrate, lactate, malonate, maleate, tartrate, fumarate, benzoate, aspartate, glutamate, succinate, oleate, trifluoroacetate, oxalate, pamoate or gluconate among others, or inorganic, such as for example and in a non-limiting sense, chloride, sulfate, borate, or carbonate among others. The cosmetically acceptable salts described herein can be obtained by conventional methods well known in the state of the art as described in BERGE ET AL., 66 J. PHARM. SCI. 1-19 (1977), incorporated in entirety by reference herein.

"Pharmaceutically acceptable excipient" and "pharmaceutically acceptable carrier" refer to a substance that aids the administration of an active agent to a subject and can be included in the compositions described herein without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, mannitol, gum acacia, calcium phosphate, alginates, tragacanth, calcium silicate, microcrystalline cellulose, cellulose, syrup, and methyl cellulose, colors, and the like. The formulations can additionally include: lubricating agents such as talc, magnesium stearate, and mineral oil; wetting agents; emulsifying and suspending agents; preserving agents such as methyl and propylhydroxy benzoates;

sweetening agents; and flavoring agents. The compositions described herein can be formulated so as to provide quick, sustained or delayed release of the active ingredient after administration to the patient by employing procedures known in the art. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

Any suitable pharmaceutically acceptable excipient appropriate for a particular route of administration can be used. Examples of pharmaceutically acceptable carriers include, but are not limited to, buffers, saline, or other aqueous media. The compounds of the invention are preferably soluble in the carrier which is employed for their administration (e.g., subcutaneous). Alternatively, a suspension of the active compound or compounds (e.g., a suspension of microparticles) in a suitable carrier is employed. Some embodiments include any suitable lipophilic carrier, for example, modified oils (e.g., CREMOPHOR® BASF, Germany), soybean oil, polyethylene glycol, derivatized polyethers, combinations thereof, and the like. Some embodiments include a microparticulate and/or a nanoparticulate carrier. Some embodiments include one or more sustained or controlled release carriers or agents, for example, polymer microspheres. Some embodiments include excipients suitable for stable suspensions for micronized particles of polidocanol. In further or additional embodiments, the formulations include an immediate release excipient. In embodiments, the pharmaceutically excipient is not a $C_3$-$C_6$ alcohol (e.g. propylene glycol).

The term "fat pad" refers herein to any cushions made of a pocket of fascia and filled with fat deposits (e.g. fatty acids) that are present in humans or mammalians.

As used herein, "administering" means administering by any route, including local, parenteral, by infusion, injection, implantation, or subcutaneous administration. For example, the formulations described herein can be administered by subcutaneous injection or delivery. For example, the formulations described herein can be administered by intravenous injection or delivery. As used herein, a formulation formulated for subcutaneous injection can include sterile isotonic aqueous buffer. Where necessary, the compositions can also include a solubilizing agent.

Embodiments of the composition are formulated for administration by any suitable method, for example, as described in *Remington: The Science And Practice Of Pharmacy* (21st ed., Lippincott Williams & Wilkins). Exemplary routes of administration include, but are not limited to parenteral, oral, subcutaneous, topical, intramuscular, transdermal, transmucosal, sublingual, intranasal, transvascular, subcutaneous, orbital, or respiratory. In some embodiments, the composition is formulated for injection of an area at which treatment is desired, for example, in a regional fat deposit, such as for example excessive sub-mental adiposity. In some embodiments, provided are methods for subcutaneous delivery as well as compositions and formulations that are formulated to be suitable for subcutaneous delivery.

Injectable formulations are administered using any method known in the art, for example, using a single needle, multiple needles, and/or using a needleless injection device. In some embodiments, a tissue loading dose of the active ingredients formulated in a suitable carrier delivered by injection. In some embodiments, delivery includes single needle injection. In some embodiments, delivery includes injection using a multi-needle array, which, in some embodiments, provides a wide dispersion of the formulation in the target tissue. In some embodiments, formulations are injected in a manner that allows dispersal into the appropriate layer of subcutaneous fat in areas where regional fat exists. In some embodiments, a micropump is used to deliver the injectable formulations.

The formulations described herein may also be administered via a device. A number of devices have been proposed to facilitate self-administration of pharmaceutical formulations. The device typically includes a reservoir containing, for example, pre-loaded with, the pharmaceutical formulation to be administered. For example, a micropump can provide precise subcutaneous administration of small quantities of a liquid pharmaceutical formulation. Such micropumps can be compact and portable. Another type of device useful for subcutaneous delivery or administration of pharmaceutical formulations is often referred to as a patch device or a pump-patch device. Patch devices usually are attached directly to the skin of a patient.

Accordingly, in various embodiments, a device such as a micropump or patch device can include a reservoir containing a pharmaceutical formulation, a subcutaneous injection needle configured for removable insertion into skin of a patient, a micropump having an inlet in fluid communication with the reservoir and an outlet in fluid communication with the subcutaneous injection needle, a control system configured for controlling the micropump to deliver the pharmaceutical formulation from the reservoir to the subcutaneous injection needle, whereby the pharmaceutical formulation is administered subcutaneously to a patient, and a housing for supporting the reservoir, subcutaneous injection needle, micropump and control system, the housing being portable and adapted for contact with the skin of the patient. The pharmaceutical formulation contained within the reservoir can be any of the pharmaceutical formulations of the present teachings, for example, a pharmaceutical formulation including an effective amount, including for example a therapeutically or cosmetically effective amount, of polidocanol and from about 0.5% W/V to about 10% W/V of an alcohol having 3 to 6 carbon atoms (i.e. a $C_3$-$C_6$ alcohol).

In certain embodiments, the device can be of a unitary construction. Such devices can be for a single or one-time use. In particular embodiments, the device can be of a multi-piece construction, in such devices, a disposable or a re-sizeable portion or component can be present. For example, a housing defining or including the reservoir can be a disposable or a reusable component of the device, in some embodiments, the disposable or reusable housing defining or including the reservoir can contain a pharmaceutical formulation of the present teachings. In various embodiments, the subcutaneous injection needle can be a disposable component of the device. When administered for the treatment or inhibition of a particular disease state, condition or disorder, it is understood that an effective dosage can vary depending upon many factors such as the particular compound or therapeutic combination utilized, the mode of administration, and severity of the condition being treated, as well as the various physical factors related to the individual being treated. In therapeutic applications, a compound or therapeutic combination of the present teachings can be provided to a patient already suffering from a disorder, for example, subcutaneous adipose tissue, in an amount sufficient to reduce and/or prevent the symptoms of the disorder and its complications. The dosage to be used in the treatment of a specific individual typically must be subjectively determined by the attending physician. The variables involved include the specific condition and its state as well as the size, age and response pattern of the patient.

The term "about" when used in conjunction with a numerical value indicates the value is within 10% of the numerical value. In embodiments, "about" means within 5% of the numerical value. In embodiments, "about" means within 1% of the numerical value. For example, about 1.0% means 0.9% to 1.1%. It will be understood that the indicated value is included as an embodiment within the range specified by the use of "about" referring to the numerical value. In embodiments, "approximately" when applied to a numerical value has the same meaning as "about".

The term "buffer" is used in accordance with its common meaning within the biological sciences and refers to a solution including a mixture of a weak acid and its conjugate base or a weak base and its conjugate acid. A buffer has the property that the pH of the solution changes very little when a small amount of acid or base is added to it. Buffer solutions are used as a means of keeping pH at a nearly constant value in a wide variety of chemical applications. Examples of suitable buffers include phosphate buffers and those known in the literature (see, for example, Troy, D. B., ed. (2005) Remington: The Science and Practice of Pharmacy, 21st ed., Lippincott Williams & Wilkins).

Compositions

In an aspect is provided a pharmaceutical formulation including polidocanol in an amount from about 0.5% W/V to about 2.0% W/V; and a $C_3$-$C_6$ alcohol in an amount from about 0.5% W/V to about 10% W/V.

In embodiments, the pharmaceutical formulation consists essentially of polidocanol in an amount from about 0.5% W/V to about 2.0% W/V; and a $C_3$-$C_6$ alcohol in an amount from about 0.5% W/V to about 10% W/V. The term "consisting essentially of" in this context refers to a pharmaceutical formulation comprising polidocanol, a $C_3$-$C_6$ alcohol and no other component that is independently capable of reducing fat according to the methods described herein.

In embodiments, the pharmaceutical formulations described herein do not include a beta-2-adrenergic receptor agonist (e.g. bambuterol, bitolterol, broxaterol, carbuterol, carmoterol, clenbuterol, ibuterol, sulfonterol, isoproterenol, trimetoquinol, formoterol, desformoterol, hexoprenaline, ibuterol, indacaterol, isoetharine, isoprenaline, isoproterenol, levalbuterol, metaproterenol, picumeterol, pirbuterol, procaterol, reproterol, rimiterol, salbutamol, salmeterol; sulfonterol, terbutaline, trimetoquinol, tulobuterol, TA-2005 (8-hydroxy-5-((1R)-1-hydroxy-2-(N-((1R)-2-(4-methoxyphenyl)-1-methylethyl-)amino)ethyl)-carbostyril hydrochloride), QAB-149 (Novartis), TA-2005, GSK-159797, or GSK-642444, or a salt, optical isomer, racemate, solvate, or polymorph thereof) or a pharmaceutically acceptable or cosmetically acceptable salt thereof.

In embodiments, the pharmaceutical formulations described herein do not include a ketotifen or analog of ketotifen or a pharmaceutically acceptable or cosmetically acceptable salt thereof. In embodiments, the pharmaceutical formulations described herein do not include a thyroid hormone (e.g. thyroxine (T4) or triiodothyronine (T3)) a pharmaceutically acceptable or cosmetically acceptable salt thereof. In embodiments, the pharmaceutical formulations described herein do not include a natriuretic peptide (e.g. atrial natriuretic peptide (ANP), brain natriuretic peptide (BNP), C-type natriuretic peptide, and dendroaspis natriuretic peptide, natriuretic peptide receptor A (NPrA), natriuretic peptide receptor (NPrB)) a pharmaceutically acceptable or cosmetically acceptable salt thereof. In embodiments, the pharmaceutical formulations described herein do not include 1, 25-dihydroxy Vitamin D3 or its analogues a pharmaceutically acceptable or cosmetically acceptable salt thereof.

In embodiments, the pharmaceutical formulations described herein do not include glycerol. In embodiments, the pharmaceutical formulations described herein do not include polyethylene glycol. In embodiments, the pharmaceutical formulations described are not topical compositions (such as a topical gel composition). In embodiments, the pharmaceutical formulations described herein do not include hydroxypropyl cellulose. In embodiments, the pharmaceutical formulations described herein do not include isopropyl myristate.

In embodiments, the pharmaceutical formulations described herein are not oral compositions. In embodiments, the pharmaceutical formulations described herein do not include starch. In embodiments, the pharmaceutical formulations described herein do not include gelatin. In embodiments, the pharmaceutical formulations described herein do not include hydroxypropylmethyl cellulose.

In embodiments, the pharmaceutical formulations described herein are not an emulsion. In embodiments, the pharmaceutical formulations described herein are not a micro-emulsion. In embodiments, the pharmaceutical formulations described herein do not include a lipophilic substance (e.g. natural oils, esters of middle-chain alkylacids with glycols, octyl-dodecanol, silicon oils, paraffins and vitamins). In embodiments, the pharmaceutical formulations described herein do not include a compound having an HLB of 6 or less. In embodiments, the pharmaceutical formulations described herein do not include a compound having an HLB of 5 or less. In embodiments, the pharmaceutical formulations described herein do not include a compound having an HLB of 4 or less. In embodiments, the pharmaceutical formulations described herein do not include a compound having an HLB of 3 or less. In embodiments, the pharmaceutical formulations described herein do not include a compound having an HLB of 7 or less. In embodiments, the pharmaceutical formulations described herein do not include a compound having an HLB of 8 or less.

In embodiments, the pharmaceutical formulation include polidocanol in an amount from about 0.5% W/V to about 2.0% W/V; and a $C_3$-$C_6$ alcohol in an amount from about 0.5% W/V to about 10% W/V as the only active agents.

In embodiments, the polidocanol is in an amount from about 0.5% W/V to about 2.00% W/V. In embodiments, the polidocanol is in an amount from about 0.5% W/V to about 1.95% W/V. In embodiments, the polidocanol is in an amount from about 0.5% W/V to about 1.90% W/V. In embodiments, the polidocanol is in an amount from about 0.5% W/V to about 1.85% W/V. In embodiments, the polidocanol is in an amount from about 0.5% W/V to about 1.80% W/V. In embodiments, the polidocanol is in an amount from about 0.5% W/V to about 1.75% W/V. In embodiments, the polidocanol is in an amount from about 0.5% W/V to about 1.70% W/V. In embodiments, the polidocanol is in an amount from about 0.5% W/V to about 1.65% W/V. In embodiments, the polidocanol is in an amount from about 0.5% W/V to about 1.60% W/V. In embodiments, the polidocanol is in an amount from about 0.5% W/V to about 1.55% W/V. In embodiments, the polidocanol is in an amount from about 0.5% W/V to about 1.50% W/V. In embodiments, the polidocanol is in an amount from about 0.5% W/V to about 1.45% W/V. In embodiments, the polidocanol is in an amount from about 0.5% W/V to about 1.40% W/V. In embodiments, the polidocanol is in an amount from about 0.5% W/V to about 1.35% W/V. In embodiments, the polidocanol is in an amount from about 0.5% W/V to about 1.30% W/V. In embodiments, the polidocanol is in an amount from about 0.5% W/V to about 1.25% W/V. In embodiments, the polidocanol is in an amount from about 0.5% W/V to about 1.20% W/V. In embodiments, the polidocanol is in an amount from about 0.5% W/V to about 1.15% W/V. In embodiments, the polidocanol is in an amount from about 0.5% W/V to about 1.10% W/V. In embodiments, the polidocanol is in an amount from about 0.5% W/V to about 1.05% W/V. In embodiments, the polidocanol is in an amount from about 0.5% W/V to about 1.00% W/V. In embodiments, the polidocanol is in an amount from about 0.5% W/V to about 0.95% W/V. In embodiments, the polidocanol is in an amount from about 0.5% W/V to about 0.90% W/V. In embodiments, the polidocanol is in an amount from about 0.5% W/V to about 0.85% W/V. In embodiments, the polidocanol is in an amount from about 0.5% W/V to about 0.80% W/V. In embodiments, the polidocanol is in an amount from about 0.5% W/V to about 0.75% W/V. In embodiments, the polidocanol is in an amount from about 0.5% W/V to about 0.70% W/V.

In embodiments, the polidocanol is in an amount from 0.5% W/V to 2.00% W/V. In embodiments, the polidocanol is in an amount from 0.5% W/V to 1.95% W/V. In embodiments, the polidocanol is in an amount from 0.5% W/V to 1.90% W/V. In embodiments, the polidocanol is in an amount from 0.5% W/V to 1.85% W/V. In embodiments, the polidocanol is in an amount from 0.5% W/V to 1.80% W/V. In embodiments, the polidocanol is in an amount from 0.5% W/V to 1.75% W/V. In embodiments, the polidocanol is in an amount from 0.5% W/V to 1.70% W/V. In embodiments, the polidocanol is in an amount from 0.5% W/V to 1.65% W/V. In embodiments, the polidocanol is in an amount from 0.5% W/V to 1.60% W/V. In embodiments, the polidocanol is in an amount from 0.5% W/V to 1.55% W/V. In embodiments, the polidocanol is in an amount from 0.5% W/V to 1.50% W/V. In embodiments, the polidocanol is in an amount from 0.5% W/V to 1.45% W/V. In embodiments, the polidocanol is in an amount from 0.5% W/V to 1.40% W/V. In embodiments, the polidocanol is in an amount from 0.5% W/V to 1.35% W/V. In embodiments, the polidocanol is in an amount from 0.5% W/V to 1.30% W/V. In embodiments, the polidocanol is in an amount from 0.5% W/V to 1.25% W/V. In embodiments, the polidocanol is in an amount from 0.5% W/V to 1.20% W/V. In embodiments, the polidocanol is in an amount from 0.5% W/V to 1.15% W/V. In embodiments, the polidocanol is in an amount from 0.5% W/V to 1.10% W/V. In embodiments, the polidocanol is in an amount from 0.5% W/V to 1.05% W/V. In embodiments, the polidocanol is in an amount from 0.5% W/V to 1.00% W/V. In embodiments, the polidocanol is in an amount from 0.5% W/V to 0.95% W/V. In embodiments, the polidocanol is in an amount from 0.5% W/V to 0.90% W/V. In embodiments, the polidocanol is in an amount from 0.5% W/V to 0.85% W/V. In embodiments, the polidocanol is in an amount from 0.5% W/V to 0.80% W/V. In embodiments, the polidocanol is in an amount from 0.5% W/V to 0.75% W/V. In embodiments, the polidocanol is in an amount from 0.5% W/V to 0.70% W/V.

In embodiments, the polidocanol is in an amount from about 0.55% W/V to about 2.00% W/V. In embodiments, the polidocanol is in an amount from about 0.60% W/V to about 2.00% W/V. In embodiments, the polidocanol is in an amount from about 0.65% W/V to about 2.00% W/V. In embodiments, the polidocanol is in an amount from about 0.70% W/V to about 2.00% W/V. In embodiments, the polidocanol is in an amount from about 0.75% W/V to about 2.00% W/V. In embodiments, the polidocanol is in an amount from about 0.80% W/V to about 2.00% W/V. In embodiments, the polidocanol is in an amount from about 0.85% W/V to about 2.00% W/V. In embodiments, the polidocanol is in an amount from about 0.90% W/V to about 2.00% W/V. In embodiments, the polidocanol is in an amount from about 0.95% W/V to about 2.00% W/V. In embodiments, the polidocanol is in an amount from about 1.00% W/V to about 2.00% W/V. In embodiments, the polidocanol is in an amount from about 1.05% W/V to about 2.00% W/V. In embodiments, the polidocanol is in an amount from about 1.10% W/V to about 2.00% W/V. In embodiments, the polidocanol is in an amount from about 1.15% W/V to about 2.00% W/V. In embodiments, the polidocanol is in an amount from about 1.20% W/V to about 2.00% W/V. In embodiments, the polidocanol is in an amount from about 1.25% W/V to about 2.00% W/V. In embodiments, the polidocanol is in an amount from about 1.30% W/V to about 2.00% W/V. In embodiments, the polidocanol is in an amount from about 1.35% W/V to about 2.00% W/V. In embodiments, the polidocanol is in an amount from about 1.40% W/V to about 2.00% W/V. In embodiments, the polidocanol is in an amount from about 1.45% W/V to about 2.00% W/V. In embodiments, the polidocanol is in an amount from about 1.50% W/V to about 2.00% W/V. In embodiments, the polidocanol is in an amount from about 1.55% W/V to about 2.00% W/V.

In embodiments, the polidocanol is in an amount from 0.55% W/V to 2.00% W/V. In embodiments, the polidocanol is in an amount from 0.60% W/V to 2.00% W/V. In embodiments, the polidocanol is in an amount from 0.65% W/V to 2.00% W/V. In embodiments, the polidocanol is in an amount from 0.70% W/V to 2.00% W/V. In embodiments, the polidocanol is in an amount from 0.75% W/V to 2.00% W/V. In embodiments, the polidocanol is in an amount from 0.80% W/V to 2.00% W/V. In embodiments, the polidocanol is in an amount from 0.85% W/V to 2.00% W/V. In embodiments, the polidocanol is in an amount from 0.90% W/V to 2.00% W/V. In embodiments, the polidocanol is in an amount from 0.95% W/V to 2.00% W/V. In embodiments, the polidocanol is in an amount from 1.00% W/V to 2.00% W/V. In embodiments, the polidocanol is in an amount from 1.05% W/V to 2.00% W/V. In embodiments, the polidocanol is in an amount from 1.10% W/V to 2.00% W/V. In embodiments, the polidocanol is in an amount from 1.15% W/V to 2.00% W/V. In embodiments, the polidocanol is in an amount from 1.20% W/V to 2.00% W/V. In embodiments, the polidocanol is in an amount from 1.25% W/V to 2.00% W/V. In embodiments, the polidocanol is in an amount from 1.30% W/V to 2.00% W/V. In embodiments, the polidocanol is in an amount from 1.35% W/V to 2.00% W/V. In embodiments, the polidocanol is in an amount from 1.40% W/V to 2.00% W/V. In embodiments, the polidocanol is in an amount from 1.45% W/V to 2.00% W/V. In embodiments, the polidocanol is in an amount from 1.50% W/V to 2.00% W/V. In embodiments, the polidocanol is in an amount from 1.55% W/V to 2.00% W/V.

In embodiments, the polidocanol is in an amount from about 0.55% W/V to about 1.95% W/V. In embodiments, the polidocanol is in an amount from about 0.60% W/V to about 1.90% W/V. In embodiments, the polidocanol is in an amount from about 0.65% W/V to about 1.85% W/V. In embodiments, the polidocanol is in an amount from about 0.70% W/V to about 1.80% W/V. In embodiments, the polidocanol is in an amount from about 0.75% W/V to about 1.75% W/V. In embodiments, the polidocanol is in an amount from about 0.80% W/V to about 1.70% W/V. In embodiments, the polidocanol is in an amount from 0.85% W/V to about 1.65% W/V. In embodiments, the polidocanol is in an amount from about 0.90% W/V to about 1.60% W/V. In embodiments, the polidocanol is in an amount from about 0.95% W/V to about 1.55% W/V. In embodiments, the polidocanol is in an amount from about 1.00% W/V to about 1.50% W/V. In embodiments, the polidocanol is in an amount from about 1.05% W/V to about 1.45% W/V. In embodiments, the polidocanol is in an amount from about 1.10% W/V to about 1.40% W/V. In embodiments, the polidocanol is in an amount from about 1.15% W/V to about 1.35% W/V. In embodiments, the polidocanol is in an amount from about 1.20% W/V to about 1.30% W/V.

In embodiments, the polidocanol is in an amount from 0.55% W/V to 1.95% W/V. In embodiments, the polidocanol is in an amount from 0.60% W/V to 1.90% W/V. In embodiments, the polidocanol is in an amount from 0.65% W/V to 1.85% W/V. In embodiments, the polidocanol is in an amount from 0.70% W/V to 1.80% W/V. In embodiments, the polidocanol is in an amount from 0.75% W/V to 1.75% W/V. In embodiments, the polidocanol is in an amount from 0.80% W/V to 1.70% W/V. In embodiments, the polidocanol is in an amount from 0.85% W/V to 1.65% W/V. In embodiments, the polidocanol is in an amount from 0.90% W/V to 1.60% W/V. In embodiments, the polidocanol is in an amount from 0.95% W/V to 1.55% W/V. In embodiments, the polidocanol is in an amount from 1.00% W/V to 1.50% W/V. In embodiments, the polidocanol is in an amount from 1.05% W/V to 1.45% W/V. In embodiments, the polidocanol is in an amount from 1.10% W/V to 1.40% W/V. In embodiments, the polidocanol is in an amount from 1.15% W/V to 1.35% W/V. In embodiments, the polidocanol is in an amount from 1.20% W/V to 1.30% W/V.

In embodiments, the polidocanol is in an amount of about 0.55% W/V. In embodiments, the polidocanol is in an amount of about 0.60% W/V. In embodiments, the polidocanol is in an amount of about 0.65% W/V. In embodiments, the polidocanol is in an amount of about 0.70% W/V. In embodiments, the polidocanol is in an amount of about 0.75% W/V. In embodiments, the polidocanol is in an amount of about 0.80% W/V. In embodiments, the polidocanol is in an amount of about 0.85% W/V. In embodiments, the polidocanol is in an amount of about 0.90% W/V. In embodiments, the polidocanol is in an amount of about 0.95% W/V. In embodiments, the polidocanol is in an amount of about 1.00% W/V. In embodiments, the polidocanol is in an amount of about 1.05% W/V. In embodiments, the polidocanol is in an amount of about 1.10% W/V. In embodiments, the polidocanol is in an amount of about 1.15% W/V. In embodiments, the polidocanol is in an amount of about 1.20% W/V. In embodiments, the polidocanol is in an amount of about 1.25% W/V. In embodiments, the polidocanol is in an amount of about 1.30% W/V. In embodiments, the polidocanol is in an amount of about 1.35% W/V. In embodiments, the polidocanol is in an amount of about 1.40% W/V. In embodiments, the polidocanol is in an amount of about 1.45% W/V. In embodiments, the polidocanol is in an amount of about 1.50% W/V. In embodiments, the polidocanol is in an amount of about 1.55% W/V.

In embodiments, the polidocanol is in an amount of 0.55% W/V. In embodiments, the polidocanol is in an amount of 0.60% W/V. In embodiments, the polidocanol is in an amount of 0.65% W/V. In embodiments, the polidocanol is in an amount of 0.70% W/V. In embodiments, the polidocanol is in an amount of 0.75% W/V. In embodiments, the polidocanol is in an amount of 0.80% W/V. In embodiments, the polidocanol is in an amount of 0.85% W/V. In embodiments, the polidocanol is in an amount of 0.90% W/V. In embodiments, the polidocanol is in an amount of 0.95% W/V. In embodiments, the polidocanol is in an amount of 1.00% W/V. In embodiments, the polidocanol is in an amount of 1.05% W/V. In embodiments, the polidocanol is in an amount of 1.10% W/V. In embodiments, the polidocanol is in an amount of 1.15% W/V. In embodiments, the polidocanol is in an amount of 1.20% W/V. In embodiments, the polidocanol is in an amount of 1.25% W/V. In embodiments, the polidocanol is in an amount of 1.30% W/V. In embodiments, the polidocanol is in an amount of 1.35% W/V. In embodiments, the polidocanol is in an amount of 1.40% W/V. In embodiments, the polidocanol is in an amount of 1.45% W/V. In embodiments, the polidocanol is in an amount of 1.50% W/V. In embodiments, the polidocanol is in an amount of 1.55% W/V.

In embodiments, the $C_3$-$C_6$ alcohol is propylene glycol.

In embodiments, the $C_3$-$C_6$ alcohol (e.g., propylene glycol) is present in an amount from about 2.0% W/V to about 5.0% W/V. In embodiments, the $C_3$-$C_6$ alcohol (e.g., propylene glycol) is present in an amount from about 2.2% W/V to about 5.0% W/V. In embodiments, the $C_3$-$C_6$ alcohol (e.g., propylene glycol) is present in an amount from about 2.4% W/V to about 5.0% W/V. In embodiments, the $C_3$-$C_6$ alcohol (e.g., propylene glycol) is present in an amount from about 2.6% W/V to about 5.0% W/V. In embodiments, the $C_3$-$C_6$ alcohol (e.g., propylene glycol) is present in an amount from about 2.8% W/V to about 5.0% W/V. In embodiments, the $C_3$-$C_6$ alcohol (e.g., propylene glycol) is present in an amount from about 3.0% W/V to about 5.0% W/V. In embodiments, the $C_3$-$C_6$ alcohol (e.g., propylene glycol) is present in an amount from about 3.2% W/V to about 5.0% W/V. In embodiments, the $C_3$-$C_6$ alcohol (e.g., propylene glycol) is present in an amount from about 3.4% W/V to about 5.0% W/V. In embodiments, the $C_3$-$C_6$ alcohol (e.g., propylene glycol) is present in an amount from about 3.6% W/V to about 5.0% W/V. In embodiments, the $C_3$-$C_6$ alcohol (e.g., propylene glycol) is present in an amount from about 3.8% W/V to about 5.0% W/V. In embodiments, the $C_3$-$C_6$ alcohol (e.g., propylene glycol) is present in an amount from about 4.0% W/V to about 5.0% W/V. In embodiments, the $C_3$-$C_6$ alcohol (e.g., propylene glycol) is present in an amount from about 4.2% W/V to about 5.0% W/V. In embodiments, the $C_3$-$C_6$ alcohol (e.g., propylene glycol) is present in an amount from about 4.4% W/V to about 5.0% W/V.

In embodiments, the $C_3$-$C_6$ alcohol (e.g., propylene glycol) is present in an amount from 2.0% W/V to 5.0% W/V. In embodiments, the $C_3$-$C_6$ alcohol (e.g., propylene glycol) is present in an amount from 2.2% W/V to 5.0% W/V. In embodiments, the $C_3$-$C_6$ alcohol (e.g., propylene glycol) is present in an amount from 2.4% W/V to 5.0% W/V. In embodiments, the $C_3$-$C_6$ alcohol (e.g., propylene glycol) is present in an amount from 2.6% W/V to 5.0% W/V. In embodiments, the $C_3$-$C_6$ alcohol (e.g., propylene glycol) is present in an amount from 2.8% W/V to 5.0% W/V. In embodiments, the $C_3$-$C_6$ alcohol (e.g., propylene glycol) is present in an amount from 3.0% W/V to 5.0% W/V. In embodiments, the $C_3$-$C_6$ alcohol (e.g., propylene glycol) is present in an amount from 3.2% W/V to 5.0% W/V. In embodiments, the $C_3$-$C_6$ alcohol (e.g., propylene glycol) is present in an amount from 3.4% W/V to 5.0% W/V. In embodiments, the $C_3$-$C_6$ alcohol (e.g., propylene glycol) is present in an amount from 3.6% W/V to 5.0% W/V. In embodiments, the $C_3$-$C_6$ alcohol (e.g., propylene glycol) is present in an amount from 3.8% W/V to 5.0% W/V. In embodiments, the $C_3$-$C_6$ alcohol (e.g., propylene glycol) is present in an amount from 4.0% W/V to 5.0% W/V. In embodiments, the $C_3$-$C_6$ alcohol (e.g., propylene glycol) is present in an amount from 4.2% W/V to 5.0% W/V. In embodiments, the $C_3$-$C_6$ alcohol (e.g., propylene glycol) is present in an amount from 4.4% W/V to 5.0% W/V.

In embodiments, the $C_3$-$C_6$ alcohol (e.g., propylene glycol) is present in an amount from about 2.0% W/V to about 5.0% W/V. In embodiments, the $C_3$-$C_6$ alcohol (e.g., propylene glycol) is present in an amount from about 2.0% W/V to about 4.8% W/V. In embodiments, the $C_3$-$C_6$ alcohol (e.g., propylene glycol) is present in an amount from about 2.0% W/V to about 4.6% W/V. In embodiments, the $C_3$-$C_6$ alcohol (e.g., propylene glycol) is present in an amount from about 2.0% W/V to about 4.4% W/V. In embodiments, the $C_3$-$C_6$ alcohol (e.g., propylene glycol) is present in an amount from about 2.0% W/V to about 4.2% W/V. In embodiments, the $C_3$-$C_6$ alcohol (e.g., propylene glycol) is present in an amount from about 2.0% W/V to about 4.0% W/V. In embodiments, the $C_3$-$C_6$ alcohol (e.g., propylene glycol) is present in an amount from about 2.0% W/V to about 3.8% W/V. In embodiments, the $C_3$-$C_6$ alcohol (e.g., propylene glycol) is present in an amount from about 2.0% W/V to about 3.6% W/V. In embodiments, the $C_3$-$C_6$ alcohol (e.g., propylene glycol) is present in an amount from about 2.0% W/V to about 3.4% W/V. In embodiments, the $C_3$-$C_6$ alcohol (e.g., propylene glycol) is present in an amount from about 2.0% W/V to about 3.2% W/V. In embodiments, the $C_3$-$C_6$ alcohol (e.g., propylene glycol) is present in an amount from about 2.0% W/V to about 3.0% W/V. In embodiments, the $C_3$-$C_6$ alcohol (e.g., propylene glycol) is present in an amount from about 2.0% W/V to about 2.8% W/V. In embodiments, the $C_3$-$C_6$ alcohol (e.g., propylene glycol) is present in an amount from about 2.0% W/V to about 2.6% W/V.

In embodiments, the $C_3$-$C_6$ alcohol (e.g., propylene glycol) is present in an amount from 2.0% W/V to 5.0% W/V. In embodiments, the $C_3$-$C_6$ alcohol (e.g., propylene glycol) is present in an amount from 2.0% W/V to 4.8% W/V. In embodiments, the $C_3$-$C_6$ alcohol (e.g., propylene glycol) is present in an amount from 2.0% W/V to 4.6% W/V. In embodiments, the $C_3$-$C_6$ alcohol (e.g., propylene glycol) is present in an amount from 2.0% W/V to 4.4% W/V. In embodiments, the $C_3$-$C_6$ alcohol (e.g., propylene glycol) is present in an amount from 2.0% W/V to 4.2% W/V. In embodiments, the $C_3$-$C_6$ alcohol (e.g., propylene glycol) is present in an amount from 2.0% W/V to 4.0% W/V. In embodiments, the $C_3$-$C_6$ alcohol (e.g., propylene glycol) is present in an amount from 2.0% W/V to 3.8% W/V. In embodiments, the $C_3$-$C_6$ alcohol (e.g., propylene glycol) is present in an amount from 2.0% W/V to 3.6% W/V. In embodiments, the $C_3$-$C_6$ alcohol (e.g., propylene glycol) is present in an amount from 2.0% W/V to 3.4% W/V. In embodiments, the $C_3$-$C_6$ alcohol (e.g., propylene glycol) is present in an amount from 2.0% W/V to 3.2% W/V. In embodiments, the $C_3$-$C_6$ alcohol (e.g., propylene glycol) is present in an amount from 2.0% W/V to 3.0% W/V. In embodiments, the $C_3$-$C_6$ alcohol (e.g., propylene glycol) is present in an amount from 2.0% W/V to 2.8% W/V. In embodiments, the $C_3$-$C_6$ alcohol (e.g., propylene glycol) is present in an amount from 2.0% W/V to 2.6% W/V.

In embodiments, the $C_3$-$C_6$ alcohol (e.g., propylene glycol) is present in an amount of about 2.0% W/V. In embodiments, the $C_3$-$C_6$ alcohol (e.g., propylene glycol) is present in an amount of about 2.2% W/V. In embodiments, the $C_3$-$C_6$ alcohol (e.g., propylene glycol) is present in an amount of about 2.4% W/V. In embodiments, the $C_3$-$C_6$ alcohol (e.g., propylene glycol) is present in an amount of about 2.6% W/V. In embodiments, the $C_3$-$C_6$ alcohol (e.g., propylene glycol) is present in an amount of about 2.8% W/V. In embodiments, the $C_3$-$C_6$ alcohol (e.g., propylene glycol) is present in an amount of about 3.0% W/V. In embodiments, the $C_3$-$C_6$ alcohol (e.g., propylene glycol) is present in an amount of about 3.2% W/V. In embodiments, the $C_3$-$C_6$ alcohol (e.g., propylene glycol) is present in an amount of about 3.4% W/V. In embodiments, the $C_3$-$C_6$ alcohol (e.g., propylene glycol) is present in an amount of about 3.6% W/V. In embodiments, the $C_3$-$C_6$ alcohol (e.g., propylene glycol) is present in an amount of about 3.8% W/V. In embodiments, the $C_3$-$C_6$ alcohol (e.g., propylene glycol) is present in an amount of about 4.0% W/V. In embodiments, the $C_3$-$C_6$ alcohol (e.g., propylene glycol) is present in an amount of about 4.2% W/V. In embodiments, the $C_3$-$C_6$ alcohol (e.g., propylene glycol) is present in an amount of about 4.4% W/V. In embodiments, the $C_3$-$C_6$ alcohol (e.g., propylene glycol) is present in an amount of about 4.6% W/V. In embodiments, the $C_3$-$C_6$ alcohol (e.g., propylene glycol) is present in an amount of about 4.8% W/V. In embodiments, the $C_3$-$C_6$ alcohol (e.g., propylene glycol) is present in an amount of about 5.0% W/V.

In embodiments, the $C_3$-$C_6$ alcohol (e.g., propylene glycol) is present in an amount of 2.0% W/V. In embodiments, the $C_3$-$C_6$ alcohol (e.g., propylene glycol) is present in an amount of 2.2% W/V. In embodiments, the $C_3$-$C_6$ alcohol (e.g., propylene glycol) is present in an amount of 2.4% W/V. In embodiments, the $C_3$-$C_6$ alcohol (e.g., propylene glycol) is present in an amount of 2.6% W/V. In embodiments, the $C_3$-$C_6$ alcohol (e.g., propylene glycol) is present in an amount of 2.8% W/V. In embodiments, the $C_3$-$C_6$ alcohol (e.g., propylene glycol) is present in an amount of 3.0% W/V. In embodiments, the $C_3$-$C_6$ alcohol (e.g., propylene glycol) is present in an amount of 3.2% W/V. In embodiments, the $C_3$-$C_6$ alcohol (e.g., propylene glycol) is present in an amount of 3.4% W/V. In embodiments, the $C_3$-$C_6$ alcohol (e.g., propylene glycol) is present in an amount of 3.6% W/V. In embodiments, the $C_3$-$C_6$ alcohol (e.g., propylene glycol) is present in an amount of 3.8% W/V. In embodiments, the $C_3$-$C_6$ alcohol (e.g., propylene glycol) is present in an amount of 4.0% W/V. In embodiments, the $C_3$-$C_6$ alcohol (e.g., propylene glycol) is present in an amount of 4.2% W/V. In embodiments, the $C_3$-$C_6$ alcohol (e.g., propylene glycol) is present in an amount of 4.4% W/V. In embodiments, the $C_3$-$C_6$ alcohol (e.g., propylene glycol) is present in an amount of 4.6% W/V. In embodiments, the $C_3$-$C_6$ alcohol (e.g., propylene glycol) is present in an amount of 4.8% W/V. In embodiments, the $C_3$-$C_6$ alcohol (e.g., propylene glycol) is present in an amount of 5.0% W/V.

In embodiments, the pharmaceutical formulation is a subcutaneous injection formulation. In embodiments, the pharmaceutical formulation consists of a subcutaneous injection formulation. In embodiments, the pharmaceutical formulation consists essentially of a subcutaneous injection formulation. In embodiments, the pharmaceutical formulation includes a subcutaneous injection formulation. In embodiments, the pharmaceutical formulation is an aqueous formulation. In embodiments, the pharmaceutical formulation is not a gel (e.g., at room temperature, at physiological temperatures, at normal human temperature, at about 37 degrees Celsius, at 37 degrees Celsius, at about 35 deg. C. to about 41.5 deg. C., at 35 deg C. to 41.5 deg C., at about 36.5 deg. C. to 37.5 deg C., at 36.5 deg. C. to 37.5 deg. C.).

In embodiments, the pharmaceutical formulation has an osmolality of less than about 400 milliosmoles/kg. In embodiments, the pharmaceutical formulation has an osmolality of less than about 380 milliosmoles/kg. In embodiments, the pharmaceutical formulation has an osmolality of less than about 360 milliosmoles/kg. In embodiments, the pharmaceutical formulation has an osmolality of less than about 340 milliosmoles/kg. In embodiments, the pharmaceutical formulation has an osmolality of less than about 320 milliosmoles/kg. In embodiments, the pharmaceutical formulation has an osmolality of less than about 300 milliosmoles/kg. In embodiments, the pharmaceutical formulation has an osmolality of less than about 280 milliosmoles/kg. In embodiments, the pharmaceutical formulation has an osmolality of less than about 260 milliosmoles/kg. In embodiments, the pharmaceutical formulation has an osmolality of less than about 240 milliosmoles/kg.

In embodiments, the pharmaceutical formulation has an osmolality of less than 400 milliosmoles/kg. In embodiments, the pharmaceutical formulation has an osmolality of less than 380 milliosmoles/kg. In embodiments, the pharmaceutical formulation has an osmolality of less than 360 milliosmoles/kg. In embodiments, the pharmaceutical formulation has an osmolality of less than 340 milliosmoles/kg. In embodiments, the pharmaceutical formulation has an osmolality of less than 320 milliosmoles/kg. In embodiments, the pharmaceutical formulation has an osmolality of less than 300 milliosmoles/kg. In embodiments, the pharmaceutical formulation has an osmolality of less than 280 milliosmoles/kg. In embodiments, the pharmaceutical formulation has an osmolality of less than 260 milliosmoles/kg. In embodiments, the pharmaceutical formulation has an osmolality of less than 240 milliosmoles/kg.

In embodiments, the pharmaceutical formulation has a pH of about 7 to about 8. In embodiments, the pharmaceutical formulation has a pH of about 7.1 to about 8. In embodiments, the pharmaceutical formulation has a pH of about 7.2 to about 8. In embodiments, the pharmaceutical formulation has a pH of about 7.3 to about 8. In embodiments, the pharmaceutical formulation has a pH of about 7.4 to about 8. In embodiments, the pharmaceutical formulation has a pH of about 7.5 to about 8. In embodiments, the pharmaceutical formulation has a pH of about 7.6 to about 8. In embodiments, the pharmaceutical formulation has a pH of about 7.7 to about 8. In embodiments, the pharmaceutical formulation has a pH of about 7.8 to about 8. In embodiments, the pharmaceutical formulation has a pH of about 7.9 to about 8. In embodiments, the pharmaceutical formulation has a pH of about 7 to about 7.9. In embodiments, the pharmaceutical formulation has a pH of about 7 to about 7.8. In embodiments, the pharmaceutical formulation has a pH of about 7 to about 7.7. In embodiments, the pharmaceutical formulation has a pH of about 7 to about 7.6. In embodiments, the pharmaceutical formulation has a pH of about 7 to about 7.5. In embodiments, the pharmaceutical formulation has a pH of about 7 to about 7.4. In embodiments, the pharmaceutical formulation has a pH of about 7 to about 7.3. In embodiments, the pharmaceutical formulation has a pH of about 7 to about 7.2. In embodiments, the pharmaceutical formulation has a pH of about 7 to about 7.1. In embodiments, the pharmaceutical formulation has a pH of about 7.1 to about 7.9. In embodiments, the pharmaceutical formulation has a pH of about 7.2 to about 7.8. In embodiments, the pharmaceutical formulation has a pH of about 7.3 to about 7.7. In embodiments, the pharmaceutical formulation has a pH of about 7.4 to about 7.6.

In embodiments, the pharmaceutical formulation has a pH of 7 to 8. In embodiments, the pharmaceutical formulation has a pH of 7.1 to 8. In embodiments, the pharmaceutical formulation has a pH of 7.2 to 8. In embodiments, the pharmaceutical formulation has a pH of 7.3 to 8. In embodiments, the pharmaceutical formulation has a pH of 7.4 to 8. In embodiments, the pharmaceutical formulation has a pH of 7.5 to 8. In embodiments, the pharmaceutical formulation has a pH of 7.6 to 8. In embodiments, the pharmaceutical formulation has a pH of 7.7 to 8. In embodiments, the pharmaceutical formulation has a pH of 7.8 to 8. In embodiments, the pharmaceutical formulation has a pH of 7.9 to 8. In embodiments, the pharmaceutical formulation has a pH of 7 to 7.9. In embodiments, the pharmaceutical formulation has a pH of 7 to 7.8. In embodiments, the pharmaceutical formulation has a pH of 7 to 7.7. In embodiments, the pharmaceutical formulation has a pH of 7 to 7.6. In embodiments, the pharmaceutical formulation has a pH of 7 to 7.5. In embodiments, the pharmaceutical formulation has a pH of 7 to 7.4. In embodiments, the pharmaceutical formulation has a pH of 7 to 7.3. In embodiments, the pharmaceutical formulation has a pH of 7 to 7.2. In embodiments, the pharmaceutical formulation has a pH of 7 to 7.1. In embodiments, the pharmaceutical formulation has a pH of 7.1 to 7.9. In embodiments, the pharmaceutical formulation has a pH of 7.2 to 7.8. In embodiments, the pharmaceutical formulation has a pH of 7.3 to 7.7. In embodiments, the pharmaceutical formulation has a pH of 7.4 to 7.6.

In embodiments, the pharmaceutical formulation has a pH of about 7.0. In embodiments, the pharmaceutical formulation has a pH of about 7.1. In embodiments, the pharmaceutical formulation has a pH of about 7.2. In embodiments, the pharmaceutical formulation has a pH of about 7.3. In embodiments, the pharmaceutical formulation has a pH of about 7.4. In embodiments, the pharmaceutical formulation has a pH of about 7.5. In embodiments, the pharmaceutical formulation has a pH of about 7.6. In embodiments, the pharmaceutical formulation has a pH of about 7.7. In embodiments, the pharmaceutical formulation has a pH of about 7.8. In embodiments, the pharmaceutical formulation has a pH of about 7.9. In embodiments, the pharmaceutical formulation has a pH of about 8.0.

In embodiments, the pharmaceutical formulation has a pH of 7.0. In embodiments, the pharmaceutical formulation has a pH of 7.1. In embodiments, the pharmaceutical formulation has a pH of 7.2. In embodiments, the pharmaceutical formulation has a pH of 7.3. In embodiments, the pharmaceutical formulation has a pH of 7.4. In embodiments, the pharmaceutical formulation has a pH of 7.5. In embodiments, the pharmaceutical formulation has a pH of 7.6. In embodiments, the pharmaceutical formulation has a pH of 7.7. In embodiments, the pharmaceutical formulation has a pH of 7.8. In embodiments, the pharmaceutical formulation has a pH of 7.9. In embodiments, the pharmaceutical formulation has a pH of 8.0.

In embodiments, the pharmaceutical formulation has a volume from about 0.2 cc to about 0.5 cc. In embodiments, the pharmaceutical formulation has a volume from about 0.25 cc to about 0.5 cc. In embodiments, the pharmaceutical formulation has a volume from about 0.3 cc to about 0.5 cc. In embodiments, the pharmaceutical formulation has a volume from about 0.35 cc to about 0.5 cc. In embodiments, the pharmaceutical formulation has a volume from about 0.4 cc to about 0.5 cc. In embodiments, the pharmaceutical formulation has a volume from about 0.45 cc to about 0.5 cc. In embodiments, the pharmaceutical formulation has a volume from about 0.2 cc to about 0.45 cc. In embodiments, the pharmaceutical formulation has a volume from about 0.2 cc to about 0.4 cc. In embodiments, the pharmaceutical formulation has a volume from about 0.2 cc to about 0.35 cc. In embodiments, the pharmaceutical formulation has a volume from about 0.2 cc to about 0.3 cc. In embodiments, the pharmaceutical formulation has a volume from about 0.2 cc to about 0.25 cc.

In embodiments, the pharmaceutical formulation has a volume from 0.2 cc to 0.5 cc. In embodiments, the pharmaceutical formulation has a volume from 0.25 cc to 0.5 cc. In embodiments, the pharmaceutical formulation has a volume from 0.3 cc to 0.5 cc. In embodiments, the pharmaceutical formulation has a volume from 0.35 cc to 0.5 cc. In embodiments, the pharmaceutical formulation has a volume from 0.4 cc to 0.5 cc. In embodiments, the pharmaceutical formulation has a volume from 0.45 cc to 0.5 cc. In embodiments, the pharmaceutical formulation has a volume from 0.2 cc to 0.45 cc. In embodiments, the pharmaceutical formulation has a volume from 0.2 cc to 0.4 cc. In embodiments, the pharmaceutical formulation has a volume from 0.2 cc to 0.35 cc. In embodiments, the pharmaceutical formulation has a volume from 0.2 cc to 0.3 cc. In embodiments, the pharmaceutical formulation has a volume from 0.2 cc to 0.25 cc.

In embodiments, the pharmaceutical formulation has a volume of about 0.20 cc. In embodiments, the pharmaceutical formulation has a volume of about 0.25 cc. In embodiments, the pharmaceutical formulation has a volume of about 0.30 cc. In embodiments, the pharmaceutical formulation has a volume of about 0.35 cc. In embodiments, the pharmaceutical formulation has a volume of about 0.40 cc. In embodiments, the pharmaceutical formulation has a volume of about 0.45 cc. In embodiments, the pharmaceutical formulation has a volume of about 0.50 cc.

In embodiments, the pharmaceutical formulation has a volume of 0.20 cc. In embodiments, the pharmaceutical formulation has a volume of 0.25 cc. In embodiments, the pharmaceutical formulation has a volume of 0.30 cc. In embodiments, the pharmaceutical formulation has a volume of 0.35 cc. In embodiments, the pharmaceutical formulation has a volume of 0.40 cc. In embodiments, the pharmaceutical formulation has a volume of 0.45 cc. In embodiments, the pharmaceutical formulation has a volume of 0.50 cc.

In embodiments, the pharmaceutical formulation further includes a buffer. In embodiments, the buffer is phosphate buffer (e.g., with Na+, K+, or both cations).

In embodiments, the pharmaceutical formulation includes water, polidocanol, buffer, propylene glycol, chloride and a monovalent metal ion selected from sodium, potassium or a mixture of sodium and potassium. In embodiments, the pharmaceutical formulation consists essentially of water, polidocanol, buffer, propylene glycol, chloride and a monovalent metal ion selected from sodium, potassium or a mixture of sodium and potassium. In embodiments, the pharmaceutical formulation consists of water, polidocanol, buffer, propylene glycol, chloride and a monovalent metal ion selected from sodium, potassium or a mixture of sodium and potassium.

In embodiments, the pharmaceutical formulation includes one or more of: buffers, diluents, lubricating agents, solubilizers, solvents; surfactants, penetration enhancers, polymers, dispersion agents, wetting agents, emulsifying and suspending agents, or preserving agents. Examples of dispersion agents include, but are not limited to, hyaluronidase and collagenase. In some embodiments, the dispersion agents, such as collagenase, are administered prior to the administration of the pharmaceutical formulation described herein.

In embodiments, the pharmaceutical formulation includes one or more of: acetylene glycol, ethylene glycol, diethylene glycol, triethylene glycol, propylene glycol, tetraethylene glycol, polyethylene glycol, dipropylene glycol, polypropylene glycol, hexylene glycol, thiodiglycol, glycerin, or 1,2, 6-hexanetriol.

In embodiments, the pharmaceutical formulation does not include a lipase or colipase.

In embodiments, the pharmaceutical formulation includes one or more of: anti-microbial agents, vasoconstrictors, anti-thrombotic agents, anti-coagulation agents, suds-depressants, anti-inflammatory agents, analgesics, dispersion agents, anti-dispersion agents, penetration enhancers, steroids, tranquilizers, muscle relaxants, or anti-diarrhea agents.

In embodiments, the pH of the pharmaceutical formulation may be maintained with the use of a buffer. Various buffers are known in the art and it is contemplated that any buffer having buffering capacity at the desired pH can be used in the formulations disclosed herein. In embodiments, the buffer is a phosphate buffer.

In embodiments, the water employed in the pharmaceutical formulation is sterile water. In still a further embodiment, a pharmaceutical formulation may include a preserving agent. In embodiments, the preserving agent in a pharmaceutical formulation described herein is benzyl alcohol. In embodiments, an effective amount of benzyl alcohol is about 0.9% w/v benzyl alcohol. In embodiments, an effective amount of benzyl alcohol is 0.9% w/v benzyl alcohol.

In an embodiment, the pharmaceutical formulation is split into a plurality of individual smaller pharmaceutical formulations which are separately administered to the fat cells. For example, the pharmaceutical formulation may be split into 5, 10, 15, 20, 25 or 30 separate pharmaceutical formulations and, in some cases, up to 50 separate pharmaceutical formulations. In embodiments, each such smaller pharmaceutical formulation is itself a pharmaceutical formulation and may have a volume described herein.

Provided herein is a solution to an unmet and long-felt need in the cosmetic and aesthetic industry for an emulsifying detergent formulation for reducing fat deposits that overcomes the shortcomings and failures of previous attempts in the field. In particular, provided herein are injectable formulations for treating or contacting fat cells, regional adipose tissue, regional adiposity, or regional fat accumulation. In embodiments, the formulations described herein include an effective amount, including for example a therapeutically or cosmetically effective amount, of polidocanol, polidocanol-like compound, or a pharmaceutically acceptable or cosmetically acceptable salt or other suitable form thereof and a liquid carrier including aqueous carriers; wherein the polidocanol, polidocanol-like compound and the liquid carrier are formulated for injection into a layer of fat, including subcutaneous fat, in the individual in need thereof. In embodiment, the formulations do not include a lipase. In embodiment, the formulations do not include a colipase.

Figure 2:
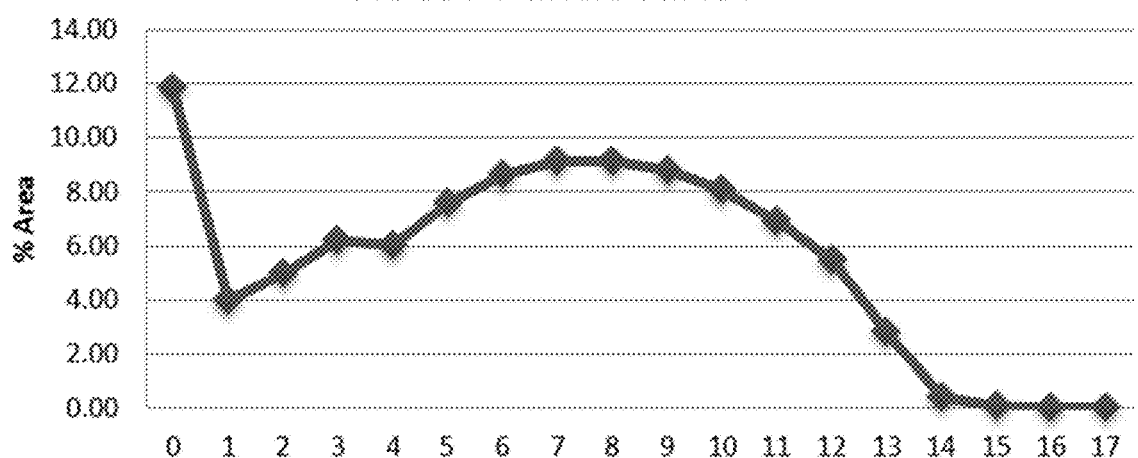
FIG. 2. percentage of each peak in the polidocanol formulation produced by reacting 1 mole of C12 alcohol with 9 moles of ethylene oxide in the presence of a potassium hydroxide catalyst.

In embodiments, the polidocanol produced herein results in a mixture of unbranched, saturated C12 primary alcohol ethoxylate homologues having a range of ethoxide units (see, e.g. FIGS. 1 and 2). For example, HPLC characterization of embodiments of product polidoconal synthesized herein results in approximately 15 peaks associated with varying numbers of ethoxide units (FIG. 1). In the polidoconal product characterized in FIG. 1, for example, no single peak makes up more than 10% of the total mixture. The average ethoxylation number of the polidoconal characterized in FIG. 1 (and provided herein) is 6-7 and the average molecular weight is approximately 493 g/mol.

In embodiments, potassium hydroxide is used as the catalyst to produce polidocanol from ethylene oxide (e.g. 9 moles) and dodecanol (e.g. 1 mole).

Polidocanol products with different ranges or percentages of ethoxylate homologues may be produced using different catalysts (e.g. different metal oxide catalysts). See e.g. Van O S, N. M., *Nonionic Surfactants—Organic Chemistry*, Marcel Dekker Inc., New York, 1998, p. 101 at FIG. 4A-C. In embodiments, the polidocanol includes fewer than 15 major peaks (e.g. 10 or less) as shown by HPLC characterization. The polidocanol may include about 7 to about 11 ethoxylate units.

In embodiments, the product polidocanol includes alkyl ethoxylate homologue mixtures containing a high proportion of detergent/surfactant homologues per gram of mixture produced (e.g., by the methods provided herein).

In embodiments, polidocanol is formulated with a co-solvent. The co-solvent may be propylene glycol.

In embodiments, the intravascular formulation of polidocanol contains ethanol at approximately 5% to improve formulation stability (particularly at lower temperatures) and to reduce foaming. Ethanol is suitable for intravascular administration due to its rapid dilution by the blood. However, for subcutaneous administration, where the injected formulation resides longer at the administration site, ethanol is not ideal. Ethanol is irritating when administered subcutaneously and can cause burning, swelling, redness, and skin discoloration secondary to inflammation. In addition, ethanol is generally toxic to a variety of tissues and may limit the selective effect of polidocanol on subcutaneous fat tissue, resulting in more complications.

Formulations including Compounds of Formula I, Formula II, or polidocanol

In an aspect is provided an injectable formulation for treating fat, regional fat, adipose tissue, regional adiposity, or regional fat accumulation including: an effective amount, including for example a therapeutically or cosmetically effective amount, of the compound of Formula I

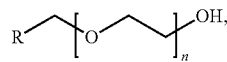

or a pharmaceutically acceptable or cosmetically acceptable salt or other suitable form thereof, and wherein n=2 to 55; R is a saturated, linear $C_7$-$C_{24}$ hydrocarbon (alkyl), or an unsaturated, linear $C_7$-$C_{24}$ hydrocarbon; and a liquid carrier.

In embodiments, the compound of Formula I, or a pharmaceutically acceptable or cosmetically acceptable salt or other suitable form thereof and the liquid carrier are formulated for injection into a layer of subcutaneous fat in a human in need. In embodiments, the injectable formulation is formulated for subcutaneous injection.

In embodiments, R is a saturated, linear $C_7$-$C_{24}$ hydrocarbon. In some embodiments, R is a saturated, linear $C_7$-$C_{16}$ hydrocarbon, and in some embodiments R is a saturated, linear $C_7$-$C_{12}$ hydrocarbon. In some embodiments, R is a saturated, linear $C_{12}$-$C_{18}$ hydrocarbon. In an embodiment, R is a saturated, linear $C_{18}$-$C_{24}$ hydrocarbon. In certain embodiments, R is a saturated, linear $C_7$-$C_{24}$ hydrocarbon. In some embodiments, R is a saturated, linear $C_7$-$C_{12}$ hydrocarbon. In some embodiments, R is a saturated, linear $C_{12}$-$C_{18}$ hydrocarbon. In an embodiment, R is a saturated, linear $C_{18}$-$C_{24}$ hydrocarbon.

In embodiments, R is an unsaturated, linear $C_7$-$C_{24}$ hydrocarbon. In some embodiments, R is an unsaturated, linear $C_7$-$C_{12}$ hydrocarbon. In an embodiment, R is an unsaturated, linear $C_{12}$-$C_{18}$ hydrocarbon. In some embodiments, R is an unsaturated, linear $C_{18}$-$C_{24}$ hydrocarbon. In certain embodiments, the unsaturated, linear hydrocarbon includes at least one alkene moiety. In some embodiments, the unsaturated, linear hydrocarbon includes at least one alkene moiety of cis configuration. In an embodiment, R is an unsaturated, linear $C_7$-$C_{24}$ hydrocarbon. In some embodiments, R is an unsaturated, linear $C_7$-$C_{12}$ hydrocarbon. In an embodiment, R is an unsaturated, linear $C_{12}$-$C_{18}$ hydrocarbon. In some embodiments, R is an unsaturated, linear $C_{18}$-$C_{24}$ hydrocarbon. In certain embodiments, the unsaturated, linear hydrocarbon includes at least one alkene moiety. In certain embodiments, the unsaturated, linear hydrocarbon includes at least one alkene moiety of trans configuration. In some embodiments, the unsaturated, linear hydrocarbon includes at least one alkyne moiety.

In embodiments, the injectable formulation is for treating fat. In embodiments, the injectable formulation is for treating regional fat. In embodiments, the injectable formulation is for treating adipose tissue. In embodiments, the injectable formulation is for treating regional adiposity. In embodiments, the injectable formulation is for treating regional fat accumulation.

In embodiments, the injectable formulation includes an effective amount, including for example a therapeutically or cosmetically effective amount, of the compound of Formula I

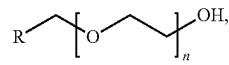

wherein R is a saturated or unsaturated, linear $C_{11}$ or $C_{12}$ hydrocarbon. In certain embodiments, the unsaturated, linear hydrocarbon includes at least one alkene moiety. In some embodiments, the unsaturated, linear hydrocarbon includes at least one alkene moiety of cis configuration. In some embodiments, the unsaturated, linear hydrocarbon includes at least one alkene moiety of trans configuration. In certain embodiments, the unsaturated, linear hydrocarbon includes at least one alkyne moiety.

In embodiments, the injectable formulation includes an effective amount, including for example a therapeutically or cosmetically effective amount, of the compound of Formula I, wherein n is 5 to 32. In some embodiments, n is 7 to 21. In certain embodiments, n is 7. In some embodiments, n is 9. In an embodiment, n is 11. In embodiments, n is 5 to 32. In certain embodiments, n is 7 to 21. In a specific embodiments, R is a saturated linear $C_{12}$ hydrocarbon and n is 9.

Formula II

Provided below is the chemical structure of Formula II, wherein n is 2 to 55 (e.g. approximately 9).

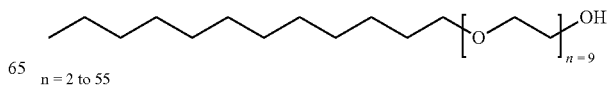

n = 2 to 55

In certain embodiments of the formulations described herein, provided is a compound of Formula II wherein n is from 2 to 55. Where n is approximately 9, the compound of Formula II may be referred to herein as a polidocanol. In some embodiments, n is selected from the range of 5 to 32 (e.g. 9). In certain embodiments, n is selected from the range of 7 to 21. In embodiments, n is 7 to 15. In embodiments, n is 7 to 14. In certain embodiments, n=7. In certain embodiments, n=8. In certain embodiments, n=9. In certain embodiments, n=10. In certain embodiments, n=11. In certain embodiments, n=12.

In an aspect, provided herein are injectable formulations for treating or contacting fat tissue, regional adipose tissue, regional adiposity, or regional fat accumulation, the formulations provide an effective amount, including for example a therapeutically or cosmetically effective amount, of a compound of Formula II or a pharmaceutically acceptable or cosmetically acceptable salt or other suitable form thereof, and a liquid carrier.

In embodiments, the compound or a pharmaceutically acceptable or cosmetically acceptable salt or other suitable form thereof and the liquid carrier are formulated for injection into a layer of subcutaneous fat in a human in need. In embodiments, the injectable formulation is formulated for subcutaneous injection.

In embodiments, the polidocanol is present in an amount of about 0.1%-10% W/V or about 0.1%-5% W/V. In some embodiments, the polidocanol is present in an amount of about 0.5%-3% W/V, or less than about 0.5% W/V, or less than about 1% W/V, or less than about 2% W/V, or less than about 3% W/V, or less than about 4% W/V, or less than about 5% W/V, or less than about 10% W/V. In further or additional embodiments, the polidocanol is present in an amount that is greater than 1% W/V, greater than 1.5% W/V, greater than 2% W/V, greater than 2.5% W/V, greater than 3% W/V, greater than 4% W/V, greater than 5% W/V, greater than 6% W/V, or is about 10% W/V. In embodiments, the polidocanol is present in an amount between about 0.75% and about 1.50% W/V. In embodiments, the polidocanol is present in an amount between about 0.80% and about 1.45% W/V. In embodiments, the polidocanol is present in an amount between about 0.85% and about 1.40% W/V. In embodiments, the polidocanol is present in an amount between about 0.90% and about 1.35% W/V. In embodiments, the polidocanol is present in an amount between about 0.95% and about 1.30% W/V. In embodiments, the polidocanol is present in an amount between about 1.00% and about 1.25% W/V. In embodiments, the polidocanol is present in an amount between about 1.05% and about 1.20% W/V. In embodiments, the polidocanol is present in an amount between about 1.10% and about 1.15% W/V. In embodiments, the polidocanol is present in an amount between about 1.00% and about 1.30% W/V. In embodiments, the polidocanol is present in an amount between about 1.00% and about 1.35% W/V. In embodiments, the polidocanol is present in an amount between about 1.00% and about 1.40% W/V. In embodiments, the polidocanol is present in an amount between about 1.00% and about 1.45% W/V. In embodiments, the polidocanol is present in an amount between about 1.00% and about 1.50% W/V. In embodiments, the polidocanol is present in an amount of about 1.00% W/V. In embodiments, the polidocanol is present in an amount of about 1.05% W/V. In embodiments, the polidocanol is present in an amount of about 1.10% W/V. In embodiments, the polidocanol is present in an amount of about 1.15% W/V. In embodiments, the polidocanol is present in an amount of about 1.20% W/V. In embodiments, the polidocanol is present in an amount of about 1.25% W/V. In embodiments, the polidocanol is present in an amount of about 1.30% W/V. In embodiments, the polidocanol is present in an amount of about 1.35% W/V. In embodiments, the polidocanol is present in an amount of about 1.40% W/V. In embodiments, the polidocanol is present in an amount of about 1.45% W/V. In embodiments, the polidocanol is present in an amount of about 1.50% W/V. In embodiments, the polidocanol is present in an amount between 0.75% and 1.50% W/V. In embodiments, the polidocanol is present in an amount between 0.80% and 1.45% W/V. In embodiments, the polidocanol is present in an amount between 0.85% and 1.40% W/V. In embodiments, the polidocanol is present in an amount between 0.90% and 1.35% W/V. In embodiments, the polidocanol is present in an amount between 0.95% and 1.30% W/V. In embodiments, the polidocanol is present in an amount between 1.00% and 1.25% W/V. In embodiments, the polidocanol is present in an amount between 1.05% and 1.20% W/V. In embodiments, the polidocanol is present in an amount between 1.10% and 1.15% W/V. In embodiments, the polidocanol is present in an amount between 1.00% and 1.30% W/V. In embodiments, the polidocanol is present in an amount between 1.00% and 1.35% W/V. In embodiments, the polidocanol is present in an amount between 1.00% and 1.40% W/V. In embodiments, the polidocanol is present in an amount between 1.00% and 1.45% W/V. In embodiments, the polidocanol is present in an amount between 1.00% and 1.50% W/V. In embodiments, the polidocanol is present in an amount of about 1.00% W/V. In embodiments, the polidocanol is present in an amount of about 1.05% W/V. In embodiments, the polidocanol is present in an amount of about 1.10% W/V. In embodiments, the polidocanol is present in an amount of about 1.15% W/V. In embodiments, the polidocanol is present in an amount of about 1.20% W/V. In embodiments, the polidocanol is present in an amount of about 1.25% W/V. In embodiments, the polidocanol is present in an amount of about 1.30% W/V. In embodiments, the polidocanol is present in an amount of about 1.35% W/V. In embodiments, the polidocanol is present in an amount of about 1.40% W/V. In embodiments, the polidocanol is present in an amount of about 1.45% W/V. In embodiments, the polidocanol is present in an amount of about 1.50% W/V.

In embodiments, the compound of Formula II is present in an amount of about 0.1%-10% W/V or about 0.1%-5% W/V. In some embodiments, the compound of Formula II is present in an amount of about 0.5%-3% W/V, or less than about 0.5% W/V, or less than about 1% W/V, or less than about 2% W/V, or less than about 3% W/V, or less than about 4% W/V, or less than about 5% W/V, or less than about 10% W/V. In further or additional embodiments, the compound of Formula II is present in an amount that is greater than 1% W/V, greater than 1.5% W/V, greater than 2% W/V, greater than 2.5% W/V, greater than 3% W/V, greater than 4% W/V, greater than 5% W/V, greater than 6% W/V, or is about 10% W/V. In embodiments, the compound of Formula II is present in an amount between about 0.75% and about 1.50% W/V. In embodiments, the compound of Formula II is present in an amount between about 0.80% and about 1.45% W/V. In embodiments, the compound of Formula II is present in an amount between about 0.85% and about 1.40% W/V. In embodiments, the compound of Formula II is present in an amount between about 0.90% and about 1.35% W/V. In embodiments, the compound of Formula II is present in an amount between about 0.95% and about 1.30% W/V. In embodiments, the compound of Formula II is present in an amount between about 1.00% and about 1.25% W/V. In embodiments, the compound of Formula II is present in an amount between about 1.05% and about 1.20% W/V. In embodiments, the compound of Formula II is present in an amount between about 1.10% and about 1.15% W/V. In embodiments, the compound of Formula II is present in an amount between about 1.00% and about 1.30% W/V.

In embodiments, the compound of Formula II is present in an amount between about 1.00% and about 1.35% W/V. In embodiments, the compound of Formula II is present in an amount between about 1.00% and about 1.40% W/V. In embodiments, the compound of Formula II is present in an amount between about 1.00% and about 1.45% W/V. In embodiments, the compound of Formula II is present in an amount between about 1.00% and about 1.50% W/V. In embodiments, the compound of Formula II is present in an amount of about 1.00% W/V. In embodiments, the compound of Formula II is present in an amount of about 1.05% W/V. In embodiments, the compound of Formula II is present in an amount of about 1.10% W/V. In embodiments, the compound of Formula II is present in an amount of about 1.15% W/V. In embodiments, the compound of Formula II is present in an amount of about 1.20% W/V. In embodiments, the compound of Formula II is present in an amount of about 1.25% W/V. In embodiments, the compound of Formula II is present in an amount of about 1.30% W/V. In embodiments, the compound of Formula II is present in an amount of about 1.35% W/V. In embodiments, the compound of Formula II is present in an amount of about 1.40% W/V. In embodiments, the compound of Formula II is present in an amount of about 1.45% W/V. In embodiments, the compound of Formula II is present in an amount of about 1.50% W/V. In embodiments, the compound of Formula II is present in an amount between 0.75% and 1.50% W/V. In embodiments, the compound of Formula II is present in an amount between 0.80% and 1.45% W/V. In embodiments, the compound of Formula II is present in an amount between 0.85% and 1.40% W/V. In embodiments, the compound of Formula II is present in an amount between 0.90% and 1.35% W/V. In embodiments, the compound of Formula II is present in an amount between 0.95% and 1.30% W/V. In embodiments, the compound of Formula II is present in an amount between 1.00% and 1.25% W/V. In embodiments, the compound of Formula II is present in an amount between 1.05% and 1.20% W/V. In embodiments, the compound of Formula II is present in an amount between 1.10% and 1.15% W/V. In embodiments, the compound of Formula II is present in an amount between 1.00% and 1.30% W/V. In embodiments, the compound of Formula II is present in an amount between 1.00% and 1.35% W/V. In embodiments, the compound of Formula II is present in an amount between 1.00% and 1.40% W/V. In embodiments, the compound of Formula II is present in an amount between 1.00% and 1.45% W/V. In embodiments, the compound of Formula II is present in an amount between 1.00% and 1.50% W/V. In embodiments, the compound of Formula II is present in an amount of about 1.00% W/V. In embodiments, the compound of Formula II is present in an amount of about 1.05% W/V. In embodiments, the compound of Formula II is present in an amount of about 1.10% W/V. In embodiments, the compound of Formula II is present in an amount of about 1.15% W/V. In embodiments, the compound of Formula II is present in an amount of about 1.20% W/V. In embodiments, the compound of Formula II is present in an amount of about 1.25% W/V. In embodiments, the compound of Formula II is present in an amount of about 1.30% W/V. In embodiments, the compound of Formula II is present in an amount of about 1.35% W/V. In embodiments, the compound of Formula II is present in an amount of about 1.40% W/V. In embodiments, the compound of Formula II is present in an amount of about 1.45% W/V. In embodiments, the compound of Formula II is present in an amount of about 1.50% W/V.

In embodiments, the compound of Formula I is present in an amount of about 0.1%-10% W/V or about 0.1%-5% W/V. In some embodiments, the compound of Formula I is present in an amount of about 0.5%-3% W/V, or less than about 0.5% W/V, or less than about 1% W/V, or less than about 2% W/V, or less than about 3% W/V, or less than about 4% W/V, or less than about 5% W/V, or less than about 10% W/V. In further or additional embodiments, the compound of Formula I is present in an amount that is greater than 1% W/V, greater than 1.5% W/V, greater than 2% W/V, greater than 2.5% W/V, greater than 3% W/V, greater than 4% W/V, greater than 5% W/V, greater than 6% W/V, or is about 10% W/V. In embodiments, the compound of Formula I is present in an amount between about 0.75% and about 1.50% W/V. In embodiments, the compound of Formula I is present in an amount between about 0.80% and about 1.45% W/V. In embodiments, the compound of Formula I is present in an amount between about 0.85% and about 1.40% W/V. In embodiments, the compound of Formula I is present in an amount between about 0.90% and about 1.35% W/V. In embodiments, the compound of Formula I is present in an amount between about 0.95% and about 1.30% W/V. In embodiments, the compound of Formula I is present in an amount between about 1.00% and about 1.25% W/V. In embodiments, the compound of Formula I is present in an amount between about 1.05% and about 1.20% W/V. In embodiments, the compound of Formula I is present in an amount between about 1.10% and about 1.15% W/V. In embodiments, the compound of Formula I is present in an amount between about 1.00% and about 1.30% W/V. In embodiments, the compound of Formula I is present in an amount between about 1.00% and about 1.35% W/V. In embodiments, the compound of Formula I is present in an amount between about 1.00% and about 1.40% W/V. In embodiments, the compound of Formula I is present in an amount between about 1.00% and about 1.45% W/V. In embodiments, the compound of Formula I is present in an amount between about 1.00% and about 1.50% W/V. In embodiments, the compound of Formula I is present in an amount of about 1.00% W/V. In embodiments, the compound of Formula I is present in an amount of about 1.05% W/V. In embodiments, the compound of Formula I is present in an amount of about 1.10% W/V. In embodiments, the compound of Formula I is present in an amount of about 1.15% W/V. In embodiments, the compound of Formula I is present in an amount of about 1.20% W/V. In embodiments, the compound of Formula I is present in an amount of about 1.25% W/V. In embodiments, the compound of Formula I is present in an amount of about 1.30% W/V. In embodiments, the compound of Formula I is present in an amount of about 1.35% W/V. In embodiments, the compound of Formula I is present in an amount of about 1.40% W/V. In embodiments, the compound of Formula I is present in an amount of about 1.45% W/V. In embodiments, the compound of Formula I is present in an amount of about 1.50% W/V. In embodiments, the compound of Formula I is present in an amount between 0.75% and 1.50% W/V. In embodiments, the compound of Formula I is present in an amount between 0.80% and 1.45% W/V. In embodiments, the compound of Formula I is present in an amount between 0.85% and 1.40% W/V. In embodiments, the compound of Formula I is present in an amount between 0.90% and 1.35% W/V. In embodiments, the compound of Formula I is present in an amount between 0.95% and 1.30% W/V. In embodiments, the compound of Formula I is present in an amount between 1.00% and 1.25% W/V. In embodiments, the compound of Formula I is present in an amount between 1.05% and 1.20% W/V. In embodiments, the compound of Formula I is present in an amount between 1.10% and 1.15% W/V. In embodiments, the compound of Formula I is present in an amount between 1.00% and 1.30% W/V. In embodiments, the compound of Formula I is present in an amount between 1.00% and 1.35% W/V. In embodiments, the compound of Formula I is present in an amount between 1.00% and 1.40% W/V. In embodiments, the compound of Formula I is present in an amount between 1.00% and 1.45% W/V. In embodiments, the compound of Formula I is present in an amount between 1.00% and 1.50% W/V. In embodiments, the compound of Formula I is present in an amount of about 1.00% W/V. In embodiments, the compound of Formula I is present in an amount of about 1.05% W/V. In embodiments, the compound of Formula I is present in an amount of about 1.10% W/V. In embodiments, the compound of Formula I is present in an amount of about 1.15% W/V. In embodiments, the compound of Formula I is present in an amount of about 1.20% W/V. In embodiments, the compound of Formula I is present in an amount of about 1.25% W/V. In embodiments, the compound of Formula I is present in an amount of about 1.30% W/V. In embodiments, the compound of Formula I is present in an amount of about 1.35% W/V. In embodiments, the compound of Formula I is present in an amount of about 1.40% W/V. In embodiments, the compound of Formula I is present in an amount of about 1.45% W/V. In embodiments, the compound of Formula I is present in an amount of about 1.50% W/V.

While not wishing to be bound by theory, in embodiments, polidocanol and related compounds of Formula I or Formula II preferentially lyse fat cells while leaving surrounding tissue largely unaffected (e.g., unlysed or less lysed in comparison to the lysis of fat cells (e.g., percentage of lysed cells, number of lysed cells, degree of lysis of a tissue or cell population)). Accordingly, in embodiments, the formulations described herein provide selective reduction (e.g., reduction of fat cells or tissue in a greater amount than adjacent non-fat cells or tissue) of regional and/or subcutaneous accumulations of adipose tissue and adipocytes, including cellulite. In some embodiments, the compositions described herein are useful for treating cellulitic fat accumulation and/or lipomas.

While not wishing to be bound by theory, in embodiments, polidocanol and related compounds of Formula I or Formula II preferentially lyse fat cells while leaving surrounding tissue largely unaffected (e.g., unlysed or less lysed in comparison to the lysis of fat cells (e.g., percentage of lysed cells, number of lysed cells, degree of lysis of a tissue or cell population)). Accordingly, in some embodiments, the formulations described herein provide selective reduction (e.g., reduction of fat cells or tissue in a greater amount than adjacent non-fat cells or tissue) of regional and/or subcutaneous accumulations of adipose tissue and adipocytes, including cellulite, through subcutaneous administration of polidocanol, or polidocanol-like compounds of Formula I or Formula II. In some embodiments, the compositions described herein are useful for treating cellulitic fat accumulation and/or lipomas.

In certain embodiments, provided is a formulation or composition including a compound of Formula I or Formula II (e.g., polidocanol) that provides one or more of the following: (a) a critical micelle concentration ("CMC") of less than about 5 millimolar; (b) an HLB value of from about 10 to about 15; and (c) is non-ionic. In some embodiments, these formulations are used for contacting fat tissue, abdominal fat accumulation, regional adiposity, excess submental fat, and exophthalmous (e.g., due to thyroid eye disease), and/or for emulsifying, necrotizing, lysing or destroying one or more adipose cells while, in certain situations, leaving surrounding tissue largely unaffected (e.g., unlysed or less lysed in comparison to the lysis of fat cells (e.g., percentage of lysed cells, number of lysed cells, degree of lysis of a tissue or cell population). In certain embodiments, the compound is polidocanol.

In embodiments, the polidocanol is present in an amount of about 0.1%-10% W/V or about 0.1%-5% W/V. In some embodiments, the polidocanol is present in an amount of about 0.5%-3% W/V, or less than about 0.5% W/V, or less than about 1% W/V, or less than about 2% W/V, or less than about 3% W/V, or less than about 4% W/V, or less than about 5% W/V, or less than about 10% W/V. In further or additional embodiments, the polidocanol is present in an amount that is greater than 1% W/V, greater than 1.5% W/V, greater than 2% W/V, greater than 2.5% W/V, greater than 3% W/V, greater than 4% W/V, greater than 5% W/V, greater than 6% W/V, or is about 10% W/V. In embodiments, the polidocanol is present in an amount between about 0.75% and about 1.50% W/V. In embodiments, the polidocanol is present in an amount between about 0.80% and about 1.45% W/V. In embodiments, the polidocanol is present in an amount between about 0.85% and about 1.40% W/V. In embodiments, the polidocanol is present in an amount between about 0.90% and about 1.35% W/V. In embodiments, the polidocanol is present in an amount between about 0.95% and about 1.30% W/V. In embodiments, the polidocanol is present in an amount between about 1.00% and about 1.25% W/V. In embodiments, the polidocanol is present in an amount between about 1.05% and about 1.20% W/V. In embodiments, the polidocanol is present in an amount between about 1.10% and about 1.15% W/V. In embodiments, the polidocanol is present in an amount between about 1.00% and about 1.30% W/V. In embodiments, the polidocanol is present in an amount between about 1.00% and about 1.35% W/V. In embodiments, the polidocanol is present in an amount between about 1.00% and about 1.40% W/V. In embodiments, the polidocanol is present in an amount between about 1.00% and about 1.45% W/V. In embodiments, the polidocanol is present in an amount between about 1.00% and about 1.50% W/V. In embodiments, the polidocanol is present in an amount of about 1.00% W/V. In embodiments, the polidocanol is present in an amount of about 1.05% W/V. In embodiments, the polidocanol is present in an amount of about 1.10% W/V. In embodiments, the polidocanol is present in an amount of about 1.15% W/V. In embodiments, the polidocanol is present in an amount of about 1.20% W/V. In embodiments, the polidocanol is present in an amount of about 1.25% W/V. In embodiments, the polidocanol is present in an amount of about 1.30% W/V. In embodiments, the polidocanol is present in an amount of about to 1.35% W/V. In embodiments, the polidocanol is present in an amount of about 1.40% W/V. In embodiments, the polidocanol is present in an amount of about 1.45% W/V. In embodiments, the polidocanol is present in an amount of about 1.50% W/V. In embodiments, the polidocanol is present in an amount between 0.75% and 1.50% W/V. In embodiments, the polidocanol is present in an amount between 0.80% and 1.45% W/V. In embodiments, the polidocanol is present in an amount between 0.85% and 1.40% W/V. In embodiments, the polidocanol is present in an amount between 0.90% and 1.35% W/V. In embodiments, the polidocanol is present in an amount between 0.95% and 1.30% W/V. In embodiments, the polidocanol is present in an amount between 1.00% and 1.25% W/V. In embodiments, the polidocanol is present in an amount between 1.05% and 1.20% W/V. In embodiments, the polidocanol is present in an amount between 1.10% and 1.15% W/V. In embodiments, the polidocanol is present in an amount between 1.00% and 1.30% W/V. In embodiments, the polidocanol is present in an amount between 1.00% and 1.35% W/V. In embodiments, the polidocanol is present in an amount between 1.00% and 1.40% W/V. In embodiments, the polidocanol is present in an amount between 1.00% and 1.45% W/V. In embodiments, the polidocanol is present in an amount between 1.00% and 1.50% W/V. In embodiments, the polidocanol is present in an amount of about 1.00% W/V. In embodiments, the polidocanol is present in an amount of about 1.05% W/V. In embodiments, the polidocanol is present in an amount of about 1.10% W/V. In embodiments, the polidocanol is present in an amount of about 1.15% W/V. In embodiments, the polidocanol is present in an amount of about 1.20% W/V. In embodiments, the polidocanol is present in an amount of about 1.25% W/V. In embodiments, the polidocanol is present in an amount of about 1.30% W/V. In embodiments, the polidocanol is present in an amount of about 1.35% W/V. In embodiments, the polidocanol is present in an amount of about 1.40% W/V. In embodiments, the polidocanol is present in an amount of about 1.45% W/V. In embodiments, the polidocanol is present in an amount of about 1.50% W/V.

Critical Micelle Concentration ("CMC")

In some embodiments, provided is a formulation including a compound of Formula I or Formula II (e.g., polidocanol) that provides a critical micelle concentration ("CMC") of less than 5 millimolar, less about 4 millimolar, less than about 3 millimolar, less than about 2 millimolar, less than about 1 millimolar, less than about 0.9 millimolar, less than about 0.7 millimolar, less than about 0.5 millimolar, or less than about 0.1 millimolar. In some embodiments, the CMC is from about 0.01 to about 10 millimolar. In some embodiments, the CMC is from 0.5 to about 1.0. In further or additional embodiments, the CMC is from 0.7 to 0.8. In some embodiments, provided is formulation that is used for contacting fat tissue, abdominal fat accumulation, regional adiposity, excess sub-mental fat, and exophthalmous (e.g., due to thyroid eye disease), and/or for emulsifying, necrotizing, lysing or destroying one or more adipose cells while, in certain situations, leaving surrounding tissue largely unaffected (e.g., unlysed or less lysed in comparison to the lysis of fat cells (e.g., percentage of lysed cells, number of lysed cells, degree of lysis of a tissue or cell population). In certain embodiments, the compound is polidocanol. In some embodiments, the formulations provided herein form a micelle after administration to tissue, including subcutaneous adiposity tissue.

Hydrophilic-Lipophilic Balance ("HLB")

In some embodiments, provided is a formulation including a polidocanol of Formula I or Formula II (e.g., polidocanol) that has an HLB value of from about 10 to about 15. Changing the nature of the hydrophobic hydrocarbon alkyl tail of a compound of Formulas I or II such as increasing or decreasing the length or the degree of saturation can affect the HLB. The length of the hydrophilic head (e.g., a polyether) of a compound of Formulas I or II can also affect the HLB. For example, too many polyethers can cause the compound to be too water soluble and act like ionic detergent and have unwanted effects on healthy tissue (e.g., adjacent, surrounding, non-fat tissue). On the other hand, too few polyether groups the compound will render the compound not soluble or immiscible (e.g., crystallization, aggregation) in aqueous solution causing formulation and manufacture complications (e.g., non-uniform formulation), and in turn decreased effectiveness (e.g., non-uniform adipose reduction over an area or non-uniform reduction of adipocytes over an area, patchiness of fat reduction). Thus, the disclosed n values of the compounds of Formulas I and II as described herein are desirable.

In some embodiments, provided is a formulation including a compound of Formula I or Formula II (e.g., polidocanol) that has an HLB value of from about 11-14, of about 12-13, of about 12.5-13.5, of about 11, of about 12, about 13, of about 14, or of about 15. In some embodiments, these formulations are used for contacting fat tissue, abdominal fat accumulation, regional adiposity, excess sub-mental fat, and exophthalmous (e.g., due to thyroid eye disease), and/or for emulsifying, necrotizing, lysing or destroying one or more adipose cells while, in certain applications, leaving surrounding tissue largely unaffected (e.g., unlysed or less lysed in comparison to the lysis of fat cells (e.g., percentage of lysed cells, number of lysed cells, degree of lysis of a tissue or cell population). In certain embodiments, the compound is polidocanol.

As described above, the polidocanol may be a mixture of C12 alkyl ethoxylate homologues. In embodiments, about 10% to about 90% of the mixture has a HLB from about 10 to about 15. In embodiments, about 20% to about 80% of the mixture has a HLB from about 10 to about 15. In embodiments, about 30% to about 70% of the mixture has a HLB from about 10 to about 15. In embodiments, about 40% to about 60% of the mixture has a HLB from about 10 to about 15. In embodiments, about 50% of the mixture has a HLB from about 10 to about 15. In embodiments, about 10% to about 20% of the mixture has a HLB from about 10 to about 15. In embodiments, about 15% of the mixture has an HLB from about 10 to about 15. In embodiments, about 5% to about 20% of the mixture has an HLB below about 10. In embodiments, about 10% to about 20% of the mixture has an HLB below 10. In embodiments, about 10% of the mixture has an HLB below about 10. In embodiments, about 20% of the mixture has an HLB below about 10. In embodiments, about 20% of the mixture has an HLB below about 10. In embodiments, about 1% to about 20% of the mixture has an HLB above about 10. In embodiments, about 1% to about 15% of the mixture has an HLB above 10. In embodiments, about 1% to about 10% of the mixture has an HLB above about 10. In embodiments, about 1% to about 5% of the mixture has an HLB above about 10. In embodiments, about 10% of the mixture has an HLB above about 10.

As described above, the polidocanol may a mixture of C12 alkyl ethoxylate homologues. In embodiments, 10% to 90% of the mixture has a HLB from 10 to 15. In embodiments, 20% to 80% of the mixture has a HLB from 10 to 15. In embodiments, 30% to 70% of the mixture has a HLB from 10 to 15. In embodiments, 40% to 60% of the mixture has a HLB from 10 to 15. In embodiments, 50% of the mixture has a HLB from 10 to 15. In embodiments, 10% to 20% of the mixture has a HLB from 10 to 15. In embodiments, 15% of the mixture has an HLB from 10 to 15. In embodiments, 5% to 20% of the mixture has an HLB below 10. In embodiments, 10% to 20% of the mixture has an HLB below 10. In embodiments, 10% of the mixture has an HLB below 10. In embodiments, 20% of the mixture has an HLB below 10. In embodiments, 20% of the mixture has an HLB below 10. In embodiments, 1% to 20% of the mixture has an HLB above 10. In embodiments, 1% to 15% of the mixture has an HLB above 10. In embodiments, 1% to 10% of the mixture has an HLB above 10. In embodiments, 1% to 5% of the mixture has an HLB above 10. In embodiments, 10% of the mixture has an HLB above 10.

Non-Ionic Compounds/Safety Profile for Human Administration

In some embodiments, the formulation includes a compound of Formula I or Formula II that is non-ionic. Such compounds tend to not denature non-targeted tissue, including proteins, upon administration, which leads to a better safety and tolerability profile. In addition these compounds have natural anesthetic properties which can reduce injection pain and improve tolerability. In some embodiments, these formulations including the non-ionic detergent are used for contacting fat tissue, abdominal fat accumulation, regional adiposity, excess sub-mental fat, and exophthalmous (e.g., due to thyroid eye disease), and/or for emulsifying, necrotizing, lysing or destroying one or more adipose cells while in specific applications leaving surrounding tissue largely unaffected (e.g., unlysed or less lysed in comparison to the lysis of fat cells (e.g., percentage of lysed cells, number of lysed cells, degree of lysis of a tissue or cell population). In certain embodiments, the compound is polidocanol.

In an exemplary embodiment, a formulation includes from about 0.1 mg to about 100 mg (e.g., about 0.5, 0.7 mg, 1 mg, 1.5 mg, 2.0 mg, 2.5 mg, 3 mg, 3.5 mg, 4 mg, 4.5 mg, 5 mg, 5.5 mg, 6 mg, 6.5 mg, 7 mg, 8 mg, 9 mg, 10 mg, 15 mg, 20 mg, 25 mg, 50 mg, 75 mg, or 100 mg, or any other amount from about 0.1 mg to about 100 mg) of a compound of Formula I or Formula II such as polidocanol. The amount of active ingredient in the formulation depends on the period of administration prescribed (including about daily, about every 3 days to about 12 months, e.g., 4 days, 5 days, 7 days, 10 days, 1 month, 45 days, 2 months, 3 months, 6 months, 8 months, 9 months, or any other release period from about daily to about 12 months). In an exemplary embodiment, a formulation includes from 0.1 mg to 100 mg (e.g., 0.5, 0.7 mg, 1 mg, 1.5 mg, 2.0 mg, 2.5 mg, 3 mg, 3.5 mg, 4 mg, 4.5 mg, 5 mg, 5.5 mg, 6 mg, 6.5 mg, 7 mg, 8 mg, 9 mg, 10 mg, 15 mg, 20 mg, 25 mg, 50 mg, 75 mg, or 100 mg, or any other amount from 0.1 mg to 100 mg) of a compound of Formula I or Formula II such as polidocanol. The amount of active ingredient in the formulation depends on the period of administration prescribed (including daily, every 3 days to 12 months, e.g., 4 days, 5 days, 7 days, 10 days, 1 month, 45 days, 2 months, 3 months, 6 months, 8 months, 9 months, or any other release period from daily to 12 months). The amount of active ingredient in the formulation depends on the number of individual administrations (e.g., injections spread over an area) that collectively are a single treatment (e.g., one total administration to the subject at one time).

Co-Solvent and Additives

It has been discovered herein, inter alia, that a $C_3$-$C_6$ alcohol such as propylene glycol is non-irritating when injected with polidocanol. Thus, in embodiments, a $C_3$-$C_6$ alcohol such as propylene glycol is administered as a co-solvent in the polidocanol compositions described herein (e.g., in a non-irritating amount).

It has further been found herein that the use of a $C_3$-$C_6$ alcohol such as propylene glycol as a co-solvent provides a reduced amount of patchy and incomplete fat tissue necrosis relative to the absence of co-solvent (e.g., propylene glycol). Thus, in embodiments, the $C_3$-$C_6$ alcohol such as propylene glycol is provided (e.g., in a composition including an active ingredient such as polidocanol) in an amount effective to reduce the amount of patchy or incomplete fat tissue necrosis relative to the absence of the $C_3$-$C_6$ alcohol such as propylene glycol.

It has been further discovered herein that a $C_3$-$C_6$ alcohol such as propylene glycol may reduce the tendency of polidocanol to solidify or crystallize upon injection into a subject relative to the absence of co-solvent (e.g., propylene glycol). In embodiments, a $C_3$-$C_6$ alcohol such as propylene glycol is provided (e.g., in a composition including an active ingredient such as polidocanol) in an amount effective to reduce the amount of crystallization or solidification of polidocanol in the subject relative to the absence of the $C_3$-$C_6$ alcohol such as propylene glycol.

It has been further discovered herein that a $C_3$-$C_6$ alcohol such as propylene glycol may reduce foam formation in the polidocanol compositions provided herein and/or increase the stability of the polidocanol compositions provided herein. In embodiments, a $C_3$-$C_6$ alcohol such as propylene glycol is provided in an amount effective to reduce the amount of foam formation in the polidocanol compositions relative to the absence of the $C_3$-$C_6$ alcohol such as propylene glycol. In embodiments, a $C_3$-$C_6$ alcohol such as propylene glycol is provided in an amount effective to increase the stability of the polidocanol compositions relative to the absence of the $C_3$-$C_6$ alcohol such as propylene glycol.

In embodiments, 2.5% of a $C_3$-$C_6$ alcohol such as propylene glycol is provided (e.g., in a composition including an active ingredient such as polidocanol).

Also provided herein are polidocanol compositions having an osmolality greater than about 600 osm. In embodiments, the polidocanol composition may include a buffer, such as a phosphate buffer. The phosphate buffer may be provided in concentration of 1% (w/w) within the polidoconal composition (e.g. see Tables 2-6 below). The composition may further include a $C_3$-$C_6$ alcohol such as propylene glycol (e.g. in a concentration of about 2.5% or 5%). In embodiments, the amount of the $C_3$-$C_6$ alcohol such as propylene glycol is about 2.5% and the amount of polidocanol is about 2.0% or less, wherein the composition is isotonic (e.g. greater than 600 osm). In embodiments provided herein containing a $C_3$-$C_6$ alcohol the $C_3$-$C_6$ alcohol may be glycerine.

It has been discovered herein that a $C_3$-$C_6$ alcohol such as propylene glycol is non-irritating when injected with a compound of Formula II. Thus, in embodiments, a $C_3$-$C_6$ alcohol such as propylene glycol is administered as a co-solvent in the compound of Formula II compositions described herein (e.g., in a non-irritating amount). It has further been found herein that the use of a $C_3$-$C_6$ alcohol such as propylene glycol as a co-solvent provides a reduced amount of patchy and incomplete fat tissue necrosis relative to the absence of co-solvent (e.g., propylene glycol). Thus, in embodiments, a $C_3$-$C_6$ alcohol such as propylene glycol is provided (e.g., in a composition including an active ingredient such as a compound of Formula II) in an amount effective to reduce the amount of patchy or incomplete fat tissue necrosis relative to the absence of the $C_3$-$C_6$ alcohol such as propylene glycol. It has been further discovered herein that a $C_3$-$C_6$ alcohol such as propylene glycol may reduce the tendency of compound of Formula II to solidify or crystallize upon injection into a subject relative to the absence of co-solvent (e.g., propylene glycol). In embodiments, a $C_3$-$C_6$ alcohol such as propylene glycol is provided (e.g., in a composition including an active ingredient such as a compound of Formula II) in an amount effective to reduce the amount of crystallization or solidification of a compound of Formula II in the subject relative to the absence of the $C_3$-$C_6$ alcohol such as propylene glycol. It has been further discovered herein that a $C_3$-$C_6$ alcohol such as propylene glycol may reduce foam formation in the compound of Formula II compositions provided herein and/or increase the stability of the compound of Formula II compositions provided herein. In embodiments, a $C_3$-$C_6$ alcohol such as propylene glycol is provided in an amount effective to reduce the amount of foam formation in the compound of Formula II compositions relative to the absence of the $C_3$-$C_6$ alcohol such as propylene glycol. In embodiments, a $C_3$-$C_6$ alcohol such as propylene glycol is provided in an amount effective to increase the stability of the compound of Formula II compositions relative to the absence of the $C_3$-$C_6$ alcohol such as propylene glycol. In embodiments, 2.5% of a $C_3$-$C_6$ alcohol such as propylene glycol is provided (e.g., in a composition including an active ingredient such as compound of Formula II). Also provided herein are compound of Formula II compositions having an osmolality greater than about 600 osm. In embodiments, the compound of Formula II composition may include a buffer, such as a phosphate buffer. The phosphate buffer may be provided in concentration of 1% (w/w) within the polidoconal composition (e.g. see Tables 2-6 below). The composition may further include a $C_3$-$C_6$ alcohol such as propylene glycol (e.g. in a concentration of about 2.5% or 5%). In embodiments, the amount of a $C_3$-$C_6$ alcohol such as propylene glycol is about 2.5% and the amount of compound of Formula II is about 2.0% or less, wherein the composition is isotonic (e.g. greater than 600 osm). In embodiments, the a $C_3$-$C_6$ alcohol is glycerine.

It has been discovered herein that a $C_3$-$C_6$ alcohol such as propylene glycol is non-irritating when injected with a compound of Formula I. Thus, in embodiments, a $C_3$-$C_6$ alcohol such as propylene glycol is administered as a co-solvent in a compound of Formula I compositions described herein (e.g., in a non-irritating amount). It has further been found herein that the use of a $C_3$-$C_6$ alcohol such as propylene glycol as a co-solvent provides a reduced amount of patchy and incomplete fat tissue necrosis relative to the absence of co-solvent (e.g., propylene glycol). Thus, in embodiments, a $C_3$-$C_6$ alcohol such as propylene glycol is provided (e.g., in a composition including an active ingredient such as a compound of Formula I) in an amount effective to reduce the amount of patchy or incomplete fat tissue necrosis relative to the absence of the $C_3$-$C_6$ alcohol such as propylene glycol. It has been further discovered herein that a $C_3$-$C_6$ alcohol such as propylene glycol may reduce the tendency of a compound of Formula I to solidify or crystallize upon injection into a subject relative to the absence of co-solvent (e.g., propylene glycol). In embodiments, a $C_3$-$C_6$ alcohol such as propylene glycol is provided (e.g., in a composition including an active ingredient such as a compound of Formula I) in an amount effective to reduce the amount of crystallization or solidification of a compound of Formula I in the subject relative to the absence of the $C_3$-$C_6$ alcohol such as propylene glycol. It has been further discovered herein that a $C_3$-$C_6$ alcohol such as propylene glycol may reduce foam formation in the compound of Formula I compositions provided herein and/or increase the stability of the compound of Formula I compositions provided herein. In embodiments, a $C_3$-$C_6$ alcohol such as propylene glycol is provided in an amount effective to reduce the amount of foam formation in the compound of Formula I compositions relative to the absence of the $C_3$-$C_6$ alcohol such as propylene glycol. In embodiments, a $C_3$-$C_6$ alcohol such as propylene glycol is provided in an amount effective to increase the stability of the compound of Formula I compositions relative to the absence of the $C_3$-$C_6$ alcohol such as propylene glycol. In embodiments, 2.5% of a $C_3$-$C_6$ alcohol such as propylene glycol is provided (e.g., in a composition including an active ingredient such as a compound of Formula I). Also provided herein are compound of Formula I compositions having an osmolality greater than about 600 osm. In embodiments, the compound of Formula I composition may include a buffer, such as a phosphate buffer. The phosphate buffer may be provided in concentration of 1% (w/w) within a $C_3$-$C_6$ alcohol such as the polidoconal composition (e.g. see Tables 2-6 below). The composition may further include a $C_3$-$C_6$ alcohol such as propylene glycol (e.g. in a concentration of about 2.5% or 5%). In embodiments, the amount of a $C_3$-$C_6$ alcohol such as propylene glycol is about 2.5% and the amount of a compound of Formula I is about 2.0% or less, wherein the composition is isotonic (e.g. greater than 600 osm). In embodiments, the a $C_3$-$C_6$ alcohol is glycerine.

Formulation Carriers

In some embodiments, the liquid carrier is a lipophilic liquid carrier. In certain embodiments, the liquid carrier is aqueous. In an embodiment, a formulation including a compound of formula I or II (e.g., polidocanol) described herein allows dispersal of the compound or salt other suitable form thereof into the layer of subcutaneous fat at a regional fat site selected from one or more of the following: a sub-mental region, an abdominal region, a waist, a hip, a lateral buttock, a thigh, a peri-orbital region, an intra-orbital region, and intramuscular region, and combinations thereof.

In certain embodiments, provided are formulations for treating regional adipose tissue, regional adiposity, or regional fat accumulation. In certain embodiments, the formulations include an effective amount of at least one compound of Formula I or Formula II (e.g., polidocanol) or a pharmaceutically acceptable or cosmetically acceptable salt and other suitable form thereof; and a liquid carrier; wherein the compound of Formula I or Formula II (e.g., polidocanol) or a pharmaceutically acceptable or cosmetically acceptable salt or others suitable form thereof and the liquid carrier formulated for injection into a layer of subcutaneous fat in the individual in need thereof. In certain embodiments, the compound of Formula II is polidocanol. In some embodiments, the formulation is stable for a period of at least 6 months at a temperature of about 0° C. to about 50° C. In certain embodiments, provided is a formulation described herein, wherein the compound of formula I or II is presented as a salt or other suitable form for administration to a human.

In certain embodiments, provided is a formulation wherein the compound of Formula I or Formula II such as polidocanol or a pharmaceutically acceptable or cosmetically acceptable salt or other suitable form thereof is present in an amount that is equal to or less than about 20% weight/volume (W/V). In certain embodiments, the compound of Formula I or Formula II such as polidocanol or a pharmaceutically acceptable or cosmetically acceptable salt or other suitable form thereof is present in an amount that is equal to or more than about 0.1% W/V to an amount that is equal to or less than about 10% W/V. In another embodiment, the compound or a pharmaceutically acceptable or cosmetically acceptable salt or other suitable form thereof is present in an amount that is equal to or more than about 0.2% W/V to an amount that is equal to or less than about 8% W/V. Also provided are embodiments of the formulations described herein wherein the compound of Formula I or Formula II such as polidocanol or a pharmaceutically acceptable or cosmetically acceptable salt or other suitable form thereof is present in an amount that is equal to or more than about 0.3% W/V to an amount that is equal to or less than about 6% W/V. In an embodiment, a compound or a pharmaceutically acceptable or cosmetically acceptable salt or other suitable form thereof is present in an amount that is equal to or more than about 0.4% W/V to an amount that is equal to or less than about 4% W/V. In some embodiments, a compound of Formula I or Formula II such as polidocanol or a pharmaceutically acceptable or cosmetically acceptable salt or other suitable form thereof is present in an amount that is equal to or more than about 0.5% W/V to an amount that is equal to or less than about 3% W/V. In a further embodiment of the formulations described herein, a compound of Formula I or Formula II or a pharmaceutically acceptable or cosmetically acceptable salt or other suitable form thereof is present in an amount that is equal to about 3% W/V. In an embodiment, a compound of Formula I or Formula II or a pharmaceutically acceptable or cosmetically acceptable salt or other suitable form thereof is present in an amount that is equal to about 0.5% W/W. Also provided are formulations wherein a compound of Formula I or Formula II or a pharmaceutically acceptable or cosmetically acceptable salt or other suitable form thereof is present in an amount that is equal to about 1% W/V. In certain embodiments, the compound of Formula II is polidocanol or a polidocanol-like compound.

In certain embodiments, the polidocanol or a pharmaceutically acceptable or cosmetically acceptable salt or other suitable form thereof is present in an amount that is equal to or less than about 10% weight/volume (W/V). In certain embodiments the polidocanol or a pharmaceutically acceptable or cosmetically acceptable salt or other suitable form thereof is present in an amount that is equal to or more than about 0.1% W/V to an amount that is equal to or less than about 10% W/V. In some other embodiments the polidocanol or a pharmaceutically acceptable or cosmetically acceptable salt or other suitable form thereof is present in an amount that is equal to or more than about 0.2% W/V to an amount that is equal to or less than about 8% W/V. In certain embodiments, the polidocanol or a pharmaceutically acceptable or cosmetically acceptable salt or other suitable form thereof is present in an amount that is equal to or more than about 0.3% W/V to an amount that is equal to or less than about 6% W/V. In some other embodiments the polidocanol or a pharmaceutically acceptable or cosmetically acceptable salt or other suitable form thereof is present in an amount that is equal to or more than about 0.4% W/V to an amount that is equal to or less than about 4% W/V. In select embodiments, the polidocanol or a pharmaceutically acceptable or cosmetically acceptable salt or other suitable form thereof is present in an amount that is equal to or more than about 0.5% W/V to an amount that is equal to or less than about 3% W/V. In some other embodiments the polidocanol or a pharmaceutically acceptable or cosmetically acceptable salt or other suitable form thereof is present in an amount that is equal to about 3% W/V. In certain further embodiments, the polidocanol or a pharmaceutically acceptable or cosmetically acceptable salt or other suitable form thereof is present in an amount that is equal to about 0.5% W/V. In some other embodiments, the polidocanol or a pharmaceutically acceptable or cosmetically acceptable salt or other suitable form thereof is present in an amount that is equal to about 1% W/V.

In certain embodiments, provided is a formulation wherein the compound of Formula I or Formula II (e.g., polidocanol), or a pharmaceutically acceptable or cosmetically acceptable salt thereof, is present in an amount that is equal to or less than about 20% weight/volume (W/V). In embodiment, the compound, or pharmaceutically acceptable or cosmetically acceptable salt thereof, is between about 0.1% W/V and about 10% W/V. In embodiment, the compound, or pharmaceutically acceptable or cosmetically acceptable salt thereof, is between about 0.2% W/V to about 8% W/V. In embodiment, the compound, or pharmaceutically acceptable or cosmetically acceptable salt thereof, is between about 0.3% W/V to about 6% W/V. In embodiment, the compound, or pharmaceutically acceptable or cosmetically acceptable salt thereof, is between about 0.4% W/V to about 4% W/V. In embodiment, the compound, or pharmaceutically acceptable or cosmetically acceptable salt thereof, is between about 0.5% W/V to about 3% W/V. In embodiment, the compound, or pharmaceutically acceptable or cosmetically acceptable salt thereof, is about 3% W/V. In embodiment, the compound, or pharmaceutically acceptable or cosmetically acceptable salt thereof, is about 0.5% W/W. In embodiment, the compound, or pharmaceutically acceptable or cosmetically acceptable salt thereof, is about 1% W/V. In certain embodiments, the compound is polidocanol or a polidocanol-like compound.

In certain embodiments, the polidocanol, or a pharmaceutically acceptable or cosmetically acceptable salt, thereof is less than about 10% weight/volume (W/V). In certain embodiments, the polidocanol, or a pharmaceutically acceptable or cosmetically acceptable salt, thereof is between about 0.1% W/V to about 10% W/V. In certain embodiments, the polidocanol, or a pharmaceutically acceptable or cosmetically acceptable salt, thereof is between about 0.2% W/V to about 8% W/V. In certain embodiments, the polidocanol, or a pharmaceutically acceptable or cosmetically acceptable salt, thereof is between about 0.3% W/V to about 6% W/V. In certain embodiments, the polidocanol, or a pharmaceutically acceptable or cosmetically acceptable salt, thereof is between about 0.4% W/V to about 4% W/V. In certain embodiments, the polidocanol, or a pharmaceutically acceptable or cosmetically acceptable salt, thereof is between about 0.5% W/V to about 3% W/V. In certain embodiments, the polidocanol, or a pharmaceutically acceptable or cosmetically acceptable salt, thereof is about 3% W/V. In certain embodiments, the polidocanol, or a pharmaceutically acceptable or cosmetically acceptable salt, thereof is about 0.5% W/V. In certain embodiments, the polidocanol, or a pharmaceutically acceptable or cosmetically acceptable salt, thereof is about 1% W/V.

In certain embodiments, provided is a formulation wherein the compound of Formula I or Formula II (e.g., polidocanol), or a pharmaceutically acceptable or cosmetically acceptable salt thereof, is present in an amount that is equal to or less than 20% weight/volume (W/V). In embodiment, the compound, or pharmaceutically acceptable or cosmetically acceptable salt thereof, is between 0.1% W/V and 10% W/V. In embodiment, the compound, or pharmaceutically acceptable or cosmetically acceptable salt thereof, is between 0.2% W/V to 8% W/V. In embodiment, the compound, or pharmaceutically acceptable or cosmetically acceptable salt thereof, is between 0.3% W/V to 6% W/V. In embodiment, the compound, or pharmaceutically acceptable or cosmetically acceptable salt thereof, is between 0.4% W/V to 4% W/V. In embodiment, the compound, or pharmaceutically acceptable or cosmetically acceptable salt thereof, is between 0.5% W/V to 3% W/V. In embodiment, the compound, or pharmaceutically acceptable or cosmetically acceptable salt thereof, is 3% W/V. In embodiment, the compound, or pharmaceutically acceptable or cosmetically acceptable salt thereof, is 0.5% W/W. In embodiment, the compound, or pharmaceutically acceptable or cosmetically acceptable salt thereof, is 1% W/V. In certain embodiments, the compound is polidocanol or a polidocanol-like compound.

In certain embodiments, the polidocanol, or a pharmaceutically acceptable or cosmetically acceptable salt, thereof is less than 10% weight/volume (W/V). In certain embodiments, the polidocanol, or a pharmaceutically acceptable or cosmetically acceptable salt, thereof is between 0.1% W/V to 10% W/V. In certain embodiments, the polidocanol, or a pharmaceutically acceptable or cosmetically acceptable salt, thereof is between 0.2% W/V to 8% W/V. In certain embodiments, the polidocanol, or a pharmaceutically acceptable or cosmetically acceptable salt, thereof is between 0.3% W/V to 6% W/V. In certain embodiments, the polidocanol, or a pharmaceutically acceptable or cosmetically acceptable salt, thereof is between 0.4% W/V to 4% W/V. In certain embodiments, the polidocanol, or a pharmaceutically acceptable or cosmetically acceptable salt, thereof is between 0.5% W/V to 3% W/V. In certain embodiments, the polidocanol, or a pharmaceutically acceptable or cosmetically acceptable salt, thereof is 3% W/V. In certain embodiments, the polidocanol, or a pharmaceutically acceptable or cosmetically acceptable salt, thereof is 0.5% W/V. In certain embodiments, the polidocanol, or a pharmaceutically acceptable or cosmetically acceptable salt, thereof is 1% W/V.

Described herein is the determination that safety and tolerability in connection with the reduction and emulsification of fat tissue in human is improved by a formulation including an effective amount, for example a therapeutically or cosmetically effective amount, of polidocanol and from about 0.5% to about 10% of an alcohol having 3 to 6 carbon atoms. Also identified are advantages to formulations including less than 2.0% polidocanol (e.g. from about 0.1% to about 1.5% or about 0.5% to about 1.25% or less than about 1%). Described herein is the determination that safety and tolerability in connection with the reduction and emulsification of fat tissue in human is improved by a formulation including an effective amount, for example a therapeutically or cosmetically effective amount, of polidocanol and from 0.5% to 10% of an alcohol having 3 to 6 carbon atoms. Also identified are advantages to formulations including less than 2.0% polidocanol (e.g. from 0.1% to 1.5% or 0.5% to 1.25% or less than 1%). Also identified are advantages to administration of polidocanol formulations described herein not more than once every 14 days (e.g., not more than 28 days (e.g. approximately monthly administration)).

In some embodiments, described herein are formulations including an effective amount, for example a therapeutically or cosmetically effective amount, of polidocanol and from about 0.5% W/V to about 10% W/V of propylene glycol. In some embodiments, described herein are formulations including an effective amount of polidocanol and from about 0.5% W/V to about 10% W/V of glycerine. Propylene glycol and glycerine are small, water soluble, hydroxylated organic molecules, which ensure formulation stability and safety when used with polidocanol. Both propylene glycol and glycerine are nearly non-toxic and non-irritating and suitable for subcutaneous injection. In some embodiments, the formulation includes an effective amount, example a therapeutically or cosmetically effective amount, of polidocanol and 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, or 10% W/V propylene glycol and does not contain ethanol or an ether. In some embodiments, the formulation includes an effective amount, for example a therapeutically or cosmetically effective amount, of polidocanol and 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, or 10% W/V glycerine and does not contain ethanol or an ether. In some embodiments, the formulation includes an effective amount, for example a therapeutically or cosmetically effective amount, of polidocanol and from about 0.5% to about 10% W/V of propylene glycol and does not contain aliphatic polyethers. In some embodiments, the formulation includes an effective amount, for example a therapeutically or cosmetically effective amount, of polidocanol and from about 0.5% to about 10% W/V of glycerine and does not contain aliphatic polyethers. In some embodiments, the formulation includes an effective amount, for example a therapeutically or cosmetically effective amount, of polidocanol and from about 0.5% to about 10% W/V of propylene glycol and does not contain polyethylene glycol. In some embodiments, the formulation includes an effective amount, for example a therapeutically or cosmetically effective amount, of polidocanol and from about 0.5% to about 10% W/V of glycerine and does not contain polyethylene glycol. In some embodiments, the formulation includes an effective amount, for example a therapeutically or cosmetically effective amount, of polidocanol and from about 0.5% to about 10% W/V of propylene glycol and does not contain poloxamers. In some embodiments, the formulation includes an effective amount, for example a therapeutically or cosmetically effective amount, of polidocanol and from about 0.5% to about 10% W/V of glycerine and does not contain poloxamers. In some embodiments, the formulation is for subcutaneous injection. In some embodiments, the formulation is for injection into the submental region of a human in need. In some embodiments, the formulation is for injection into a fat pad.

In some embodiments, the formulation includes an effective amount, for example a therapeutically or cosmetically effective amount, of polidocanol and from about 1.0% to about 5.0% W/V of an alcohol having 3 to 6 carbon atoms. In some embodiments, the formulation includes an effective amount, for example a therapeutically or cosmetically effective amount, of polidocanol and approximately 5.0% W/V of an alcohol having 3 to 6 carbon atoms. In some embodiments, the formulation includes polidocanol in an amount that is greater than 1.0% W/V and from about 1.0% to about 5.0% W/V of an alcohol having 3 to 6 carbon atoms. In some embodiments, the formulation includes polidocanol in an amount that is greater than 1.0% W/V and approximately 5.0% W/V of an alcohol having 3 to 6 carbon atoms. In some embodiments, the formulation includes polidocanol in an amount that is greater than 1.0% W/V and from about 1.0% to about 5.0% W/V of an alcohol having 3 to 6 carbon atoms and does not contain polyethylene glycol. In some embodiments, the formulation includes polidocanol in an amount that is greater than 1.0% W/V and from about 1.0% to about 5.0% W/V of an alcohol having 3 to 6 carbon atoms and does not contain ethanol or an ether. In some embodiments, the formulation includes polidocanol in an amount that is greater than 1.0% W/V and from about 1.0% to about 5.0% W/V of an alcohol having 3 to 6 carbon atoms and does not contain aliphatic polyethers. In some embodiments, the formulation includes polidocanol in an amount that is greater than 1.0% W/V and from about 1.0% to about 5.0% W/V of an alcohol having 3 to 6 carbon atoms and does not contain poloxamers.

In embodiments, the formulation includes polidocanol in an amount from about 0.1% W/V to about 20.0% W/V and from about 1.0% to about 5.0% W/V of an alcohol having 3 to 6 carbon atoms. In embodiments, the formulation includes polidocanol in an amount from about 0.1% W/V to about 20.0% W/V and about 5.0% W/V of an alcohol having 3 to 6 carbon atoms. In some embodiments, the formulation includes polidocanol in an amount from about 0.1% W/V to about 20.0% W/V and from about 1.0% to about 5.0% W/V of an alcohol having 3 to 6 carbon atoms and does not include polyethylene glycol. In some embodiments, the formulation includes polidocanol in an amount from about 0.1% W/V to about 20.0% W/V and from about 1.0% to about 5.0% W/V of an alcohol having 3 to 6 carbon atoms and does not include ethanol or an ether. In some embodiments, the formulation includes polidocanol in an amount from about 0.1% W/V to about 20.0% W/V and from about 1.0% to about 5.0% W/V of an alcohol having 3 to 6 carbon atoms and does not include aliphatic polyethers. In some embodiments, the formulation includes polidocanol in an amount from about 0.1% W/V to about 20.0% W/V and from about 1.0% to about 5.0% W/V of an alcohol having 3 to 6 carbon atoms and does not include poloxamers.

In some embodiments, the formulation includes polidocanol in an amount from about 0.5% W/V to about 10.0% W/V and from about 1.0% to about 5.0% W/V of an alcohol having 3 to 6 carbon atoms. In some embodiments, the formulation includes polidocanol in an amount from about 0.5% W/V to about 10.0% W/V and approximately 5.0% W/V of an alcohol having 3 to 6 carbon atoms. In some embodiments, the formulation includes polidocanol in an amount from about 0.5% W/V to about 10.0% W/V and from about 1.0% to about 5.0% W/V of an alcohol having 3 to 6 carbon atoms and does not include polyethylene glycol. In some embodiments, the formulation includes polidocanol in an amount from about 0.5% W/V to about 10.0% W/V and from about 1.0% to about 5.0% W/V of an alcohol having 3 to 6 carbon atoms and does not include ethanol or an ether. In some embodiments, the formulation includes polidocanol in an amount from about 0.5% W/V to about 10.0% W/V and from about 1.0% to about 5.0% W/V of an alcohol having 3 to 6 carbon atoms and does not include aliphatic polyethers. In some embodiments, the formulation includes polidocanol in an amount from about 0.5% W/V to about 10.0% W/V and from about 1.0% to about 5.0% W/V of an alcohol having 3 to 6 carbon atoms and does not include poloxamers.

In some embodiments, the formulation includes polidocanol in an amount from about 0.5% W/V to about 2.0% W/V and from about 1.0% to about 5.0% W/V of an alcohol having 3 to 6 carbon atoms. In some embodiments, the formulation includes polidocanol in an amount from about 0.5% W/V to about 2.0% W/V and approximately 5.0% W/V of an alcohol having 3 to 6 carbon atoms. In some embodiments, the formulation includes polidocanol in an amount from about 0.5% W/V to about 2.0% W/V and from about 1.0% to about 5.0% W/V of an alcohol having 3 to 6 carbon atoms and does not include polyethylene glycol. In some embodiments, the formulation includes polidocanol in an amount from about 0.5% W/V to about 2.0% W/V and from about 1.0% to about 5.0% W/V of an alcohol having 3 to 6 carbon atoms and does not include ethanol or an ether. In some embodiments, the formulation includes polidocanol in an amount from about 0.5% W/V to about 2.0% W/V and from about 1.0% to about 5.0% W/V of an alcohol having 3 to 6 carbon atoms and does not include aliphatic polyethers. In some embodiments, the formulation includes polidocanol in an amount from about 0.5% W/V to about 2.0% W/V and from about 1.0% to about 5.0% W/V of an alcohol having 3 to 6 carbon atoms and does not include poloxamers.

In some embodiments, the formulation includes polidocanol in an amount of about 0.5% W/V and from about 1.0% to about 5.0% W/V of an alcohol having 3 to 6 carbon atoms. In some embodiments, the formulation includes polidocanol in an amount of about 0.5% W/V and approximately 5.0% W/V of an alcohol having 3 to 6 carbon atoms. In some embodiments, the formulation includes polidocanol in an amount of about 0.5% W/V and from about 1.0% to about 5.0% W/V of an alcohol having 3 to 6 carbon atoms and does not include polyethylene glycol. In some embodiments, the formulation includes polidocanol in an amount of about 0.5% W/V and from about 1.0% to about 5.0% W/V of an alcohol having 3 to 6 carbon atoms and does not include ethanol or an ether. In some embodiments, the formulation includes polidocanol in an amount of about 0.5% W/V and from about 1.0% to about 5.0% W/V of an alcohol having 3 to 6 carbon atoms and does not include aliphatic polyethers. In some embodiments, the formulation includes polidocanol in an amount of about 0.5% W/V and from about 1.0% to about 5.0% W/V of an alcohol having 3 to 6 carbon atoms and does not include poloxamers.

In some embodiments, the formulation includes polidocanol in an amount of about 1.25% W/V and from about 1.0% to about 5.0% W/V of an alcohol having 3 to 6 carbon atoms. In some embodiments, the formulation includes polidocanol in an amount of about 1.25% W/V and approximately 5.0% W/V of an alcohol having 3 to 6 carbon atoms. In some embodiments, the formulation includes polidocanol in an amount of about 1.25% W/V and from about 1.0% to about 5.0% W/V of an alcohol having 3 to 6 carbon atoms and does not include polyethylene glycol. In some embodiments, the formulation includes polidocanol in an amount of about 1.25% W/V and from about 1.0% to about 5.0% W/V of an alcohol having 3 to 6 carbon atoms and does not include ethanol or an ether. In some embodiments, the formulation includes polidocanol in an amount of about 1.25% W/V and from about 1.0% to about 5.0% W/V of an alcohol having 3 to 6 carbon atoms and does not include aliphatic polyethers. In some embodiments, the formulation includes polidocanol in an amount of about 1.25% W/V and from about 1.0% to about 5.0% W/V of an alcohol having 3 to 6 carbon atoms and does not include poloxamers.

In some embodiments, the formulation includes polidocanol in an amount of about 2.0% W/V and from about 1.0% to about 5.0% W/V of an alcohol having 3 to 6 carbon atoms. In some embodiments, the formulation includes polidocanol in an amount of about 2.0% W/V and approximately 5.0% W/V of an alcohol having 3 to 6 carbon atoms. In some embodiments, the formulation includes polidocanol in an amount of about 2.0% W/V and from about 1.0% to about 5.0% W/V of an alcohol having 3 to 6 carbon atoms and does not include polyethylene glycol. In some embodiments, the formulation includes polidocanol in an amount of about 2.0% W/V and from about 1.0% to about 5.0% W/V of an alcohol having 3 to 6 carbon atoms and does not include ethanol or an ether. In some embodiments, the formulation includes polidocanol in an amount of about 2.0% W/V and from about 1.0% to about 5.0% W/V of an alcohol having 3 to 6 carbon atoms and does not include aliphatic polyethers. In some embodiments, the formulation includes polidocanol in an amount of about 2.0% W/V and from about 1.0% to about 5.0% W/V of an alcohol having 3 to 6 carbon atoms and does not include poloxamers.

In some embodiments, described herein are formulations including an effective amount, for example a therapeutically or cosmetically effective amount, of polidocanol and from 0.5% W/V to 10% W/V of propylene glycol. In some embodiments, described herein are formulations including an effective amount of polidocanol and from 0.5% W/V to 10% W/V of glycerine. Propylene glycol and glycerine are small, water soluble, hydroxylated organic molecules, which ensure formulation stability and safety when used with polidocanol. Both propylene glycol and glycerine are nearly non-toxic and non-irritating and suitable for subcutaneous injection. In some embodiments, the formulation includes an effective amount, example a therapeutically or cosmetically effective amount, of polidocanol and 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, or 10% W/V propylene glycol and does not contain ethanol or an ether. In some embodiments, the formulation includes an effective amount, for example a therapeutically or cosmetically effective amount, of polidocanol and 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, or 10% W/V glycerine and does not contain ethanol or an ether. In some embodiments, the formulation includes an effective amount, for example a therapeutically or cosmetically effective amount, of polidocanol and from 0.5% to 10% W/V of propylene glycol and does not contain aliphatic polyethers. In some embodiments, the formulation includes an effective amount, for example a therapeutically or cosmetically effective amount, of polidocanol and from 0.5% to 10% W/V of glycerine and does not contain aliphatic polyethers. In some embodiments, the formulation includes an effective amount, for example a therapeutically or cosmetically effective amount, of polidocanol and from 0.5% to 10% W/V of propylene glycol and does not contain polyethylene glycol. In some embodiments, the formulation includes an effective amount, for example a therapeutically or cosmetically effective amount, of polidocanol and from 0.5% to 10% W/V of glycerine and does not contain polyethylene glycol. In some embodiments, the formulation includes an effective amount, for example a therapeutically or cosmetically effective amount, of polidocanol and from 0.5% to 10% W/V of propylene glycol and does not contain poloxamers. In some embodiments, the formulation includes an effective amount, for example a therapeutically or cosmetically effective amount, of polidocanol and from 0.5% to 10% W/V of glycerine and does not contain poloxamers. In some embodiments, the formulation is for subcutaneous injection. In some embodiments, the formulation is for injection into the submental region of a human in need. In some embodiments, the formulation is for injection into a fat pad.

In some embodiments, the formulation includes an effective amount, for example a therapeutically or cosmetically effective amount, of polidocanol and from 1.0% to 5.0% W/V of an alcohol having 3 to 6 carbon atoms. In some embodiments, the formulation includes an effective amount, for example a therapeutically or cosmetically effective amount, of polidocanol and 5.0% W/V of an alcohol having 3 to 6 carbon atoms. In some embodiments, the formulation includes polidocanol in an amount that is greater than 1.0% W/V and from 1.0% to 5.0% W/V of an alcohol having 3 to 6 carbon atoms. In some embodiments, the formulation includes polidocanol in an amount that is greater than 1.0% W/V and 5.0% W/V of an alcohol having 3 to 6 carbon atoms. In some embodiments, the formulation includes polidocanol in an amount that is greater than 1.0% W/V and from 1.0% to 5.0% W/V of an alcohol having 3 to 6 carbon atoms and does not contain polyethylene glycol. In some embodiments, the formulation includes polidocanol in an amount that is greater than 1.0% W/V and from 1.0% to 5.0% W/V of an alcohol having 3 to 6 carbon atoms and does not contain ethanol or an ether. In some embodiments, the formulation includes polidocanol in an amount that is greater than 1.0% W/V and from 1.0% to 5.0% W/V of an alcohol having 3 to 6 carbon atoms and does not contain aliphatic polyethers. In some embodiments, the formulation includes polidocanol in an amount that is greater than 1.0% W/V and from 1.0% to 5.0% W/V of an alcohol having 3 to 6 carbon atoms and does not contain poloxamers.

In embodiments, the formulation includes polidocanol in an amount from 0.1% W/V to 20.0% W/V and from 1.0% to 5.0% W/V of an alcohol having 3 to 6 carbon atoms. In embodiments, the formulation includes polidocanol in an amount from 0.1% W/V to 20.0% W/V and 5.0% W/V of an alcohol having 3 to 6 carbon atoms. In some embodiments, the formulation includes polidocanol in an amount from 0.1% W/V to 20.0% W/V and from 1.0% to 5.0% W/V of an alcohol having 3 to 6 carbon atoms and does not include polyethylene glycol. In some embodiments, the formulation includes polidocanol in an amount from 0.1% W/V to 20.0% W/V and from 1.0% to 5.0% W/V of an alcohol having 3 to 6 carbon atoms and does not include ethanol or an ether. In some embodiments, the formulation includes polidocanol in an amount from 0.1% W/V to 20.0% W/V and from 1.0% to 5.0% W/V of an alcohol having 3 to 6 carbon atoms and does not include aliphatic polyethers. In some embodiments, the formulation includes polidocanol in an amount from 0.1% W/V to 20.0% W/V and from 1.0% to 5.0% W/V of an alcohol having 3 to 6 carbon atoms and does not include poloxamers.

In some embodiments, the formulation includes polidocanol in an amount from 0.5% W/V to 10.0% W/V and from 1.0% to 5.0% W/V of an alcohol having 3 to 6 carbon atoms. In some embodiments, the formulation includes polidocanol in an amount from 0.5% W/V to 10.0% W/V and 5.0% W/V of an alcohol having 3 to 6 carbon atoms. In some embodiments, the formulation includes polidocanol in an amount from 0.5% W/V to 10.0% W/V and from 1.0% to 5.0% W/V of an alcohol having 3 to 6 carbon atoms and does not include polyethylene glycol. In some embodiments, the formulation includes polidocanol in an amount from 0.5% W/V to 10.0% W/V and from 1.0% to 5.0% W/V of an alcohol having 3 to 6 carbon atoms and does not include ethanol or an ether. In some embodiments, the formulation includes polidocanol in an amount from 0.5% W/V to 10.0% W/V and from 1.0% to 5.0% W/V of an alcohol having 3 to 6 carbon atoms and does not include aliphatic polyethers. In some embodiments, the formulation includes polidocanol in an amount from 0.5% W/V to 10.0% W/V and from 1.0% to 5.0% W/V of an alcohol having 3 to 6 carbon atoms and does not include poloxamers.

In some embodiments, the formulation includes polidocanol in an amount from 0.5% W/V to 2.0% W/V and from 1.0% to 5.0% W/V of an alcohol having 3 to 6 carbon atoms. In some embodiments, the formulation includes polidocanol in an amount from 0.5% W/V to 2.0% W/V and 5.0% W/V of an alcohol having 3 to 6 carbon atoms. In some embodiments, the formulation includes polidocanol in an amount from 0.5% W/V to 2.0% W/V and from 1.0% to 5.0% W/V of an alcohol having 3 to 6 carbon atoms and does not include polyethylene glycol. In some embodiments, the formulation includes polidocanol in an amount from 0.5% W/V to 2.0% W/V and from 1.0% to 5.0% W/V of an alcohol having 3 to 6 carbon atoms and does not include ethanol or an ether. In some embodiments, the formulation includes polidocanol in an amount from 0.5% W/V to 2.0% W/V and from 1.0% to 5.0% W/V of an alcohol having 3 to 6 carbon atoms and does not include aliphatic polyethers. In some embodiments, the formulation includes polidocanol in an amount from 0.5% W/V to 2.0% W/V and from 1.0% to 5.0% W/V of an alcohol having 3 to 6 carbon atoms and does not include poloxamers.

In some embodiments, the formulation includes polidocanol in an amount of 0.5% W/V and from 1.0% to 5.0% W/V of an alcohol having 3 to 6 carbon atoms. In some embodiments, the formulation includes polidocanol in an amount of 0.5% W/V and 5.0% W/V of an alcohol having 3 to 6 carbon atoms. In some embodiments, the formulation includes polidocanol in an amount of 0.5% W/V and from 1.0% to 5.0% W/V of an alcohol having 3 to 6 carbon atoms and does not include polyethylene glycol. In some embodiments, the formulation includes polidocanol in an amount of 0.5% W/V and from 1.0% to 5.0% W/V of an alcohol having 3 to 6 carbon atoms and does not include ethanol or an ether. In some embodiments, the formulation includes polidocanol in an amount of 0.5% W/V and from 1.0% to 5.0% W/V of an alcohol having 3 to 6 carbon atoms and does not include aliphatic polyethers. In some embodiments, the formulation includes polidocanol in an amount of 0.5% W/V and from 1.0% to 5.0% W/V of an alcohol having 3 to 6 carbon atoms and does not include poloxamers.

In some embodiments, the formulation includes polidocanol in an amount of 1.25% W/V and from 1.0% to 5.0% W/V of an alcohol having 3 to 6 carbon atoms. In some embodiments, the formulation includes polidocanol in an amount of 1.25% W/V and 5.0% W/V of an alcohol having 3 to 6 carbon atoms. In some embodiments, the formulation includes polidocanol in an amount of 1.25% W/V and from 1.0% to 5.0% W/V of an alcohol having 3 to 6 carbon atoms and does not include polyethylene glycol. In some embodiments, the formulation includes polidocanol in an amount of 1.25% W/V and from 1.0% to 5.0% W/V of an alcohol having 3 to 6 carbon atoms and does not include ethanol or an ether. In some embodiments, the formulation includes polidocanol in an amount of 1.25% W/V and from 1.0% to 5.0% W/V of an alcohol having 3 to 6 carbon atoms and does not include aliphatic polyethers. In some embodiments, the formulation includes polidocanol in an amount of 1.25% W/V and from 1.0% to 5.0% W/V of an alcohol having 3 to 6 carbon atoms and does not include poloxamers.

In some embodiments, the formulation includes polidocanol in an amount of 2.0% W/V and from 1.0% to 5.0% W/V of an alcohol having 3 to 6 carbon atoms. In some embodiments, the formulation includes polidocanol in an amount of 2.0% W/V and 5.0% W/V of an alcohol having 3 to 6 carbon atoms. In some embodiments, the formulation includes polidocanol in an amount of 2.0% W/V and from 1.0% to 5.0% W/V of an alcohol having 3 to 6 carbon atoms and does not include polyethylene glycol. In some embodiments, the formulation includes polidocanol in an amount of 2.0% W/V and from 1.0% to 5.0% W/V of an alcohol having 3 to 6 carbon atoms and does not include ethanol or an ether. In some embodiments, the formulation includes polidocanol in an amount of 2.0% W/V and from 1.0% to 5.0% W/V of an alcohol having 3 to 6 carbon atoms and does not include aliphatic polyethers. In some embodiments, the formulation includes polidocanol in an amount of 2.0% W/V and from 1.0% to 5.0% W/V of an alcohol having 3 to 6 carbon atoms and does not include poloxamers.

In some embodiments the osmolality of the formulation is less than 700 milliosmoles. In some embodiments the osmolality of the formulation is less than 400 milliosmoles. In some embodiments the formulation has 5% propylene glycol and less than 700 milliosmoles. In some embodiments the formulation has 2.5% propylene glycol and less than 400 milliosmoles. Non-limiting examples of formulations with acceptable osmoles that use propylene glycol are shown in FIG. 9C. In some embodiments the osmolality of the formulation is less than 700 milliosmoles/kg. In some embodiments the osmolality of the formulation is less than 400/kg milliosmoles. In some embodiments the formulation has 5% propylene glycol and less than 700 milliosmoles; kg. In some embodiments the formulation has 2.5% propylene glycol and less than 400 milliosmoles/kg. Non-limiting examples of formulations with acceptable osmoles that use propylene glycol are shown in FIG. 9C.

In some embodiments, the formulation has a pH from about 6 to about 9. In some embodiments, the formulation has a pH of about 7 to about 8.

In some embodiments, the formulation includes polidocanol in about 0.5% W/V and about 5.0% propylene glycol and does not include polyethylene glycol or poloxamers and has a pH of about 7 to about 8 and is formulated for subcutaneous injection into the submental region of a human in need.

In some embodiments, the formulation includes polidocanol in about 0.5% W/V and about 5.0% glycerine and does not include polyethylene glycol or poloxamers and has a pH of about 7 to about 8 and is formulated for subcutaneous injection into the submental region of a human in need.

In some embodiments, the formulation includes polidocanol in an amount of about 1.25% W/V and about 5.0% propylene glycol and does not include polyethylene glycol or poloxamers and has a pH of about 7 to about 8 and is formulated for subcutaneous injection into the submental region of a human in need.

In some embodiments, the formulation includes polidocanol in an amount of about 1.25% W/V and about 5.0% glycerine and does not include polyethylene glycol or poloxamers and has a pH of about 7 to about 8 and is formulated for subcutaneous injection into the submental region of a human in need.

In some embodiments, the formulation includes polidocanol in an amount of about 2.0% W/V and about 5.0% propylene glycol and does not include polyethylene glycol or poloxamers and has a pH of about 7 to about 8 and is formulated for subcutaneous injection into the submental region of a human in need.

In some embodiments, the formulation includes polidocanol in an amount of about 2.0% W/V and about 5.0% glycerine and does not include polyethylene glycol or poloxamers and has a pH of about 7 to about 8 and is formulated for subcutaneous injection into the submental region of a human in need.

In some embodiments, the formulation has a pH from 6 to 9. In some embodiments, the formulation has a pH of 7 to 8.

In some embodiments, the formulation includes polidocanol in 0.5% W/V and 5.0% propylene glycol and does not include polyethylene glycol or poloxamers and has a pH of 7 to 8 and is formulated for subcutaneous injection into the submental region of a human in need.

In some embodiments, the formulation includes polidocanol in 0.5% W/V and 5.0% glycerine and does not include polyethylene glycol or poloxamers and has a pH of 7 to 8 and is formulated for subcutaneous injection into the submental region of a human in need.

In some embodiments, the formulation includes polidocanol in an amount of 1.25% W/V and 5.0% propylene glycol and does not include polyethylene glycol or poloxamers and has a pH of 7 to 8 and is formulated for subcutaneous injection into the submental region of a human in need.

In some embodiments, the formulation includes polidocanol in an amount of 1.25% W/V and 5.0% glycerine and does not include polyethylene glycol or poloxamers and has a pH of 7 to 8 and is formulated for subcutaneous injection into the submental region of a human in need.

In some embodiments, the formulation includes polidocanol in an amount of 2.0% W/V and 5.0% propylene glycol and does not include polyethylene glycol or poloxamers and has a pH of 7 to 8 and is formulated for subcutaneous injection into the submental region of a human in need.

In some embodiments, the formulation includes polidocanol in an amount of 2.0% W/V and 5.0% glycerine and does not include polyethylene glycol or poloxamers and has a pH of 7 to 8 and is formulated for subcutaneous injection into the submental region of a human in need.

Injection Volumes of Compounds of Formula I and II (e.g., Polidocanol)

In some embodiments, the formulations described herein are injectable by means of subcutaneous injection. Subcutaneous administration has the benefit of local, targeted administration. Unlike other systemic modes of administration, subcutaneous administration results in a localized distribution of the active agents. In certain embodiments, these injectable formulations include a compound of Formula I or Formula II (e.g., polidocanol) or a pharmaceutically acceptable or cosmetically acceptable salt or other suitable form thereof in an injection volume that is from about 0.01 mL to about 100 mL, and each volume in between this range, and further including ranges from about 0.01 mL to about 100 mL, 0.5 mL to about 50 mL, from about 1 mL to about 25 mL, from about 2 mL to about 20 mL, from about 3 mL to about 10 mL.

In some embodiments, the injectable formulation includes a compound of Formula I or Formula II (e.g., polidocanol) or a pharmaceutically acceptable or cosmetically acceptable salt or other suitable form thereof in an injection volume that is equal to or less than about 2 mL. In some other embodiments the compound of Formula I or Formula II or a pharmaceutically acceptable or cosmetically acceptable salt or other suitable form thereof injection volume is equal to or more than about 0.05 mL to an injection volume that is equal to or less than about 2 mL. In certain other embodiments, the compound of Formula I or Formula II or a pharmaceutically acceptable or cosmetically acceptable salt or other suitable form thereof injection volume is equal to or more than about 0.1 mL to an injection volume that is equal to or less than about 1.8 mL. In some embodiments, the compound of Formula I or Formula II or a pharmaceutically acceptable or cosmetically acceptable salt or other suitable form thereof injection volume is equal to or more than about 0.2 mL to an injection volume that is equal to or less than about 1.6 mL. In certain embodiments, the compound of Formula I or Formula II or a pharmaceutically acceptable or cosmetically acceptable salt or other suitable form thereof injection volume is equal to or more than about 0.3 mL to an injection volume that is equal to or less than about 1.4 mL. In select embodiments, the compound of Formula I or Formula II or a pharmaceutically acceptable or cosmetically acceptable salt or other suitable form thereof injection volume is equal to or more than about 0.4 mL to an injection volume that is equal to or less than about 1.2 mL. In some embodiments, the compound of Formula I or Formula II or a pharmaceutically acceptable or cosmetically acceptable salt or other suitable form thereof injection volume is equal to or more than about 0.5 mL to an injection volume that is equal to or less than about 1 mL. In some embodiments, a compound of Formula I or Formula II or a pharmaceutically acceptable or cosmetically acceptable salt or other suitable form thereof injection volume is equal to about 0.1 mL. In some further embodiments is provided a compound of Formula I or Formula II or a pharmaceutically acceptable or cosmetically acceptable salt or other suitable form thereof injection volume is equal to about 0.2 mL. In certain embodiments, a compound of Formula I or Formula II or a pharmaceutically acceptable or cosmetically acceptable salt or other suitable form thereof injection volume is equal to about 0.5 mL. In select embodiments, a compound of Formula I or Formula II or a pharmaceutically acceptable or cosmetically acceptable salt or other suitable form thereof injection volume is equal to about 1 mL. In certain embodiments, a compound of Formula I or Formula II or a pharmaceutically acceptable or cosmetically acceptable salt or other suitable form thereof injection volume is equal to about 2 mL.

In an aspect, provided is an injectable formulation for treating regional adipose tissue, regional adiposity, or regional fat accumulation including: an effective amount of at least one of a compound of Formula I or Formula II or a pharmaceutically acceptable or cosmetically acceptable salt or other suitable form thereof; and a liquid carrier; the compound of Formula I or Formula II or a pharmaceutically acceptable or cosmetically acceptable salt or other suitable form thereof and the liquid carrier formulated for injection into a layer of subcutaneous fat in a human in need.

In certain embodiments provided is a formulation including a compound of Formula I or Formula II, including polidocanol and polidocanol-like compounds, or a pharmaceutically acceptable or cosmetically acceptable salt or other suitable form thereof wherein the injection volume is equal to or less than about 2 mL. In certain other embodiments, the injection volume is equal to or more than about 0.05 mL to an injection volume that is equal to or less than about 2 mL. In an embodiment, the injection volume is equal to or more than about 0.1 mL to an injection volume that is equal to or less than about 1.8 mL. In some embodiments, the injection volume is equal to or more than about 0.2 mL to an injection volume that is equal to or less than about 1.6 mL. In an embodiment, the injection volume is equal to or more than about 0.3 mL to an injection volume that is equal to or less than about 1.4 mL. Also provided are embodiments wherein injection volume is equal to or more than about 0.4 mL to an injection volume that is equal to or less than about 1.2 mL. In an embodiment, the injection volume is equal to or more than about 0.5 mL to an injection volume that is equal to or less than about 1 mL. In one embodiment is a formulation, including a compound of Formula II such as polidocanol, or a pharmaceutically acceptable or cosmetically acceptable salt or others suitable form thereof wherein the injection volume is equal to about 0.1 mL. In certain embodiments, the injection volume is equal to about 0.2 mL. In an embodiment, the injection volume is equal to about 0.5 mL. In some embodiments, the injection volume is equal to about 1 mL. In an embodiment, the injection volume is equal to about 2 mL.

In certain embodiments, greater than 1% mg/ml of a compound of Formula I or Formula II, including polidocanol and polidocanol-like compounds, or a pharmaceutically acceptable or cosmetically acceptable salt or other suitable form thereof is provided as a sterile aqueous solution of at least 5 ml to provide adequate coverage area upon administration to an animal, including a human. In certain embodiments, less than 0.5 ml of the solution is injected in a plurality of locations into subcutaneous fat. For example, in one embodiment, the plurality of injections are spaced approximately from about 1 to 5 centimeters apart and form a grid like pattern over the fat treatment area, such as the submentum. In another embodiment, at least greater than 50 mg of a compound of Formula I or Formula II, including polidocanol and polidocanol-like compounds, or a pharmaceutically acceptable or cosmetically acceptable salt or other suitable form thereof in 5 ml water for injection with up to 10% (v/v) of an alcohol having 3 to 6 carbon atoms adjusted to a pH of 6.5-8.0 using disodium hydrogen phosphate dehydrate, potassium dihydrogen phosphate, or other suitable buffering agent. In further or additional embodiments, an alcohol having 3 to 6 carbon atoms is replaced at 0.1-10% (v/v) with other solubulizers such as glycerin or cyclodextrins to improve injection tolerability. Alternative pH buffering agents may include citric acid, sodium bicarbonate, sodium phosphate, and the like. In some embodiments, the formulation includes a compound that is suitable for adjusting pH of the formulation as a solution to provide greater stability of the formulation during storage and prior to administration to a patient. For example, in certain embodiments the pH is adjusted to be in the range of from about 4-12, or from about 5-11, or from about 6-10, from about 6 to 8.5, from about 6.5-8, or from about 7-9.

In some embodiments, the formulations described herein are injectable by means of subcutaneous injection. Subcutaneous administration has the benefit of local, targeted administration. Unlike other systemic modes of administration, subcutaneous administration results in a localized distribution of the active agents. In certain embodiments, these injectable formulations include a compound of Formula I or Formula II (e.g., polidocanol) (e.g., polidocanol) or a pharmaceutically acceptable or cosmetically acceptable salt or other suitable form thereof in an injection volume that is from about 0.01 mL to about 100 mL, and each volume in between this range, and further including ranges from about 0.01 mL to about 100 mL, 0.5 mL to about 50 mL, from about 1 mL to about 25 mL, from about 2 mL to about 20 mL, from about 3 mL to about 10 mL.

In some embodiments, the injectable formulation includes a compound of Formula I or Formula II (e.g., polidocanol) or a pharmaceutically acceptable or cosmetically acceptable salt or other suitable form thereof in an injection volume that is equal to or less than about 2 mL. In embodiments, the injection volume is about 0.05 mL to about 2 mL. In embodiments, the injection volume is about 0.1 mL to about 1.8 mL. In embodiments, the injection volume is about 0.2 mL to about 1.6 mL. In embodiments, the injection volume is about 0.3 mL to about 1.4 mL. In embodiments, the injection volume is about 0.4 mL to about 1.2 mL. In embodiments, the injection volume is about 0.5 mL to about 1 mL. In embodiments, the injection volume is about 0.1 mL. In embodiments, the injection volume is about 0.2 mL. In embodiments, the injection volume is about 0.5 mL. In embodiments, the injection volume is about 1 mL. In embodiments, the injection volume is about 2 mL.

In an aspect, provided is an injectable formulation for treating regional adipose tissue, regional adiposity, or regional fat accumulation including: an effective amount of at least one of a compound of Formula I or Formula II (e.g., polidocanol) or a pharmaceutically acceptable or cosmetically acceptable salt or other suitable form thereof; and a liquid carrier; the compound of Formula I or Formula II (e.g., polidocanol) or a pharmaceutically acceptable or cosmetically acceptable salt or other suitable form thereof and the liquid carrier formulated for injection into a layer of subcutaneous fat in a human in need.

In embodiments, the injection volume is less than about 2 mL. In embodiments, the injection volume is about 0.05 mL to about 2 mL. In embodiments, the injection volume is about 0.1 mL to about 1.8 mL. In embodiments, the injection volume is about 0.2 mL to about 1.6 mL. In embodiments, the injection volume is about 0.3 mL to about 1.4 mL. In embodiments, the injection volume is about 0.4 mL to about 1.2 mL. In embodiments, the injection volume is about 0.5 mL to about 1 mL. In embodiments, the injection volume is about 0.1 mL. In embodiments, the injection volume is about 0.2 mL. In embodiments, the injection volume is about 0.5 mL. In embodiments, the injection volume is about 1 mL. In embodiments, the injection volume is about 2 mL.

In certain embodiments, greater than 1% mg/ml of a compound of Formula I or Formula II, including polidocanol and polidocanol-like compounds, or a pharmaceutically acceptable or cosmetically acceptable salt or other suitable form thereof is provided as a sterile aqueous solution of at least 5 ml to provide adequate coverage area upon administration to an animal, including a human. In certain embodiments, less than 0.5 ml of the solution is injected in a plurality of locations into subcutaneous fat. For example, in one embodiment, the plurality of injections are spaced approximately from about 1 to 5 centimeters apart and form a grid like pattern over the fat treatment area, such as the submentum. In another embodiment, at least greater than 50 mg of a compound of Formula I or Formula II, including polidocanol and polidocanol-like compounds, or a pharmaceutically acceptable or cosmetically acceptable salt or other suitable form thereof in 5 ml water for injection with up to 10% (v/v) of an alcohol having 3 to 6 carbon atoms adjusted to a pH of 6.5-8.0 using disodium hydrogen phosphate dehydrate, potassium dihydrogen phosphate, or other suitable buffering agent. In further or additional embodiments, an alcohol having 3 to 6 carbon atoms is replaced at 0.1-10% (v/v) with other solubulizers such as PEG 300, PEG 400, Polysorbate (Tween) 80, Glycerin, cyclodextrins, or CREMOPHOR® to improve injection tolerability. Alternative pH buffering agents may include citric acid, sodium bicarbonate, sodium phosphate, and the like. In some embodiments, the formulation includes a compound that is suitable for adjusting pH of the formulation as a solution to provide greater stability of the formulation during storage and prior to administration to a patient. For example, in certain embodiments the pH is adjusted to be in the range of from about 4-12, or from about 5-11, or from about 6-10, from about 6 to 8.5, from about 6.5-8, or from about 7-9.

In some embodiments, the formulations described herein are injectable by means of subcutaneous injection. Subcutaneous administration has the benefit of local, targeted administration. Unlike other systemic modes of administration, subcutaneous administration results in a localized distribution of the active agents. In certain embodiments, these injectable formulations include a compound of Formula I or Formula II (e.g., polidocanol) (e.g., polidocanol) or a pharmaceutically acceptable or cosmetically acceptable salt or other suitable form thereof in an injection volume that is from 0.01 mL to 100 mL, and each volume in between this range, and further including ranges from 0.01 mL to 100 mL, 0.5 mL to 50 mL, from 1 mL to 25 mL, from 2 mL to 20 mL, from 3 mL to 10 mL.

In some embodiments, the injectable formulation includes a compound of Formula I or Formula II (e.g., polidocanol) or a pharmaceutically acceptable or cosmetically acceptable salt or other suitable form thereof in an injection volume that is equal to or less than 2 mL. In embodiments, the injection volume is 0.05 mL to 2 mL. In embodiments, the injection volume is 0.1 mL to 1.8 mL. In embodiments, the injection volume is 0.2 mL to 1.6 mL. In embodiments, the injection volume is 0.3 mL to 1.4 mL. In embodiments, the injection volume is 0.4 mL to 1.2 mL. In embodiments, the injection volume is 0.5 mL to 1 mL. In embodiments, the injection volume is 0.1 mL. In embodiments, the injection volume is 0.2 mL. In embodiments, the injection volume is 0.5 mL. In embodiments, the injection volume is 1 mL. In embodiments, the injection volume is 2 mL.

In an aspect, provided is an injectable formulation for treating regional adipose tissue, regional adiposity, or regional fat accumulation including: an effective amount of at least one of a compound of Formula I or Formula II (e.g., polidocanol) or a pharmaceutically acceptable or cosmetically acceptable salt or other suitable form thereof; and a liquid carrier; the compound of Formula I or Formula II (e.g., polidocanol) or a pharmaceutically acceptable or cosmetically acceptable salt or other suitable form thereof and the liquid carrier formulated for injection into a layer of subcutaneous fat in a human in need.

In embodiments, the injection volume is less than 2 mL. In embodiments, the injection volume is 0.05 mL to 2 mL. In embodiments, the injection volume is 0.1 mL to 1.8 mL. In embodiments, the injection volume is 0.2 mL to 1.6 mL. In embodiments, the injection volume is 0.3 mL to 1.4 mL. In embodiments, the injection volume is 0.4 mL to 1.2 mL. In embodiments, the injection volume is 0.5 mL to 1 mL. In embodiments, the injection volume is 0.1 mL. In embodiments, the injection volume is 0.2 mL. In embodiments, the injection volume is 0.5 mL. In embodiments, the injection volume is 1 mL. In embodiments, the injection volume is 2 mL.

In certain embodiments, greater than 1% mg/ml of a compound of Formula I or Formula II, including polidocanol and polidocanol-like compounds, or a pharmaceutically acceptable or cosmetically acceptable salt or other suitable form thereof is provided as a sterile aqueous solution of at least 5 ml to provide adequate coverage area upon administration to an animal, including a human. In certain embodiments, less than 0.5 ml of the solution is injected in a plurality of locations into subcutaneous fat. For example, in one embodiment, the plurality of injections are spaced from 1 to 5 centimeters apart and form a grid like pattern over the fat treatment area, such as the submentum. In another embodiment, at least greater than 50 mg of a compound of Formula I or Formula II, including polidocanol and polidocanol-like compounds, or a pharmaceutically acceptable or cosmetically acceptable salt or other suitable form thereof in 5 ml water for injection with up to 10% (v/v) of an alcohol having 3 to 6 carbon atoms adjusted to a pH of 6.5-8.0 using disodium hydrogen phosphate dehydrate, potassium dihydrogen phosphate, or other suitable buffering agent. In further or additional embodiments, an alcohol having 3 to 6 carbon atoms is replaced at 0.1-10% (v/v) with other solubulizers such as PEG 300, PEG 400, Polysorbate (Tween) 80, Glycerin, cyclodextrins, or CREMOPHOR® to improve injection tolerability. Alternative pH buffering agents may include citric acid, sodium bicarbonate, sodium phosphate, and the like. In some embodiments, the formulation includes a compound that is suitable for adjusting pH of the formulation as a solution to provide greater stability of the formulation during storage and prior to administration to a patient. For example, in certain embodiments the pH is adjusted to be in the range of from 4-12, or from 5-11, or from 6-10, from 6 to 8.5, from 6.5-8, or from 7-9.

Treatment Sites of Compounds of Formula I and II Including Polidocanol

In certain embodiments, the formulations described herein are administered or provided to the individual in the inside region of the knees, the middle to upper area of the upper arm (including the tricep area), the sub-mental area, the abdomen, the hips, the inner thigh, the outer thigh, the buttocks, the lower back, the upper back, or the chest.

In certain embodiments, the formulation is an extended release formulation. In certain other embodiments, the formulation is a rapid-release or immediate release formulation. In some embodiments, the therapeutically effective amount of the polidocanol is released for about 12 hours to about 45 days (e.g., about 3 days to about 10 days).

In some embodiments, the therapeutically effective amount of the polidocanol is released for 12 hours to 45 days (e.g., 3 days to 10 days).

In another aspect, provided herein are methods and formulations that facilitate dispersal of polidocanol, or a polidocanol-like compound of Formula II and salts and other suitable forms thereof into a layer of subcutaneous fat at a regional fat site selected from one or more of the following: a sub-mental region, an abdominal region, a waist, a hip, a lateral buttock, a thigh, a peri-orbital region and intramuscular region. In certain embodiments provided is a formulation for the treatment of one or more of: abdominal fat accumulation, regional adiposity, excessive adiposity in the sub-mental region, and exophthalmos caused by thyroid eye disease. In certain embodiments are provided formulations to affect a shape, contour, or appearance of the human body.

In some embodiments, the subject to be treated is provided a non-sustained release formulation. In some embodiments, the non-sustained release formulation, after a single dose, provides activity of the compound of Formula II such as polidocanol for a duration from about 4 hours to about 24 hours, e.g., about 6 hours, 8 hours, 10 hours, 12 hours, 16 hours, 18 hours, 21 hours, or any other duration of polidocanol from about four hours to about 24 hours. In some embodiments, the subject to be treated is provided a non-sustained release formulation. In some embodiments, the non-sustained release formulation, after a single dose, provides activity of the compound of Formula II such as polidocanol for a duration from 4 hours to 24 hours, e.g., 6 hours, 8 hours, 10 hours, 12 hours, 16 hours, 18 hours, 21 hours, or any other duration of polidocanol from four hours to 24 hours.

In another aspect provided herein are methods and formulations that facilitate dispersal of polidocanol, polidocanol-like compounds, and salts and other suitable forms thereof into a layer of subcutaneous fat at a regional fat site selected from one or more of the following: a sub-mental region, an abdominal region, a waist, a hip, a lateral buttock, a thigh, a peri-orbital region, an intra-orbital region, and intramuscular region, and combinations thereof. In certain embodiments, provided is a formulation for the treatment of one or more of: abdominal fat accumulation, regional adiposity, exophthalmos caused by thyroid eye disease, and excess adipose or fat tissue in the sub-mental region, which commonly presents as a double chin. In certain embodiments provided are formulations to affect a shape, contour, or appearance of the human body.

In embodiments, a pharmaceutical formulation as described herein (including in an aspect, embodiment, claim, example, table, or figure) is used in a method described herein (including in an aspect, embodiment, claim, example, table, or figure). In embodiments, an injectable formulation as described herein (including in an aspect, embodiment, claim, example, table, or figure) is used in a method described herein (including in an aspect, embodiment, claim, example, table, or figure). In embodiments, a formulation as described herein as described herein (including in an aspect, embodiment, claim, example, table, or figure) is used in a method described herein (including in an aspect, embodiment, claim, example, table, or figure). In embodiments, a composition (e.g., pharmaceutical composition, injectable composition) as described herein as described herein (including in an aspect, embodiment, claim, example, table, or figure) is used in a method described herein (including in an aspect, embodiment, claim, example, table, or figure).

Methods of Treatment

In an aspect is provided a method of reducing subcutaneous adipose tissue in a subject in need thereof, the method including administering to the subject a pharmaceutical formulation described herein.

In embodiments, reducing subcutaneous adipose tissue includes destroying fat cells (e.g., through apoptosis or necrosis or cell lysis induced directly by the pharmaceutical formulation or killing fat cells). In embodiments, reducing subcutaneous adipose tissue includes contouring an area of a subject (e.g., contouring a subcutaneous tissue(s) of the subject). In embodiments, contouring includes reducing the size of the area. In embodiments, reducing subcutaneous adipose tissue includes reducing the size (e.g., volume or mass) of the subcutaneous adipose tissue. In embodiments, reducing subcutaneous adipose tissue includes reducing the weight of the subcutaneous adipose tissue. In embodiments, reducing subcutaneous adipose tissue includes reducing the physical integrity (e.g., rigidity, shape, firmness, solidity, or density) of the subcutaneous adipose tissue. In embodiments, reducing subcutaneous adipose tissue includes reducing the subcutaneous adipose tissue in direct contact with the pharmaceutical formulation. In embodiments, reducing subcutaneous adipose tissue includes reducing the fat cells in direct contact with the pharmaceutical formulation. In embodiments, reducing subcutaneous adipose tissue includes reducing the subcutaneous adipose tissue into which the pharmaceutical formulation is administered. In embodiments, reducing subcutaneous adipose tissue includes reducing the subcutaneous adipose tissue substantially connected to the subcutaneous adipose tissue into which the pharmaceutical formulation is administered. In embodiments, reducing subcutaneous adipose tissue includes reducing the subcutaneous adipose tissue connected to the subcutaneous adipose tissue into which the pharmaceutical formulation is administered.

In embodiments, reducing subcutaneous adipose tissue consists essentially of destroying fat cells (e.g., through apoptosis or necrosis or cell lysis induced directly by the pharmaceutical formulation or killing fat cells). In embodiments, reducing subcutaneous adipose tissue consists essentially of contouring an area of a subject (e.g., contouring a subcutaneous tissue(s) of the subject). In embodiments, contouring consists essentially of reducing the size of the area. In embodiments, reducing subcutaneous adipose tissue consists essentially of reducing the size (e.g., volume or mass) of the subcutaneous adipose tissue. In embodiments, reducing subcutaneous adipose tissue consists essentially of reducing the weight of the subcutaneous adipose tissue. In embodiments, reducing subcutaneous adipose tissue consists essentially of reducing the physical integrity (e.g., rigidity, shape, firmness, solidity, or density) of the subcutaneous adipose tissue. In embodiments, reducing subcutaneous adipose tissue consists essentially of reducing the subcutaneous adipose tissue in direct contact with the pharmaceutical formulation. In embodiments, reducing subcutaneous adipose tissue consists essentially of reducing the fat cells in direct contact with the pharmaceutical formulation. In embodiments, reducing subcutaneous adipose tissue consists essentially of reducing the subcutaneous adipose tissue into which the pharmaceutical formulation is administered. In embodiments, reducing subcutaneous adipose tissue consists essentially of reducing the subcutaneous adipose tissue substantially connected to the subcutaneous adipose tissue into which the pharmaceutical formulation is administered. In embodiments, reducing subcutaneous adipose tissue consists essentially of reducing the subcutaneous adipose tissue connected to the subcutaneous adipose tissue into which the pharmaceutical formulation is administered.

In embodiments, reducing subcutaneous adipose tissue consists of destroying fat cells (e.g., through apoptosis or necrosis or cell lysis induced directly by the pharmaceutical formulation or killing fat cells). In embodiments, reducing subcutaneous adipose tissue consists of contouring an area of a subject (e.g., contouring a subcutaneous tissue(s) of the subject). In embodiments, contouring consists of reducing the size of the area. In embodiments, reducing subcutaneous adipose tissue consists of reducing the size (e.g., volume or mass) of the subcutaneous adipose tissue. In embodiments, reducing subcutaneous adipose tissue consists of reducing the weight of the subcutaneous adipose tissue. In embodiments, reducing subcutaneous adipose tissue consists of reducing the physical integrity (e.g., rigidity, shape, firmness, solidity, or density) of the subcutaneous adipose tissue. In embodiments, reducing subcutaneous adipose tissue consists of reducing the subcutaneous adipose tissue in direct contact with the pharmaceutical formulation. In embodiments, reducing subcutaneous adipose tissue consists of reducing the fat cells in direct contact with the pharmaceutical formulation. In embodiments, reducing subcutaneous adipose tissue consists of reducing the subcutaneous adipose tissue into which the pharmaceutical formulation is administered. In embodiments, reducing subcutaneous adipose tissue consists of reducing the subcutaneous adipose tissue substantially connected to the subcutaneous adipose tissue into which the pharmaceutical formulation is administered. In embodiments, reducing subcutaneous adipose tissue consists of reducing the subcutaneous adipose tissue connected to the subcutaneous adipose tissue into which the pharmaceutical formulation is administered.

In embodiments, reducing subcutaneous adipose tissue is reduction by greater than about 1% (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%). In embodiments, reducing subcutaneous adipose tissue is reduction by less than about 1% (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%). In embodiments, reducing subcutaneous adipose tissue is reduction by about 1% (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%)

In embodiments, reducing subcutaneous adipose tissue is reduction by greater than 1% (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%). In embodiments, reducing subcutaneous adipose tissue is reduction by less than 1% (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%). In embodiments, reducing subcutaneous adipose tissue is reduction by 1% (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%).

In embodiments, the pharmaceutical formulation is administered within a plurality of treatment sessions. In embodiments, each treatment session is spaced by at least 14 days. In embodiments, each treatment session is separated from another treatment session by at least 7 days. In embodiments, each treatment session is separated from another treatment session by at least 8 days. In embodiments, each treatment session is separated from another treatment session by at least 9 days. In embodiments, each treatment session is separated from another treatment session by at least 10 days. In embodiments, each treatment session is separated from another treatment session by at least 11 days. In embodiments, each treatment session is separated from another treatment session by at least 12 days. In embodiments, each treatment session is separated from another treatment session by at least 13 days. In embodiments, each treatment session is separated from another treatment session by at least 14 days. In embodiments, each treatment session is separated from another treatment session by at least 15 days. In embodiments, each treatment session is separated from another treatment session by at least 16 days. In embodiments, each treatment session is separated from another treatment session by at least 17 days. In embodiments, each treatment session is separated from another treatment session by at least 18 days. In embodiments, each treatment session is separated from another treatment session by at least 19 days. In embodiments, each treatment session is separated from another treatment session by at least 20 days. In embodiments, each treatment session is separated from another treatment session by at least 21 days. In embodiments, each treatment session is separated from another treatment session by at least 22 days. In embodiments, each treatment session is separated from another treatment session by at least 23 days. In embodiments, each treatment session is separated from another treatment session by at least 24 days. In embodiments, each treatment session is separated from another treatment session by at least 25 days. In embodiments, each treatment session is separated from another treatment session by at least 26 days. In embodiments, each treatment session is separated from another treatment session by at least 27 days. In embodiments, each treatment session is separated from another treatment session by at least 28 days. In embodiments, each treatment session is separated from another treatment session by at least 29 days. In embodiments, each treatment session is separated from another treatment session by at least 30 days. In embodiments, each treatment session is separated from another treatment session by at least 31 days. In embodiments, each treatment session is separated from another treatment session by at least four weeks. In embodiments, each treatment session is separated from another treatment session by at least five weeks. In embodiments, each treatment session is separated from another treatment session by at least six weeks. In embodiments, each treatment session is separated from another treatment session by at least seven weeks. In embodiments, each treatment session is separated from another treatment session by at least eight weeks. In embodiments, each treatment session is separated from another treatment session by at least one month. In embodiments, each treatment session is separated from another treatment session by at least two months. In embodiments, each treatment session is separated from another treatment session by at least three months. In embodiments, each treatment session is separated from another treatment session by at least four months. In embodiments, each treatment session is separated from another treatment session by at least five months. In embodiments, each treatment session is separated from another treatment session by at least six months. In embodiments, each treatment session is separated from another treatment session by at least nine months. In embodiments, each treatment session is separated from another treatment session by at least one year.

In embodiments, the pharmaceutical formulation is administered within a plurality of treatment sessions. In embodiments, each treatment session is spaced by about 14 days. In embodiments, each treatment session is separated from another treatment session by about 7 days. In embodiments, each treatment session is separated from another treatment session by about 8 days. In embodiments, each treatment session is separated from another treatment session by about 9 days. In embodiments, each treatment session is separated from another treatment session by about 10 days. In embodiments, each treatment session is separated from another treatment session by about 11 days. In embodiments, each treatment session is separated from another treatment session by about 12 days. In embodiments, each treatment session is separated from another treatment session by about 13 days. In embodiments, each treatment session is separated from another treatment session by about 14 days. In embodiments, each treatment session is separated from another treatment session by about 15 days. In embodiments, each treatment session is separated from another treatment session by about 16 days. In embodiments, each treatment session is separated from another treatment session by about 17 days. In embodiments, each treatment session is separated from another treatment session by about 18 days. In embodiments, each treatment session is separated from another treatment session by about 19 days. In embodiments, each treatment session is separated from another treatment session by about 20 days. In embodiments, each treatment session is separated from another treatment session by about 21 days. In embodiments, each treatment session is separated from another treatment session by about 22 days. In embodiments, each treatment session is separated from another treatment session by about 23 days. In embodiments, each treatment session is separated from another treatment session by about 24 days. In embodiments, each treatment session is separated from another treatment session by about 25 days. In embodiments, each treatment session is separated from another treatment session by about 26 days. In embodiments, each treatment session is separated from another treatment session by about 27 days. In embodiments, each treatment session is separated from another treatment session by about 28 days. In embodiments, each treatment session is separated from another treatment session by about 29 days. In embodiments, each treatment session is separated from another treatment session by about 30 days. In embodiments, each treatment session is separated from another treatment session by about 31 days. In embodiments, each treatment session is separated from another treatment session by about four weeks. In embodiments, each treatment session is separated from another treatment session by about five weeks. In embodiments, each treatment session is separated from another treatment session by about six weeks. In embodiments, each treatment session is separated from another treatment session by about seven weeks. In embodiments, each treatment session is separated from another treatment session by about eight weeks. In embodiments, each treatment session is separated from another treatment session by about one month. In embodiments, each treatment session is separated from another treatment session by about two months. In embodiments, each treatment session is separated from another treatment session by about three months. In embodiments, each treatment session is separated from another treatment session by about four months. In embodiments, each treatment session is separated from another treatment session by about five months. In embodiments, each treatment session is separated from another treatment session by about six months. In embodiments, each treatment session is separated from another treatment session by about nine months. In embodiments, each treatment session is separated from another treatment session by about one year.

In embodiments, each treatment session includes administering a plurality of subcutaneous injections of the pharmaceutical formulation into adipose tissue of the subject. In embodiments, the plurality of subcutaneous injections is about 2. In embodiments, the plurality of subcutaneous injections is about 3. In embodiments, the plurality of subcutaneous injections is about 4. In embodiments, the plurality of subcutaneous injections is about 5. In embodiments, the plurality of subcutaneous injections is about 6. In embodiments, the plurality of subcutaneous injections is about 7. In embodiments, the plurality of subcutaneous injections is about 8. In embodiments, the plurality of subcutaneous injections is about 9. In embodiments, the plurality of subcutaneous injections is about 10. In embodiments, the plurality of subcutaneous injections is about 15. In embodiments, the plurality of subcutaneous injections is about 20. In embodiments, the plurality of subcutaneous injections is about 25. In embodiments, the plurality of subcutaneous injections is about 30.

In embodiments, each treatment session includes administering a plurality of subcutaneous injections of the pharmaceutical formulation into adipose tissue of the subject. In embodiments, the plurality of subcutaneous injections is 2. In embodiments, the plurality of subcutaneous injections is 3. In embodiments, the plurality of subcutaneous injections is 4. In embodiments, the plurality of subcutaneous injections is 5. In embodiments, the plurality of subcutaneous injections is 6. In embodiments, the plurality of subcutaneous injections is 7. In embodiments, the plurality of subcutaneous injections is 8. In embodiments, the plurality of subcutaneous injections is 9. In embodiments, the plurality of subcutaneous injections is 10. In embodiments, the plurality of subcutaneous injections is 15. In embodiments, the plurality of subcutaneous injections is 20. In embodiments, the plurality of subcutaneous injections is 25. In embodiments, the plurality of subcutaneous injections is 30. In embodiments, the plurality of subcutaneous injections is about 2, 3, 4, 5, 6, 7, 8, 9, 10, 11, 12, 13, 14, 15, 16, 17, 18, 19, 20, 21, 22, 23, 24, 25, 26, 27, 28, 29, or 30. In embodiments, the plurality of subcutaneous injections is 2, 3, 4, 5, 6, 7, 8, 9, 10, 11, 12, 13, 14, 15, 16, 17, 18, 19, 20, 21, 22, 23, 24, 25, 26, 27, 28, 29, or 30.

In embodiments, the administrating is subcutaneously administering.

In embodiments, the method locally reduces subcutaneous adipose tissue.

In embodiments, the administering includes a plurality of subcutaneous injections of the pharmaceutical formulation into adipose tissue of said subject. In embodiments, the plurality of subcutaneous injections is about 2, 3, 4, 5, 6, 7, 8, 9, 10, 11, 12, 13, 14, 15, 16, 17, 18, 19, 20, 21, 22, 23, 24, 25, 26, 27, 28, 29, or 30. In embodiments, the plurality of subcutaneous injections is 2, 3, 4, 5, 6, 7, 8, 9, 10, 11, 12, 13, 14, 15, 16, 17, 18, 19, 20, 21, 22, 23, 24, 25, 26, 27, 28, 29, or 30.

In embodiments, the plurality of subcutaneous injections are spaced about 0.1 cm apart. In embodiments, the plurality of subcutaneous injections are spaced about 0.2 cm apart. In embodiments, the plurality of subcutaneous injections are spaced about 0.3 cm apart. In embodiments, the plurality of subcutaneous injections are spaced about 0.4 cm apart. In embodiments, the plurality of subcutaneous injections are spaced about 0.5 cm apart. In embodiments, the plurality of subcutaneous injections are spaced about 0.6 cm apart. In embodiments, the plurality of subcutaneous injections are spaced about 0.7 cm apart. In embodiments, the plurality of subcutaneous injections are spaced about 0.8 cm apart. In embodiments, the plurality of subcutaneous injections are spaced about 0.9 cm apart. In embodiments, the plurality of subcutaneous injections are spaced about 1.0 cm apart. In embodiments, the plurality of subcutaneous injections are spaced about 1.5 cm apart. In embodiments, the plurality of subcutaneous injections are spaced about 2.0 cm apart. In embodiments, the plurality of subcutaneous injections are spaced about 2.5 cm apart. In embodiments, the plurality of subcutaneous injections are spaced about 3.0 cm apart. In embodiments, the plurality of subcutaneous injections are spaced about 3.5 cm apart. In embodiments, the plurality of subcutaneous injections are spaced about 4.0 cm apart. In embodiments, the plurality of subcutaneous injections are spaced about 4.5 cm apart. In embodiments, the plurality of subcutaneous injections are spaced about 5.0 cm apart. In embodiments, the plurality of subcutaneous injections are spaced about 10.0 cm apart.

In embodiments, the plurality of subcutaneous injections are spaced 0.1 cm apart. In embodiments, the plurality of subcutaneous injections are spaced 0.2 cm apart. In embodiments, the plurality of subcutaneous injections are spaced 0.3 cm apart. In embodiments, the plurality of subcutaneous injections are spaced 0.4 cm apart. In embodiments, the plurality of subcutaneous injections are spaced 0.5 cm apart. In embodiments, the plurality of subcutaneous injections are spaced 0.6 cm apart. In embodiments, the plurality of subcutaneous injections are spaced 0.7 cm apart. In embodiments, the plurality of subcutaneous injections are spaced 0.8 cm apart. In embodiments, the plurality of subcutaneous injections are spaced 0.9 cm apart. In embodiments, the plurality of subcutaneous injections are spaced 1.0 cm apart. In embodiments, the plurality of subcutaneous injections are spaced 1.5 cm apart. In embodiments, the plurality of subcutaneous injections are spaced 2.0 cm apart. In embodiments, the plurality of subcutaneous injections are spaced 2.5 cm apart. In embodiments, the plurality of subcutaneous injections are spaced 3.0 cm apart. In embodiments, the plurality of subcutaneous injections are spaced 3.5 cm apart. In embodiments, the plurality of subcutaneous injections are spaced 4.0 cm apart. In embodiments, the plurality of subcutaneous injections are spaced 4.5 cm apart. In embodiments, the plurality of subcutaneous injections are spaced 5.0 cm apart. In embodiments, the plurality of subcutaneous injections are spaced 10.0 cm apart.

In embodiments, the plurality of subcutaneous injections are spaced an average of about 0.1 cm apart. In embodiments, the plurality of subcutaneous injections are spaced an average of about 0.2 cm apart. In embodiments, the plurality of subcutaneous injections are spaced an average of about 0.3 cm apart. In embodiments, the plurality of subcutaneous injections are spaced an average of about 0.4 cm apart. In embodiments, the plurality of subcutaneous injections are spaced an average of about 0.5 cm apart. In embodiments, the plurality of subcutaneous injections are spaced an average of about 0.6 cm apart. In embodiments, the plurality of subcutaneous injections are spaced an average of about 0.7 cm apart. In embodiments, the plurality of subcutaneous injections are spaced an average of about 0.8 cm apart. In embodiments, the plurality of subcutaneous injections are spaced an average of about 0.9 cm apart. In embodiments, the plurality of subcutaneous injections are spaced an average of about 1.0 cm apart. In embodiments, the plurality of subcutaneous injections are spaced an average of about 1.5 cm apart. In embodiments, the plurality of subcutaneous injections are spaced an average of about 2.0 cm apart. In embodiments, the plurality of subcutaneous injections are spaced an average of about 2.5 cm apart. In embodiments, the plurality of subcutaneous injections are spaced an average of about 3.0 cm apart. In embodiments, the plurality of subcutaneous injections are spaced an average of about 3.5 cm apart. In embodiments, the plurality of subcutaneous injections are spaced an average of about 4.0 cm apart. In embodiments, the plurality of subcutaneous injections are spaced an average of about 4.5 cm apart. In embodiments, the plurality of subcutaneous injections are spaced an average of about 5.0 cm apart. In embodiments, the plurality of subcutaneous injections are spaced an average of about 10.0 cm apart.

In embodiments, the plurality of subcutaneous injections are spaced an average of 0.1 cm apart. In embodiments, the plurality of subcutaneous injections are spaced an average of 0.2 cm apart. In embodiments, the plurality of subcutaneous injections are spaced an average of 0.3 cm apart. In embodiments, the plurality of subcutaneous injections are spaced an average of 0.4 cm apart. In embodiments, the plurality of subcutaneous injections are spaced an average of 0.5 cm apart. In embodiments, the plurality of subcutaneous injections are spaced an average of 0.6 cm apart. In embodiments, the plurality of subcutaneous injections are spaced an average of 0.7 cm apart. In embodiments, the plurality of subcutaneous injections are spaced an average of 0.8 cm apart. In embodiments, the plurality of subcutaneous injections are spaced an average of 0.9 cm apart. In embodiments, the plurality of subcutaneous injections are spaced an average of 1.0 cm apart. In embodiments, the plurality of subcutaneous injections are spaced an average of 1.5 cm apart. In embodiments, the plurality of subcutaneous injections are spaced an average of 2.0 cm apart. In embodiments, the plurality of subcutaneous injections are spaced an average of 2.5 cm apart. In embodiments, the plurality of subcutaneous injections are spaced an average of 3.0 cm apart. In embodiments, the plurality of subcutaneous injections are spaced an average of 3.5 cm apart. In embodiments, the plurality of subcutaneous injections are spaced an average of 4.0 cm apart. In embodiments, the plurality of subcutaneous injections are spaced an average of 4.5 cm apart. In embodiments, the plurality of subcutaneous injections are spaced an average of 5.0 cm apart. In embodiments, the plurality of subcutaneous injections are spaced an average of 10.0 cm apart.

In embodiments, the method locally reduces submental adipose tissue.

In embodiments, the pharmaceutical formulation is administered in a volume of from about 0.1 cc to about 5.0 cc. In embodiments, the pharmaceutical formulation is administered in a volume of from about 1.0 cc to about 2.0 cc. In embodiments, the pharmaceutical formulation is administered in a volume of from about 0.1 cc to about 0.5 cc. In embodiments, the pharmaceutical formulation is administered in a volume of from about 0.2 cc to about 0.5 cc. In embodiments, the pharmaceutical formulation is administered in a volume of from about 0.3 cc to about 0.5 cc. In embodiments, the pharmaceutical formulation is administered in a volume of from about 0.4 cc to about 0.5 cc. In embodiments, the pharmaceutical formulation is administered in a volume of from about 0.1 cc to about 0.4 cc. In embodiments, the pharmaceutical formulation is administered in a volume of from about 0.1 cc to about 0.3 cc. In embodiments, the pharmaceutical formulation is administered in a volume of from about 0.1 cc to about 0.2 cc. In embodiments, the pharmaceutical formulation is administered in a volume of from about 0.1 cc to about 0.6 cc. In embodiments, the pharmaceutical formulation is administered in a volume of from about 0.1 cc to about 0.7 cc. In embodiments, the pharmaceutical formulation is administered in a volume of from about 0.1 cc to about 0.8 cc. In embodiments, the pharmaceutical formulation is administered in a volume of from about 0.1 cc to about 0.9 cc. In embodiments, the pharmaceutical formulation is administered in a volume of from about 0.1 cc to about 1.0 cc. In embodiments, the pharmaceutical formulation is administered in a volume of from about 0.3 cc to about 0.4 cc. In embodiments, the pharmaceutical formulation is administered in a volume of from about 0.2 cc to about 0.3 cc. In embodiments, the pharmaceutical formulation is administered in a volume of from about 0.2 cc to about 0.4 cc. In embodiments, the pharmaceutical formulation is administered in a volume of from about 0.2 cc to about 0.5 cc. In embodiments, the pharmaceutical formulation is administered in a volume of from about 0.2 cc to about 0.6 cc. In embodiments, the pharmaceutical formulation is administered in a volume of from about 0.2 cc to about 0.7 cc. In embodiments, the pharmaceutical formulation is administered in a volume of from about 0.2 cc to about 0.8 cc. In embodiments, the pharmaceutical formulation is administered in a volume of from about 0.2 cc to about 0.9 cc. In embodiments, the pharmaceutical formulation is administered in a volume of from about 0.2 cc to about 1.0 cc.

In embodiments, the pharmaceutical formulation is administered in a volume of about 0.1 cc. In embodiments, the pharmaceutical formulation is administered in a volume of about 0.2 cc. In embodiments, the pharmaceutical formulation is administered in a volume of about 0.3 cc. In embodiments, the pharmaceutical formulation is administered in a volume of about 0.4 cc. In embodiments, the pharmaceutical formulation is administered in a volume of about 0.5 cc. In embodiments, the pharmaceutical formulation is administered in a volume of about 0.6 cc. In embodiments, the pharmaceutical formulation is administered in a volume of about 0.7 cc. In embodiments, the pharmaceutical formulation is administered in a volume of about 0.8 cc. In embodiments, the pharmaceutical formulation is administered in a volume of about 0.9 cc. In embodiments, the pharmaceutical formulation is administered in a volume of about 1.0 cc. In embodiments, the pharmaceutical formulation is administered in a volume of about 2.0 cc. In embodiments, the pharmaceutical formulation is administered in a volume of about 3.0 cc. In embodiments, the pharmaceutical formulation is administered in a volume of about 4.0 cc. In embodiments, the pharmaceutical formulation is administered in a volume of about 5.0 cc.

In embodiments, the pharmaceutical formulation is administered in a volume of from 1.0 cc to 2.0 cc. In embodiments, the pharmaceutical formulation is administered in a volume of from 0.1 cc to 0.5 cc. In embodiments, the pharmaceutical formulation is administered in a volume of from 0.2 cc to 0.5 cc. In embodiments, the pharmaceutical formulation is administered in a volume of from 0.3 cc to 0.5 cc. In embodiments, the pharmaceutical formulation is administered in a volume of from 0.4 cc to 0.5 cc. In embodiments, the pharmaceutical formulation is administered in a volume of from 0.1 cc to 0.4 cc. In embodiments, the pharmaceutical formulation is administered in a volume of from 0.1 cc to 0.3 cc. In embodiments, the pharmaceutical formulation is administered in a volume of from 0.1 cc to 0.2 cc. In embodiments, the pharmaceutical formulation is administered in a volume of from 0.1 cc to 0.6 cc. In embodiments, the pharmaceutical formulation is administered in a volume of from 0.1 cc to 0.7 cc. In embodiments, the pharmaceutical formulation is administered in a volume of from 0.1 cc to 0.8 cc. In embodiments, the pharmaceutical formulation is administered in a volume of from 0.1 cc to 0.9 cc. In embodiments, the pharmaceutical formulation is administered in a volume of from 0.1 cc to 1.0 cc. In embodiments, the pharmaceutical formulation is administered in a volume of from 0.3 cc to 0.4 cc. In embodiments, the pharmaceutical formulation is administered in a volume of from 0.2 cc to 0.3 cc. In embodiments, the pharmaceutical formulation is administered in a volume of from 0.2 cc to 0.4 cc. In embodiments, the pharmaceutical formulation is administered in a volume of from 0.2 cc to 0.5 cc. In embodiments, the pharmaceutical formulation is administered in a volume of from 0.2 cc to 0.6 cc. In embodiments, the pharmaceutical formulation is administered in a volume of from 0.2 cc to 0.7 cc. In embodiments, the pharmaceutical formulation is administered in a volume of from 0.2 cc to 0.8 cc. In embodiments, the pharmaceutical formulation is administered in a volume of from 0.2 cc to 0.9 cc. In embodiments, the pharmaceutical formulation is administered in a volume of from 0.2 cc to 1.0 cc.

In embodiments, the pharmaceutical formulation is administered in a volume of 0.1 cc. In embodiments, the pharmaceutical formulation is administered in a volume of 0.2 cc. In embodiments, the pharmaceutical formulation is administered in a volume of 0.3 cc. In embodiments, the pharmaceutical formulation is administered in a volume of 0.4 cc. In embodiments, the pharmaceutical formulation is administered in a volume of 0.5 cc. In embodiments, the pharmaceutical formulation is administered in a volume of 0.6 cc. In embodiments, the pharmaceutical formulation is administered in a volume of 0.7 cc. In embodiments, the pharmaceutical formulation is administered in a volume of 0.8 cc. In embodiments, the pharmaceutical formulation is administered in a volume of 0.9 cc. In embodiments, the pharmaceutical formulation is administered in a volume of 1.0 cc. In embodiments, the pharmaceutical formulation is administered in a volume of 2.0 cc.

In embodiments, each individual administration (e.g., individual injection) of the pharmaceutical formulation is administered in a volume of from about 0.1 cc to about 5.0 cc. In embodiments, each individual administration (e.g., individual injection) of the pharmaceutical formulation is administered in a volume of from about 1.0 cc to about 2.0 cc. In embodiments, each individual administration (e.g., individual injection) of the pharmaceutical formulation is administered in a volume of from about 0.1 cc to about 0.5 cc. In embodiments, each individual administration (e.g., individual injection) of the pharmaceutical formulation is administered in a volume of from about 0.2 cc to about 0.5 cc. In embodiments, each individual administration (e.g., individual injection) of the pharmaceutical formulation is administered in a volume of from about 0.3 cc to about 0.5 cc. In embodiments, each individual administration (e.g., individual injection) of the pharmaceutical formulation is administered in a volume of from about 0.4 cc to about 0.5 cc. In embodiments, each individual administration (e.g., individual injection) of the pharmaceutical formulation is administered in a volume of from about 0.1 cc to about 0.4 cc. In embodiments, each individual administration (e.g., individual injection) of the pharmaceutical formulation is administered in a volume of from about 0.1 cc to about 0.3 cc. In embodiments, each individual administration (e.g., individual injection) of the pharmaceutical formulation is administered in a volume of from about 0.1 cc to about 0.2 cc. In embodiments, each individual administration (e.g., individual injection) of the pharmaceutical formulation is administered in a volume of from about 0.1 cc to about 0.6 cc. In embodiments, each individual administration (e.g., individual injection) of the pharmaceutical formulation is administered in a volume of from about 0.1 cc to about 0.7 cc. In embodiments, each individual administration (e.g., individual injection) of the pharmaceutical formulation is administered in a volume of from about 0.1 cc to about 0.8 cc. In embodiments, each individual administration (e.g., individual injection) of the pharmaceutical formulation is administered in a volume of from about 0.1 cc to about 0.9 cc. In embodiments, each individual administration (e.g., individual injection) of the pharmaceutical formulation is administered in a volume of from about 0.1 cc to about 1.0 cc. In embodiments, each individual administration (e.g., individual injection) of the pharmaceutical formulation is administered in a volume of from about 0.3 cc to about 0.4 cc. In embodiments, each individual administration (e.g., individual injection) of the pharmaceutical formulation is administered in a volume of from about 0.2 cc to about 0.3 cc. In embodiments, each individual administration (e.g., individual injection) of the pharmaceutical formulation is administered in a volume of from about 0.2 cc to about 0.4 cc. In embodiments, each individual administration (e.g., individual injection) of the pharmaceutical formulation is administered in a volume of from about 0.2 cc to about 0.5 cc. In embodiments, each individual administration (e.g., individual injection) of the pharmaceutical formulation is administered in a volume of from about 0.2 cc to about 0.6 cc. In embodiments, each individual administration (e.g., individual injection) of the pharmaceutical formulation is administered in a volume of from about 0.2 cc to about 0.7 cc. In embodiments, each individual administration (e.g., individual injection) of the pharmaceutical formulation is administered in a volume of from about 0.2 cc to about 0.8 cc. In embodiments, each individual administration (e.g., individual injection) of the pharmaceutical formulation is administered in a volume of from about 0.2 cc to about 0.9 cc. In embodiments, each individual administration (e.g., individual injection) of the pharmaceutical formulation is administered in a volume of from about 0.2 cc to about 1.0 cc.

In embodiments, each individual administration (e.g., individual injection) of the pharmaceutical formulation is administered in a volume of about 0.1 cc. In embodiments, each individual administration (e.g., individual injection) of the pharmaceutical formulation is administered in a volume of about 0.2 cc. In embodiments, each individual administration (e.g., individual injection) of the pharmaceutical formulation is administered in a volume of about 0.3 cc. In embodiments, each individual administration (e.g., individual injection) of the pharmaceutical formulation is administered in a volume of about 0.4 cc. In embodiments, each individual administration (e.g., individual injection) of the pharmaceutical formulation is administered in a volume of about 0.5 cc. In embodiments, each individual administration (e.g., individual injection) of the pharmaceutical formulation is administered in a volume of about 0.6 cc. In embodiments, each individual administration (e.g., individual injection) of the pharmaceutical formulation is administered in a volume of about 0.7 cc. In embodiments, each individual administration (e.g., individual injection) of the pharmaceutical formulation is administered in a volume of about 0.8 cc. In embodiments, each individual administration (e.g., individual injection) of the pharmaceutical formulation is administered in a volume of about 0.9 cc. In embodiments, each individual administration (e.g., individual injection) of the pharmaceutical formulation is administered in a volume of about 1.0 cc. In embodiments, each individual administration (e.g., individual injection) of the pharmaceutical formulation is administered in a volume of about 2.0 cc. In embodiments, each individual administration (e.g., individual injection) of the pharmaceutical formulation is administered in a volume of about 3.0 cc. In embodiments, each individual administration (e.g., individual injection) of the pharmaceutical formulation is administered in a volume of about 4.0 cc. In embodiments, each individual administration (e.g., individual injection) of the pharmaceutical formulation is administered in a volume of about 5.0 cc.

In embodiments, each individual administration (e.g., individual injection) of the pharmaceutical formulation is administered in a volume of from 0.1 cc to 0.5 cc. In embodiments, each individual administration (e.g., individual injection) of the pharmaceutical formulation is administered in a volume of from 0.2 cc to 0.5 cc. In embodiments, each individual administration (e.g., individual injection) of the pharmaceutical formulation is administered in a volume of from 0.3 cc to 0.5 cc. In embodiments, each individual administration (e.g., individual injection) of the pharmaceutical formulation is administered in a volume of from 0.4 cc to 0.5 cc. In embodiments, each individual administration (e.g., individual injection) of the pharmaceutical formulation is administered in a volume of from 0.1 cc to 0.4 cc. In embodiments, each individual administration (e.g., individual injection) of the pharmaceutical formulation is administered in a volume of from 0.1 cc to 0.3 cc. In embodiments, each individual administration (e.g., individual injection) of the pharmaceutical formulation is administered in a volume of from 0.1 cc to 0.2 cc. In embodiments, each individual administration (e.g., individual injection) of the pharmaceutical formulation is administered in a volume of from 0.1 cc to 0.6 cc. In embodiments, each individual administration (e.g., individual injection) of the pharmaceutical formulation is administered in a volume of from 0.1 cc to 0.7 cc. In embodiments, each individual administration (e.g., individual injection) of the pharmaceutical formulation is administered in a volume of from 0.1 cc to 0.8 cc. In embodiments, each individual administration (e.g., individual injection) of the pharmaceutical formulation is administered in a volume of from 0.1 cc to 0.9 cc. In embodiments, each individual administration (e.g., individual injection) of the pharmaceutical formulation is administered in a volume of from 0.1 cc to 1.0 cc. In embodiments, each individual administration (e.g., individual injection) of the pharmaceutical formulation is administered in a volume of from 0.3 cc to 0.4 cc. In embodiments, each individual administration (e.g., individual injection) of the pharmaceutical formulation is administered in a volume of from 0.2 cc to 0.3 cc. In embodiments, each individual administration (e.g., individual injection) of the pharmaceutical formulation is administered in a volume of from 0.2 cc to 0.4 cc. In embodiments, each individual administration (e.g., individual injection) of the pharmaceutical formulation is administered in a volume of from 0.2 cc to 0.5 cc. In embodiments, each individual administration (e.g., individual injection) of the pharmaceutical formulation is administered in a volume of from 0.2 cc to 0.6 cc. In embodiments, each individual administration (e.g., individual injection) of the pharmaceutical formulation is administered in a volume of from 0.2 cc to 0.7 cc. In embodiments, each individual administration (e.g., individual injection) of the pharmaceutical formulation is administered in a volume of from 0.2 cc to 0.8 cc. In embodiments, each individual administration (e.g., individual injection) of the pharmaceutical formulation is administered in a volume of from 0.2 cc to 0.9 cc. In embodiments, each individual administration (e.g., individual injection) of the pharmaceutical formulation is administered in a volume of from 0.2 cc to 1.0 cc.

In embodiments, each individual administration (e.g., individual injection) of the pharmaceutical formulation is administered in a volume of 0.1 cc. In embodiments, each individual administration (e.g., individual injection) of the pharmaceutical formulation is administered in a volume of 0.2 cc. In embodiments, each individual administration (e.g., individual injection) of the pharmaceutical formulation is administered in a volume of 0.3 cc. In embodiments, each individual administration (e.g., individual injection) of the pharmaceutical formulation is administered in a volume of 0.4 cc. In embodiments, each individual administration (e.g., individual injection) of the pharmaceutical formulation is administered in a volume of 0.5 cc. In embodiments, each individual administration (e.g., individual injection) of the pharmaceutical formulation is administered in a volume of 0.6 cc. In embodiments, each individual administration (e.g., individual injection) of the pharmaceutical formulation is administered in a volume of 0.7 cc. In embodiments, each individual administration (e.g., individual injection) of the pharmaceutical formulation is administered in a volume of 0.8 cc. In embodiments, each individual administration (e.g., individual injection) of the pharmaceutical formulation is administered in a volume of 0.9 cc. In embodiments, each individual administration (e.g., individual injection) of the pharmaceutical formulation is administered in a volume of 1.0 cc.

In embodiments, the pharmaceutical composition is supplied in a volume of about 0.1 cc to about 20.0 cc. In embodiments, the pharmaceutical composition is supplied in a volume of about 0.1 cc to about 15.0 cc. In embodiments, the pharmaceutical composition is supplied in a volume of about 0.1 cc to about 10.0 cc. In embodiments, the pharmaceutical composition is supplied in a volume of about 1.0 cc to about 20.0 cc. In embodiments, the pharmaceutical composition is supplied in a volume of about 1.0 cc to about 15.0 cc. In embodiments, the pharmaceutical composition is supplied in a volume of about 1.0 cc to about 10.0 cc. In embodiments, the pharmaceutical composition is supplied in a volume of about 0.1 cc to about 20.0 cc. In embodiments, the pharmaceutical composition is supplied in a volume of about 5.0 cc. In embodiments, the pharmaceutical composition is supplied in a volume of about 6.0 cc. In embodiments, the pharmaceutical composition is supplied in a volume of about 7.0 cc. In embodiments, the pharmaceutical composition is supplied in a volume of about 8.0 cc. In embodiments, the pharmaceutical composition is supplied in a volume of about 9.0 cc. In embodiments, the pharmaceutical composition is supplied in a volume of about 10.0 cc. In embodiments, the pharmaceutical composition is supplied in a volume of about 11.0 cc. In embodiments, the pharmaceutical composition is supplied in a volume of about 12.0 cc. In embodiments, the pharmaceutical composition is supplied in a volume of about 13.0 cc. In embodiments, the pharmaceutical composition is supplied in a volume of about 14.0 cc. In embodiments, the pharmaceutical composition is supplied in a volume of about 15.0 cc. In embodiments, the pharmaceutical composition is supplied in a volume of about 16.0 cc. In embodiments, the pharmaceutical composition is supplied in a volume of about 17.0 cc. In embodiments, the pharmaceutical composition is supplied in a volume of about 18.0 cc. In embodiments, the pharmaceutical composition is supplied in a volume of about 19.0 cc. In embodiments, the pharmaceutical composition is supplied in a volume of about 20.0 cc.

In embodiments of the method, the pharmaceutical formulation includes polidocanol. In embodiments of the method, the pharmaceutical formulation consists primarily of polidocanol. In embodiments of the method, the pharmaceutical formulation consists of polidocanol.

In embodiments of the method, the pharmaceutical formulation includes a co-solvent. In embodiments the co-solvent is a $C_3$-$C_6$ alcohol as described herein. In embodiments the co-solvent is propylene glycol. In embodiments, the co-solvent reduces polidocanol crystallization (e.g., relative to control, for example relative to the absence of the co-solvent). In embodiments, the co-solvent increases polidocanol solubilization (e.g., relative to control, for example relative to the absence of the co-solvent).

In embodiments, the co-solvent increases the uniformity of reduction of subcutaneous adipose tissue by polidocanol in the affected area (e.g., relative to control, for example relative to the absence of the co-solvent). In embodiments, the co-solvent decreases patchiness of subcutaneous adipose tissue reduction by polidocanol in the affected area (e.g., relative to control, for example relative to the absence of the co-solvent). In embodiments, the co-solvent increases evenness of subcutaneous adipose tissue reduction by polidocanol in the affected area (e.g., relative to control, for example relative to the absence of the co-solvent).

In embodiments, the co-solvent increases the uniformity of reduction of subcutaneous adipose tissue by the pharmaceutical formulation in the affected area (e.g., relative to control, for example relative to the absence of the co-solvent). In embodiments, the co-solvent decreases patchiness of subcutaneous adipose tissue reduction by the pharmaceutical formulation in the affected area (e.g., relative to control, for example relative to the absence of the co-solvent). In embodiments, the co-solvent increases evenness of subcutaneous adipose tissue reduction by the pharmaceutical formulation in the affected area (e.g., relative to control, for example relative to the absence of the co-solvent).

In embodiments, the co-solvent increases the uniformity of necrosis of adipocytes (fat cells) by polidocanol in the affected area (e.g., relative to control, for example relative to the absence of the co-solvent). In embodiments, the co-solvent increases the uniformity of adipocyte (fat cell) destruction (e.g., by apoptosis, necrosis, or lysis) by polidocanol in the affected area (e.g., relative to control, for example relative to the absence of the co-solvent). In embodiments, the co-solvent increases evenness of adipocyte (fat cell) necrosis by polidocanol in the affected area (e.g., relative to control, for example relative to the absence of the co-solvent). In embodiments, the co-solvent increases evenness of adipocyte (fat cell) destruction (e.g., by apoptosis, necrosis, or lysis) by polidocanol in the affected area (e.g., relative to control, for example relative to the absence of the co-solvent).

In embodiments, the co-solvent increases the uniformity of necrosis of adipocytes (fat cells) by the pharmaceutical formulation in the affected area (e.g., relative to control, for example relative to the absence of the co-solvent). In embodiments, the co-solvent increases the uniformity of adipocyte (fat cell) destruction (e.g., by apoptosis, necrosis, or lysis) by the pharmaceutical formulation in the affected area (e.g., relative to control, for example relative to the absence of the co-solvent). In embodiments, the co-solvent increases evenness of adipocyte (fat cell) necrosis by the pharmaceutical formulation in the affected area (e.g., relative to control, for example relative to the absence of the co-solvent). In embodiments, the co-solvent increases evenness of adipocyte (fat cell) destruction (e.g., by apoptosis, necrosis, or lysis) by the pharmaceutical formulation in the affected area (e.g., relative to control, for example relative to the absence of the co-solvent).

In as aspect is provided a method of reducing subcutaneous adipose tissue in a subject in need thereof, the method including administering to the subject a pharmaceutical formulation including polidocanol and a co-solvent, where the pharmaceutical formulation is administered within a plurality of treatment sessions, wherein each treatment session is spaced by at least 14 days.

In embodiments, each treatment session is spaced by at least 28 days.

In an aspect, provided herein are one or more methods described herein to reduce fat deposits under the eye, chin, or arm, as well as the buttock, calf, back, thigh, ankle, or stomach of a mammal. In another embodiment, the methods described herein reduce specific types of fat deposits such as eyelid fat herniation, lipomas, lipodystrophy, buffalo hump lipodystrophy, or fat deposits associated with cellulite. In another embodiment, the method reduces fat associated with fat redistribution syndrome, eyelid fat herniation, lipomas, Dercum's disease, lipodystrophy, buffalo hump lipodystrophy, dorsocervical fat, visceral adiposity, breast enlargement, hyperadiposity, diffused body fat around trunk and arms, and fat deposits associated with cellulite.

Provided herein are methods of selective, ablative and/or non-ablative fat reduction in an individual in need, the method including: administering to the individual an effective amount of a formulation described herein. Also provided herein are methods of treating a lipoma in an individual, the methods including subcutaneously administering or providing to the individual a formulation described herein. Described herein are adipolytic compositions and formulations, non-invasive methods and systems, and kits for body contouring, including reducing, emulsifying, and/or eliminating subcutaneous adipose tissue, including fat deposits.

In an aspect, provided herein is a method for increasing muscle mass in a subject in need thereof, including administering to the subject a sustained release or rapid release formulation described herein.

In an aspect is provided a method for local fat reduction is provided.

The method may include administering an effective amount of polidocanol. The polidocanol may contain a mixture of C12 alkyl ethoxylate homologues wherein at least about 10% (e.g. at least about 15%) of the mixture of C12 alkyl ethoxylate homologues has an HLB from about 10 to about 15. The polidocanol may be provided in a formulation with a co-solvent, for example propylene glycol. The polidocanol may contain a mixture of C12 alkyl ethoxylate homologues wherein at least 10% (e.g. at least 15%) of the mixture of C12 alkyl ethoxylate homologues has an HLB from 10 to 15. The polidocanol may be provided in a formulation with a co-solvent, for example propylene glycol.

In embodiments, the polidocanol provided herein is chromatographically pure. In other embodiments, the polidocanol is not chromatographically pure.

The method may include administering an effective amount of polidocanol (e.g. subcutaneously). The polidocanol may be at a concentration greater than 0.1% and less than 1.5%. The polidocanol may be formulated with a co-solvent such as propylene glycol. In embodiments, the administration frequency is not less than 14 days (e.g., not less than 28 days).

The polidocanol may be at a concentration less than about 1.5%. The volume may be less than about 0.5 cc per injection. The polidocanol may be at a concentration less than 1.5%. The volume may be less than 0.5 cc per injection. The polidocanol may be formulated with a co-solvent such as propylene glycol. In embodiments, the administration frequency is not less than 14 days (e.g., not less than 28 days).

In embodiments, substantial fat destruction of an inguinal fat deposit is accomplished using a concentration of polidocanol less than about 2.0%. In embodiments, substantial fat destruction of the inguinal fat deposit is accomplished using a concentration of polidocanol less than about 1.75%. In embodiments, substantial fat destruction of the inguinal fat deposit is accomplished using a concentration of polidocanol less than about 1.5%. In embodiments, substantial fat destruction of the inguinal fat deposit is accomplished using a concentration of polidocanol less than about 1.4%. In embodiments, substantial fat destruction of the inguinal fat deposit is accomplished using a concentration of polidocanol less than about 1.3%. In embodiments, substantial fat destruction of the inguinal fat deposit is accomplished using a concentration of polidocanol less than about 1.25%. In embodiments, substantial fat destruction of the inguinal fat deposit is accomplished using a concentration of polidocanol less than about 1.2%. In embodiments, substantial fat destruction of the inguinal fat deposit is accomplished using a concentration of polidocanol less than about 1.1%. In embodiments, substantial fat destruction of the inguinal fat deposit is accomplished using a concentration of polidocanol less than about 1.0%. In embodiments, substantial fat destruction of the inguinal fat deposit is accomplished using a concentration of polidocanol less than about 0.9%. In embodiments, substantial fat destruction of the inguinal fat deposit is accomplished using a concentration of polidocanol less than about 0.8%. In embodiments, substantial fat destruction of the inguinal fat deposit is accomplished using a concentration of polidocanol less than about 0.7%. In embodiments, substantial fat destruction of the inguinal fat deposit is accomplished using a concentration of polidocanol less than about 0.6%.

In embodiments, substantial fat destruction of an inguinal fat deposit is accomplished using a concentration of polidocanol less than 2.0%. In embodiments, substantial fat destruction of the inguinal fat deposit is accomplished using a concentration of polidocanol less than 1.75%. In embodiments, substantial fat destruction of the inguinal fat deposit is accomplished using a concentration of polidocanol less than 1.5%. In embodiments, substantial fat destruction of the inguinal fat deposit is accomplished using a concentration of polidocanol less than 1.4%. In embodiments, substantial fat destruction of the inguinal fat deposit is accomplished using a concentration of polidocanol less than 1.3%. In embodiments, substantial fat destruction of the inguinal fat deposit is accomplished using a concentration of polidocanol less than 1.25%. In embodiments, substantial fat destruction of the inguinal fat deposit is accomplished using a concentration of polidocanol less than 1.2%. In embodiments, substantial fat destruction of the inguinal fat deposit is accomplished using a concentration of polidocanol less than 1.1%. In embodiments, substantial fat destruction of the inguinal fat deposit is accomplished using a concentration of polidocanol less than 1.0%. In embodiments, substantial fat destruction of the inguinal fat deposit is accomplished using a concentration of polidocanol less than 0.9%. In embodiments, substantial fat destruction of the inguinal fat deposit is accomplished using a concentration of polidocanol less than 0.8%. In embodiments, substantial fat destruction of the inguinal fat deposit is accomplished using a concentration of polidocanol less than 0.7%. In embodiments, substantial fat destruction of the inguinal fat deposit is accomplished using a concentration of polidocanol less than 0.6%.

In embodiments, substantial fat destruction of the inguinal fat deposit is accomplished using a concentration of polidocanol from about 0.1% to about 1.5%. In embodiments, substantial fat destruction of the inguinal fat deposit is accomplished using a concentration of polidocanol from about 0.2% to about 1.5%. In embodiments, substantial fat destruction of the inguinal fat deposit is accomplished using a concentration of polidocanol from about 0.3% to about 1.5%. In embodiments, substantial fat destruction of the inguinal fat deposit is accomplished using a concentration of polidocanol from about 0.4% to about 1.5%. In embodiments, substantial fat destruction of the inguinal fat deposit is accomplished using a concentration of polidocanol from about 0.5% to about 1.5%. %.

In embodiments, substantial fat destruction of the inguinal fat deposit is accomplished using a concentration of polidocanol from 0.1% to 1.5%. In embodiments, substantial fat destruction of the inguinal fat deposit is accomplished using a concentration of polidocanol from 0.2% to 1.5%. In embodiments, substantial fat destruction of the inguinal fat deposit is accomplished using a concentration of polidocanol from 0.3% to 1.5%. In embodiments, substantial fat destruction of the inguinal fat deposit is accomplished using a concentration of polidocanol from 0.4% to 1.5%. In embodiments, substantial fat destruction of the inguinal fat deposit is accomplished using a concentration of polidocanol from 0.5% to 1.5%. %.

In embodiments, substantial fat destruction of the inguinal fat deposit is accomplished using a concentration of polidocanol from about 0.1% to about 1.25%. In embodiments, substantial fat destruction of the inguinal fat deposit is accomplished using a concentration of polidocanol from about 0.2% to about 1.25%. In embodiments, substantial fat destruction of the inguinal fat deposit is accomplished using a concentration of polidocanol from about 0.3% to about 1.25%. In embodiments, substantial fat destruction of the inguinal fat deposit is accomplished using a concentration of polidocanol from about 0.4% to about 1.25%. In embodiments, substantial fat destruction of the inguinal fat deposit is accomplished using a concentration of polidocanol from about 0.5% to about 1.25%.

In embodiments, substantial fat destruction of the inguinal fat deposit is accomplished using a concentration of polidocanol from 0.1% to 1.25%. In embodiments, substantial fat destruction of the inguinal fat deposit is accomplished using a concentration of polidocanol from 0.2% to 1.25%. In embodiments, substantial fat destruction of the inguinal fat deposit is accomplished using a concentration of polidocanol from 0.3% to 1.25%. In embodiments, substantial fat destruction of the inguinal fat deposit is accomplished using a concentration of polidocanol from 0.4% to 1.25%. In embodiments, substantial fat destruction of the inguinal fat deposit is accomplished using a concentration of polidocanol from 0.5% to 1.25%.

In embodiments, substantial fat destruction of the inguinal fat deposit is accomplished using a concentration of polidocanol from about 0.1% to about 1.0%. In embodiments, substantial fat destruction of the inguinal fat deposit is accomplished using a concentration of polidocanol from about 0.2% to about 1.0%. In embodiments, substantial fat destruction of the inguinal fat deposit is accomplished using a concentration of polidocanol from about 0.3% to about 1.0%. In embodiments, substantial fat destruction of the inguinal fat deposit is accomplished using a concentration of polidocanol from about 0.4% to about 1.0%. In embodiments, substantial fat destruction of the inguinal fat deposit is accomplished using a concentration of polidocanol from about 0.5% to about 1.0%.

In embodiments, substantial fat destruction of the inguinal fat deposit is accomplished using a concentration of polidocanol from 0.1% to 1.0%. In embodiments, substantial fat destruction of the inguinal fat deposit is accomplished using a concentration of polidocanol from 0.2% to 1.0%. In embodiments, substantial fat destruction of the inguinal fat deposit is accomplished using a concentration of polidocanol from 0.3% to 1.0%. In embodiments, substantial fat destruction of the inguinal fat deposit is accomplished using a concentration of polidocanol from 0.4% to 1.0%. In embodiments, substantial fat destruction of the inguinal fat deposit is accomplished using a concentration of polidocanol from 0.5% to 1.0%.

In embodiments, the polidocanol is the product of reacting 1 mole of the corresponding C12 alcohol with 9 moles of ethoxide equivalents under basic conditions (e.g. with a metal base such as potassium hydroxide). In related embodiments, the average number of ethoxylate units of the polidocanol is about 6. In related embodiments, the average number of ethoxylate units of the polidocanol is about 7. In related embodiments, the average number of ethoxylate units of the polidocanol is about 8. In related embodiments, the average number of ethoxylate units of the polidocanol is about 9. In related embodiments, the average number of ethoxylate units of the polidocanol is about 10. In related embodiments, the average molecular weight of the polidocanol is about 480 g/mol to about 620 g/mole. In related embodiments, the average molecular weight of the polidocanol is about 494 g/mol.

The method may include injecting an effective amount of polidocanol (e.g. in an aqueous formulation) into subcutaneous fat of a subject in need thereof. In embodiments, the polidocanal is administered less than once per day. In embodiments, the polidocanal is administered about once per week. In embodiments, the polidocanal is administered about once every 14 days (e.g. twice per month). In embodiments, the polidocanal is administered about once every 28 days (e.g. once per month). In embodiments, the polidocanal is administered once per week. In embodiments, the polidocanal is administered once every 14 days (e.g. twice per month). In embodiments, the polidocanal is administered once every 28 days (e.g. once per month). The injections may occur at no less than 14 day intervals (e.g., no less than 28 day intervals). In embodiments, the polidocanol is provided in a composition described herein (e.g. with a co-solvent such as propylene glycol).

In embodiments, the administration of polidocanol is provided in a manner that selectively destroys adipose cells relative to skin cells (e.g. dermal cells).

In an aspect is provided a method for treating adipose tissue including administering to a human or animal subject by subcutaneous injection a formulation including an effective amount, for example a therapeutically or cosmetically effective amount, of polidocanol and an alcohol having 3 to 6 carbon atoms (e.g., from about 0.5% W/V to about 10% W/V). In some embodiments, the alcohol having 3 to 6 carbon atoms is present in an amount of from about 1% W/V to about 5% W/V. In some embodiments, the alcohol having 3 to 6 carbon atoms is present in an amount of approximately 5% W/V. In some embodiments, the method includes treating adipose tissue including administering to a human or animal subject by subcutaneous injection a formulation including polidocanol in an amount that is greater than 1.0% W/V and from about 0.5% W/V to about 10% W/V of an alcohol having 3 to 6 carbon atoms. In some embodiments, the method includes treating adipose tissue including administering to a human or animal subject by subcutaneous injection a formulation including polidocanol in an amount from about 0.1% W/V to about 20.0% W/V and from about 0.5% W/V to about 10% W/V of an alcohol having 3 to 6 carbon atoms. In some embodiments, the method includes treating adipose tissue including administering to a human or animal subject by subcutaneous injection a formulation including polidocanol in an amount from about 0.5% W/V to about 10.0% W/V and from about 0.5% W/V to about 10% W/V of an alcohol having 3 to 6 carbon atoms. In some embodiments, the method includes treating adipose tissue including administering to a human or animal subject by subcutaneous injection a formulation including polidocanol in an amount from about 0.1% W/V to about 2.0% W/V and from about 0.5% W/V to about 10% W/V of an alcohol having 3 to 6 carbon atoms. In some embodiments, the method includes treating adipose tissue including administering to a human or animal subject by subcutaneous injection a formulation including polidocanol in an amount of about 0.5% W/V, 1.25%, or 2.0% W/V and from about 0.5% W/V to about 10% W/V of an alcohol having 3 to 6 carbon atoms. In some embodiments, the formulation has a pH of from about 6 to 9. In some embodiments, the formulation has a pH of from about 7 to 8.

In an aspect is provided a method for treating adipose tissue including administering to a human or animal subject by subcutaneous injection a formulation including an effective amount, for example a therapeutically or cosmetically effective amount, of polidocanol and an alcohol having 3 to 6 carbon atoms (e.g., from 0.5% W/V to 10% W/V). In some embodiments, the alcohol having 3 to 6 carbon atoms is present in an amount of from 1% W/V to 5% W/V. In some embodiments, the alcohol having 3 to 6 carbon atoms is present in an amount of approximately 5% W/V. In some embodiments, the method includes treating adipose tissue including administering to a human or animal subject by subcutaneous injection a formulation including polidocanol in an amount that is greater than 1.0% W/V and from 0.5% W/V to 10% W/V of an alcohol having 3 to 6 carbon atoms. In some embodiments, the method includes treating adipose tissue including administering to a human or animal subject by subcutaneous injection a formulation including polidocanol in an amount from 0.1% W/V to 20.0% W/V and from 0.5% W/V to 10% W/V of an alcohol having 3 to 6 carbon atoms. In some embodiments, the method includes treating adipose tissue including administering to a human or animal subject by subcutaneous injection a formulation including polidocanol in an amount from 0.5% W/V to 10.0% W/V and from 0.5% W/V to 10% W/V of an alcohol having 3 to 6 carbon atoms. In some embodiments, the method includes treating adipose tissue including administering to a human or animal subject by subcutaneous injection a formulation including polidocanol in an amount from 0.1% W/V to 2.0% W/V and from 0.5% W/V to 10% W/V of an alcohol having 3 to 6 carbon atoms. In some embodiments, the method includes treating adipose tissue including administering to a human or animal subject by subcutaneous injection a formulation including polidocanol in an amount of 0.5% W/V, 1.25%, or 2.0% W/V and from 0.5% W/V to 10% W/V of an alcohol having 3 to 6 carbon atoms. In some embodiments, the formulation has a pH of from 6 to 9. In some embodiments, the formulation has a pH of from 7 to 8.

In an aspect is provided a method for the reduction and/or prevention of subcutaneous adipose tissue including administering to a human or animal subject by subcutaneous injection polidocanol (e.g., wherein said administering is performed no more than once every 28 days). The polidocanol may be provided in an aqueous formulation. The formulation may be any appropriate composition described herein, including a composition with a co-solvent such as propylene glycol In as aspect is provided a method for the reduction and/or prevention of subcutaneous adipose tissue. In some embodiments, the method includes administering to a human or animal subject by subcutaneous injection a formulation including polidocanol in an amount of from about 0.5% W/V to 2.0% W/V and propylene glycol in an amount of from about 1% W/V to 5% W/V, wherein the formulation does not contain polyethylene glycol or poloxamers. In some embodiments, the method includes administering to a human or animal subject by subcutaneous injection a formulation including polidocanol in an amount of from about 0.5% W/V to 2.0% W/V and glycerine in an amount of from about 1% W/V to 5% W/V, wherein the formulation does not contain polyethylene glycol or poloxamers. In some embodiments, the method includes administering to a human or animal subject by subcutaneous injection a formulation including polidocanol in an amount of from 0.5% W/V to 2.0% W/V and propylene glycol in an amount of from 1% W/V to 5% W/V, wherein the formulation does not contain polyethylene glycol or poloxamers. In some embodiments, the method includes administering to a human or animal subject by subcutaneous injection a formulation including polidocanol in an amount of from 0.5% W/V to 2.0% W/V and glycerine in an amount of from 1% W/V to 5% W/V, wherein the formulation does not contain polyethylene glycol or poloxamers.

In as aspect is provided a method for treating adipose tissue including administering a formulations or composition described herein. In some embodiments, described herein are methods for treating adipose tissue including administering to a human or animal subject in need by subcutaneous injection a formulation including an effective amount, including for example a therapeutically or cosmetically effective amount, of polidocanol and from about 0.5% W/V to about 10% W/V of propylene glycol. In some embodiments, described herein are methods for treating adipose tissue including administering to a human or animal subject in need by subcutaneous injection a formulation including an effective amount, including for example a therapeutically or cosmetically effective amount, of polidocanol and from about 0.5% W/V to about 10% W/V of glycerine. In some embodiments, the methods for treating adipose tissue include administering to a human or animal subject in need by subcutaneous injection a formulation including an effective amount, including for example a therapeutically or cosmetically effective amount, of polidocanol and from about 0.5% W/V to about 10% W/V of propylene glycol wherein the formulation does not contain ethanol or an ether. In some embodiments, the methods for treating adipose tissue include administering to a human or animal subject in need by subcutaneous injection a formulation including an effective amount, including for example a therapeutically or cosmetically effective amount, of polidocanol and from about 0.5% W/V to about 10% W/V of glycerine wherein the formulation does not contain ethanol or an ether. In some embodiments, the methods for treating adipose tissue include administering to a human or animal subject in need by subcutaneous injection a formulation including an effective amount, including for example a therapeutically or cosmetically effective amount, of polidocanol and from about 0.5% W/V to about 10% W/V of propylene glycol wherein the formulation does not contain aliphatic polyethers, such as polyethylene glycol or poloxamers. In some embodiments, the methods for treating adipose tissue include administering to a human or animal subject in need by subcutaneous injection a formulation including an effective amount, including for example a therapeutically or cosmetically effective amount, of polidocanol and from about 0.5% W/V to about 10% W/V of glycerine wherein the formulation does not contain aliphatic polyethers, such as polyethylene glycol or poloxamers. In some embodiments, the formulations do not contain ethanol or an ether or aliphatic polyethers such as polyethylene glycol or poloxamers.

In some embodiments, described herein are methods for treating adipose tissue including administering to a human or animal subject in need by subcutaneous injection a formulation including an effective amount, including for example a therapeutically or cosmetically effective amount, of polidocanol and from 0.5% W/V to 10% W/V of propylene glycol. In some embodiments, described herein are methods for treating adipose tissue including administering to a human or animal subject in need by subcutaneous injection a formulation including an effective amount, including for example a therapeutically or cosmetically effective amount, of polidocanol and from 0.5% W/V to 10% W/V of glycerine. In some embodiments, the methods for treating adipose tissue include administering to a human or animal subject in need by subcutaneous injection a formulation including an effective amount, including for example a therapeutically or cosmetically effective amount, of polidocanol and from 0.5% W/V to 10% W/V of propylene glycol wherein the formulation does not contain ethanol or an ether. In some embodiments, the methods for treating adipose tissue include administering to a human or animal subject in need by subcutaneous injection a formulation including an effective amount, including for example a therapeutically or cosmetically effective amount, of polidocanol and from 0.5% W/V to 10% W/V of glycerine wherein the formulation does not contain ethanol or an ether. In some embodiments, the methods for treating adipose tissue include administering to a human or animal subject in need by subcutaneous injection a formulation including an effective amount, including for example a therapeutically or cosmetically effective amount, of polidocanol and from 0.5% W/V to 10% W/V of propylene glycol wherein the formulation does not contain aliphatic polyethers, such as polyethylene glycol or poloxamers. In some embodiments, the methods for treating adipose tissue include administering to a human or animal subject in need by subcutaneous injection a formulation including an effective amount, including for example a therapeutically or cosmetically effective amount, of polidocanol and from 0.5% W/V to 10% W/V of glycerine wherein the formulation does not contain aliphatic polyethers, such as polyethylene glycol or poloxamers. In some embodiments, the formulations do not contain ethanol or an ether or aliphatic polyethers such as polyethylene glycol or poloxamers.

In an aspect is provided a cosmetic or therapeutic method including subcutaneously administering or providing to a human a formulation including a compound of Formula I or Formula II or a pharmaceutically acceptable or cosmetically acceptable salt or other form suitable for administration and a liquid carrier that is formulated for injection into a layer of subcutaneous fat in or to a human in need. In an embodiment, a formulation including polidocanol of Formula II is administered to the human to treat a disease selected from one or more of: fat tissue, abdominal fat accumulation, regional adiposity, excess sub-mental fat, and exophthalmous due to thyroid eye disease. In certain embodiments, the formulation is provided to the human to affect a shape, contour, or appearance of the human body. In an embodiment, the shape, contour, or appearance is in a region of the body (e.g., the abdominal region or eye region of the human). In certain other embodiments, the formulation is administered or provided to the human subcutaneously as an abdominal, peri-orbital, intra-orbital, or sub-mental injection. In an embodiment, a formulation described herein is administered or provided to the human subcutaneously to an abdominal region, an ophthalmic region, or a sub-mental region. In certain embodiments of the cosmetic and/or therapeutic methods described herein, the formulation is administered or provided to the human in the inside region of the knees, the middle to upper area of the upper arm (including the tricep area), the sub-mental area (including the area under the chin, for example the wattle (which is understood to refer to the fleshy fold of skin in the sub-mental area of the human)), the abdomen, the hips, the inner thigh, the outer thigh, the buttocks, the lower back, the upper back, or the chest.

In as aspect is provided a method for treating fat accumulation including administering an injectable formulation including a compound of Formula I or Formula II or a pharmaceutically acceptable or cosmetically acceptable salt or other suitable form thereof and a liquid carrier that is formulated for injection into a layer of subcutaneous fat in a human in need. In certain embodiments is a method for treating a fat accumulation including administering an injectable formulation including polidocanol, or a polidocanol-like compound of Formula I or Formula II or a pharmaceutically acceptable or cosmetically acceptable salt or other suitable form thereof and a liquid carrier formulated for injection into a layer of subcutaneous fat in a human in need. Also provided are methods of treating regional adipose tissue including administering an injectable formulation including at least one compound of Formula I or Formula II or pharmaceutically acceptable or cosmetically acceptable salt or other suitable form, or combinations thereof and a liquid carrier formulated for injection into a layer of subcutaneous fat in a human in need. Also provided are methods of treating regional adipose tissue including administering an injectable formulation including polidocanol of Formula II or a pharmaceutically acceptable or cosmetically acceptable salt or other suitable form thereof and a liquid carrier formulated for injection into a layer of subcutaneous fat in a human in need. Also provided are methods of treating regional adiposity including administering an injectable formulation including polidocanol of Formula II or a pharmaceutically acceptable or cosmetically acceptable salt or other suitable form thereof and a liquid carrier formulated for injection into a layer of subcutaneous fat in a human in need.

In as aspect is provided a method including administering an injectable formulation including at least one of a compound of Formula I or Formula II or a pharmaceutically acceptable or cosmetically acceptable salt or other suitable form thereof, or combinations thereof and a liquid carrier formulated for injection into a layer of subcutaneous fat in a human in need, wherein administration results in emulsifying, necrosis, lysing or destroying one or more adipose cells. In an embodiment, provided is a method including administering an injectable formulation including polidocanol of Formula II or a pharmaceutically acceptable or cosmetically acceptable salt or other suitable form thereof and a liquid carrier formulated for injection into a layer of subcutaneous fat in a human in need, wherein the administration results in emulsifying, necrosis, lysing or destroying one or more adipose cells. In certain embodiments, the methods described herein further result in an accompanying inflammatory reaction that at least partially removes or decreases destroyed or lysed adipose cells.

Provided herein is a method including administering an injectable formulation including a compound of Formula I or Formula II such as polidocanol or a pharmaceutically acceptable or cosmetically acceptable salt or other suitable form thereof and a liquid carrier formulated for injection into a layer of subcutaneous fat in a human in need, wherein said administration results in selectively emulsifying, necrotizing, lysing or destroying one or more adipose cells while, in certain situations, leaving surrounding tissue largely unaffected.

In certain embodiments, provided is a formulation or composition including a compound of Formula I or Formula II (e.g., polidocanol) that provides one or more of the following: (a) a critical micelle concentration ("CMC") of less than about 5 millimolar; (b) an HLB value of from about 10 to about 15; and (c) is non-ionic. In some embodiments, these formulations are used for contacting fat tissue, abdominal fat accumulation, regional adiposity, excess submental fat, and exophthalmous (e.g., due to thyroid eye disease), and/or for emulsifying, necrotizing, lysing or destroying one or more adipose cells while, in certain situations, leaving surrounding tissue largely unaffected (e.g., unlysed or less lysed in comparison to the lysis of fat cells (e.g., percentage of lysed cells, number of lysed cells, degree of lysis of a tissue or cell population).

In certain embodiments, the compound is polidocanol. Also provided herein is a method of administration to subcutaneous tissue including contacting the subcutaneous tissue with a pharmaceutically effective amount of polidocanol, provided that the polidocanol is present in an amount of about 0.1%-10% W/V or about 0.1%-5% W/V. In some embodiments, the polidocanol is present in an amount of about 0.5%-3% W/V, or less than about 0.5% W/V, or less than about 1% W/V, or less than about 2% W/V, or less than about 3% W/V, or less than about 4% W/V, or less than about 5% W/V, or less than about 10% W/V. In further or additional embodiments, the polidocanol is present in an amount that is greater than 1% W/V, greater than 1.5% W/V, greater than 2% W/V, greater than 2.5% W/V, greater than 3% W/V, greater than 4% W/V, greater than 5% W/V, greater than 6% W/V, or is about 10% W/V.

In as aspect is provided a method of treating lipoma in an individual, including subcutaneously administering or providing to the individual a formulation described herein. In certain embodiments, the method of treating lipoma includes administering to the individual an effective amount, including for example a therapeutically or cosmetically effective amount, of a formulation including polidocanol or a polidocanol-like compound of Formula II, or a pharmaceutically acceptable or cosmetically acceptable salt or other suitable form thereof; and a liquid carrier; wherein the polidocanol or a pharmaceutically acceptable or cosmetically acceptable salt or other suitable form thereof and the liquid carrier are formulated for injection into a layer of subcutaneous fat in the individual in need thereof.

In another aspect, provided herein are methods and formulations that facilitate dispersal of compound of Formula I or Formula II such as polidocanol and salts and other suitable forms thereof into a layer of subcutaneous fat at a regional fat site selected from one or more of the following: a sub-mental region, an abdominal region, a waist, a hip, a lateral buttock, a thigh, a peri-orbital region, an intra-orbital region, and intramuscular region. In certain embodiments is a formulation for the treatment of one or more of: abdominal fat accumulation, regional adiposity, excessive adiposity in the sub-mental region, and exophthalmos caused by thyroid eye disease. In certain embodiments are provided formulations to affect a shape, contour, or appearance of the human body.

In an aspect, provided herein is a method of treating regional adipose tissue, regional adiposity, or regional fat accumulation in an individual, said method including administering to the individual an effective amount of a formulation including: at least one of a compound of Formula I or Formula II such as polidocanol or a pharmaceutically acceptable or cosmetically acceptable salt or other suitable form thereof; and a liquid carrier; wherein the compound of Formula I or Formula II or a pharmaceutically acceptable or cosmetically acceptable salt or other suitable form thereof and the liquid carrier are formulated for injection into a layer of subcutaneous fat in the individual in need thereof.

In as aspect is provided a method of selective, ablative and/or non-ablative fat reduction in an individual in need, said method including administering to said individual an effective amount of a formulation described herein. In as aspect is provided a method of treating a lipoma in an individual, said methods including subcutaneously administering or providing to the individual a formulation described herein.

In another aspect provided herein is a method for increasing muscle mass in a subject in need thereof, including administering to the subject a sustained release or rapid release or immediate release formulation described herein.

In as aspect is provided a method to reduce fat deposits adjacent (e.g., under, over, lateral to, near, forming part of) the eye, chin including the sub-mental region, arm, buttock, calf, back, thigh, ankle, or stomach of a mammal in need thereof. In another embodiment, the methods described herein reduce specific types of fat deposits such as eyelid fat herniation, lipomas, lipodystrophy, buffalo hump lipodystrophy, or fat deposits associated with cellulite.

In yet another aspect, provided is a cosmetic or therapeutic method including subcutaneously administering or providing to a human, including to the subcutaneous tissue of a human, a formulation for treating regional adipose tissue, regional adiposity, or regional fat accumulation including: an effective amount of a compound of Formula I or II such as polidocanol or a pharmaceutically acceptable or cosmetically acceptable salt or other suitable form thereof; and a liquid carrier; the polidocanol or a pharmaceutically acceptable or cosmetically acceptable salt or other suitable form thereof and the liquid carrier formulated for injection into a layer of subcutaneous fat in a human in need. In an embodiment, provided is a method wherein the formulation described herein is administered to the human to treat an indication selected from one or more of: abdominal adiposity, excessive sub-mental adiposity, regional adiposity, and exophthalmous due to thyroid eye disease. In one embodiment, the formulation is provided to the human by subcutaneous injection. In another embodiment, the formulation is provided to the human by transdermal application to the other skin of a patient. In some embodiments, provided is a cosmetic method wherein a formulation described herein is provided to the human to affect a shape, contour, or appearance of the human body. In certain embodiments, the shape, contour, or appearance is in a region of the body (e.g., the abdominal region, sub-mental region, or eye region of the human). In certain embodiments, a formulation described herein is administered or provided to the human subcutaneously as a peri-orbital, intra-orbital, or sub-mental injection. In an embodiment, a formulation described herein is administered or provided to the human subcutaneously to an abdominal region, an ophthalmic region, or a sub-mental region. In certain embodiments, a formulation described herein is administered or provided to the human in the inside region of the knees, the middle to upper area of the upper arm (including the triceps' area), the sub-mental area (including the area under the chin, for example the wattle (which is understood to refer to the fleshy fold of skin in the sub-mental area of the human)), the abdomen, the hips, the inner thigh, the outer thigh, the buttocks, the lower back, the upper back, or the chest.

In an additional aspect, provided herein is a method for treating a fat accumulation including administering an injectable formulation described herein. In an embodiment, provided is a method for treating regional adipose tissue, said method including the step of administering an injectable formulation including at least one compound of Formula II described herein. In a certain embodiments, provided is a method for treating regional adiposity including administering an injectable formulation including polidocanol described herein.

In another aspect, provided herein is a method including administering an injectable formulation including a compound of Formula I or Formula II described herein, that results in lysing or destroying one or more adipose cells.

In an aspect, provided is a method including administering an injectable formulation including polidocanol described herein, that results in selectively lysing or destroying one or more adipose cells while in certain applications leaving surrounding tissue largely unaffected.

In an aspect, provided herein is a method of treating regional adipose tissue, regional adiposity, or regional fat accumulation in an individual, said method including administering to the individual an effective amount of a formulation including: a compound of Formula I or Formula II such as polidocanol or a pharmaceutically acceptable or cosmetically acceptable salt or other suitable form thereof; and a liquid carrier; wherein the compound of Formula I or Formula II or a pharmaceutically acceptable or cosmetically acceptable salt or other suitable form thereof and the liquid carrier are formulated for injection into a layer of subcutaneous fat in the individual in need thereof.

In an aspect, provided herein is a method of selective, ablative and/or non-ablative fat reduction in an individual in need, said method including: administering to said individual an effective amount of a formulation including a compound of Formula I or Formula II such as polidocanol or a pharmaceutically acceptable or cosmetically acceptable salt or other suitable form thereof; and a liquid carrier; wherein the compound of Formula I or Formula II or a pharmaceutically acceptable or cosmetically acceptable salt or other suitable form thereof and the liquid carrier are formulated for injection into a layer of subcutaneous fat in the individual.

In certain embodiments, the formulations described herein are administered to an individual to treat an indication selected from one or more of: abdominal adiposity, regional adiposity, excessive sub-mental adipose tissue which often presents as a double chin, and exophthalmos due to thyroid eye disease. In certain embodiments, provided are formulations to affect a shape, contour, or appearance of the human body. In some embodiments are provided cosmetic methods and formulations wherein the formulation is administered or provided to the human subcutaneously as a peri-orbital, intra-orbital, or sub-mental injection. In certain embodiments, the formulations described herein are administered or provided to the individual subcutaneously to an abdominal region, an ophthalmic region, or a sub-mental region. In further or additional embodiments, the formulations described here are administered to the head region of a patient, including for example to address a need in the forehead area of the patient, a brow lift, a Crow's lift, a peri-orbital depression, a cheek enhancement, a nasal labial fold (also referred to as "smile lines"), the glabella, lip enhancement, or sub-mental fat.

Multiple injections over a region are applied to achieve a pharmaceutical or cosmetic effect. These injections may be spaced from 0.1 to up to 5 cm apart. A small volume per injection, less than 0.5 ml, may require spacing 1.0 cm or less, with larger volumes per injection allowing for larger spacing, such that 1.0 ml to 2.0 ml per injection may allow spacing of 1 cm or more and reduce the number of injections required to treat an area. Improving the cosmetic effect and reducing side effects may also be achieve by using larger per injection volume and a lower concentration (W/V) of polidocanol, a polidocanol like compound or a cosmetically acceptable salt. In certain embodiments, a 0.1-1.0% (W/V) with a 1 ml to per injection volume is provided to the desired cosmetic effect with fewer side effects.

In some embodiments, more than one treatment session of a certain region spaced 1-8 weeks apart is provided to achieve the desired pharmaceutical or cosmetic effect. In certain embodiments, the treatment is provided less frequently than once per day. In one treatment embodiment, five to twenty 0.1 to 1.0 ml injections spaced 0.1 cm to 1.0 cm apart of 0.1% to 10.0% weight/volume (as used herein, "W/V"), including about 0.5%, about 1.0%, about 1.5%, about 2.0%, about 2.5%, about 3.0%, about 3.5%, about 4.0%, about 4.5%, about 5.0%, about 5.5%, about 6.0%, about 6.5%, about 7.0%, about 7.5%, about 8.0%, about 8.5%, about 9.0%, about 9.5%, or about 10.0% of polidocanol, a polidocanol like, or cosmetically or pharmaceutically acceptable salt or other suitable form thereof, is injected into the sub-mental (under chin) region of a patient. In one treatment embodiment, five to twenty 0.1 to 1.0 ml injections spaced 0.1 cm to 1.0 cm apart of 0.1% to 10.0% weight/volume (as used herein, "W/V"), including 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, or 10.0% of polidocanol, a polidocanol like, or cosmetically or pharmaceutically acceptable salt or other suitable form thereof, is injected into the sub-mental (under chin) region of a patient. As an example, the treatment is repeated up to 6 times at two to four week intervals until the desired cosmetic effect is achieved. In another treatment embodiment, ten 0.2 ml injections spaced 0.5 cm apart of about 0.5%, about 1.0%, about 3.0%, about 5.0%, or about 10.0% weight/volume of polidocanol, or a polidocanol like compound, or cosmetically or pharmaceutically acceptable salts thereof, are injected into the sub-mental (under chin) region of a patient. In one embodiment, the treatment is repeated 4 times at 4 week intervals until the desired cosmetic effect is achieved. In another treatment embodiment, ten 0.2 ml injections spaced 1.0 cm apart of 1.0% weight/volume of polidocanol, a polidocanol like compound, or cosmetically or pharmaceutically acceptable salt or other suitable form thereof, is injected into the sub-mental (under chin) region of a patient. In one treatment embodiment, the treatment is repeated 4 times at 4 week intervals until the desired cosmetic effect is achieved. In still another treatment embodiment, ten 0.4 ml injections spaced 1.0 cm apart of 0.5% weight/volume of polidocanol, a polidocanol like compound, or cosmetically or pharmaceutically acceptable salt or other suitable form thereof, is injected into the sub-mental (under chin) region of a patient. For example, the treatment is repeated 4 times at 4 week intervals until the desired cosmetic effect is achieved. In another treatment embodiment, up to twenty 0.2 ml injections spaced 1.0 cm apart of 1.0% weight/volume of polidocanol, a polidocanol like compound, or cosmetically or pharmaceutically acceptable salt or other suitable form thereof, is injected into the sub-mental (under chin) region of a patient. The treatment is repeated up to 4 times at 4-week intervals until the desired cosmetic effect is achieved. The treatment is repeated up to 4 times at 4-week intervals until the desired cosmetic effect is achieved. In another still another treatment embodiment, up to twenty 0.2 ml injections spaced 1.0 cm apart of 0.5% weight/volume of polidocanol, a polidocanol like compound, or cosmetically or pharmaceutically acceptable salt or other suitable form thereof, is injected into the sub-mental (under chin) region of a patient. The treatment is repeated 4 times at 4 week intervals until the desired cosmetic effect is achieved.

Figure 3:
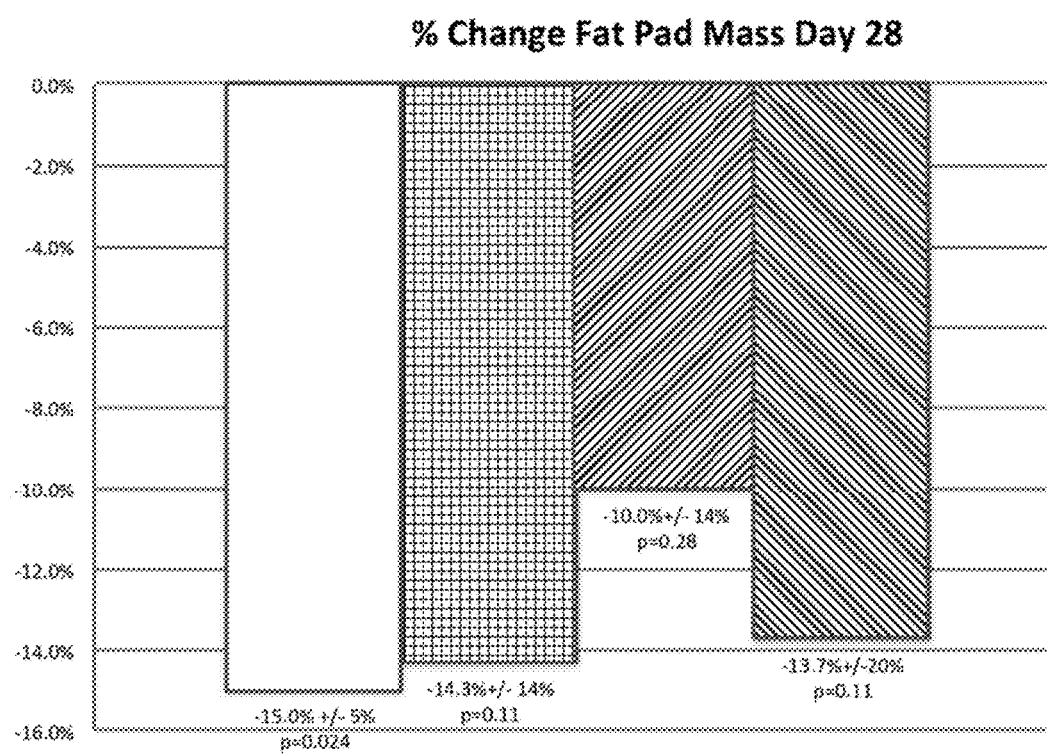
FIG. 3. Loss of fat pad mass at day 28 in 3 polidocanol treatment groups; Deoxycholate, the current standard for local fat reduction, was used as a positive control (left to right: 0.5% polidocanol, 1.25% polidocanol, 2.0% polidocanol, 1.0% deoxycholate).
Figure 4A:
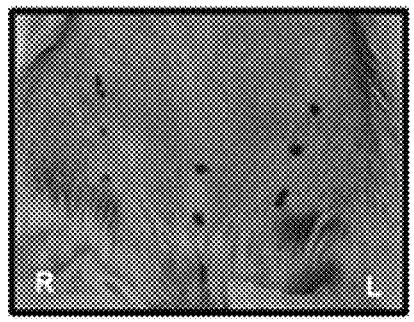
FIGS. 4A-4C. Dosing configuration with uniform infusion of a subcutaneous fat deposit (LVG Syrian Golden hamster, animal ID #312) using the formulation 2.5% propylene glycol and proposed treatment regimen of 0.2 cc spaced 5 cm apart, 3 injections per side for both sides.
Figure 4B:
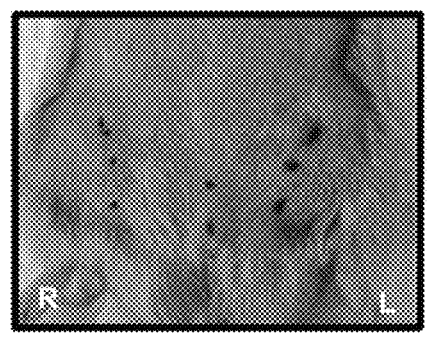
Figure 4C:
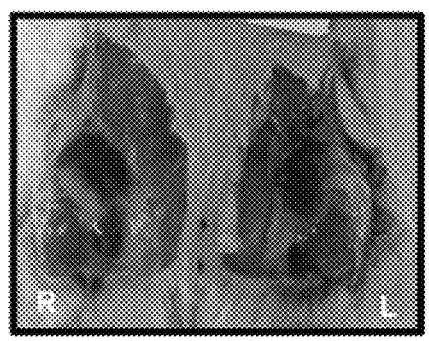
Figure 5A:
FIG. 5A-5B. Contouring effect of polidocanol injection shown as (FIG. 5A) loss of inguinal fat fullness and (FIG. 5B) enhancement of inguinal crease.
Figure 5B:
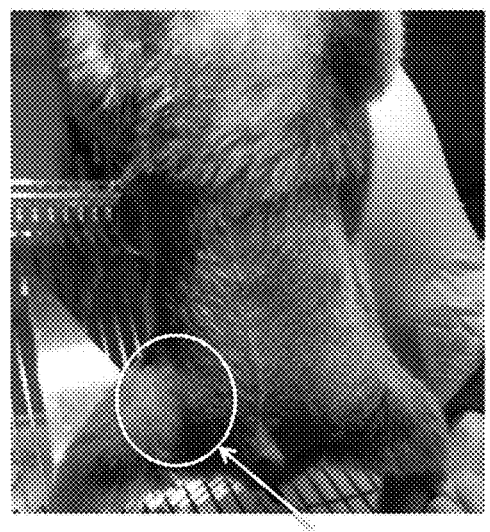

For example, reductions in inguinal fat pad mass of 15% were found at day 28 after a single treatment of polidocanol at doses of 0.5% and 1.25% (FIG. 3). Higher concentrations (2.0%) were shown to yield slightly less (10%) fat pad mass reductions. Thus, in embodiments, the polidoconal is administered approximately once per month and/or at concentrations less than about 2.0%. The treatment may employ about 0.1 to 0.3 ml (e.g. 0.2 ml) of a polidocanol at a concentration provided herein. In embodiments, the polidocanol is a concentration of from about 0.5% and 1.25%. The administration may be via injection. In embodiments, the injection is at a spacing of about 0.2 to 0.8 cm apart across the inguinal fat pad. Thus, in embodiments, the polidoconal is administered approximately once per month and/or at concentrations less than about 2.0%. The treatment may employ 0.1 to 0.3 ml (e.g. 0.2 ml) of a polidocanol at a concentration provided herein. In embodiments, the polidocanol is a concentration of from 0.5% and 1.25%. The administration may be via injection. In embodiments, the injection is at a spacing of 0.2 to 0.8 cm apart across the inguinal fat pad. In embodiments, the injection is at a spacing of about 0.5 cm apart across the inguinal fat pad (FIGS. 4A-4C). As shown in FIG. 3, the reductions in fat pad mass in this example were at least equivalent to deoxycholate administered at the same optimized dosing frequency, volume, and injection spacing. In addition, externally visible reduction in inguinal fat pad fullness was observed resulting in enhancement of the inguinal crease consistent with a benefit of visible changes in body contour (FIG. 5A-5B).

In an aspect, provided herein is a method of treating regional adipose tissue, regional adiposity, sub-mental adiposity, or regional fat accumulation in an individual, said method including administering to the individual an effective amount of a formulation including: at least one of a compound of Formula I or Formula II such as polidocanol or a pharmaceutically acceptable or cosmetically acceptable salt or other suitable form thereof; and a liquid carrier; wherein the compound of Formula I or Formula II or a pharmaceutically acceptable or cosmetically acceptable salt or other suitable form thereof and the liquid carrier are formulated for injection into a layer of subcutaneous fat in the individual in need thereof.

In embodiments, the administration of polidocanol is provided in a manner that selectively destroys adipose cell relative to skin cells (e.g. dermal cells). In FIGS. 4, 5A, 5B, 6, 7 and 8A-8C, it is shown that a polidocanol concentration greater than about 1.25% is associated with a higher proportion of side effects such as skin necrosis, inflammation, and the formation of large subcutaneous fat droplets that are slowly cleared from the body.

Figure 6:
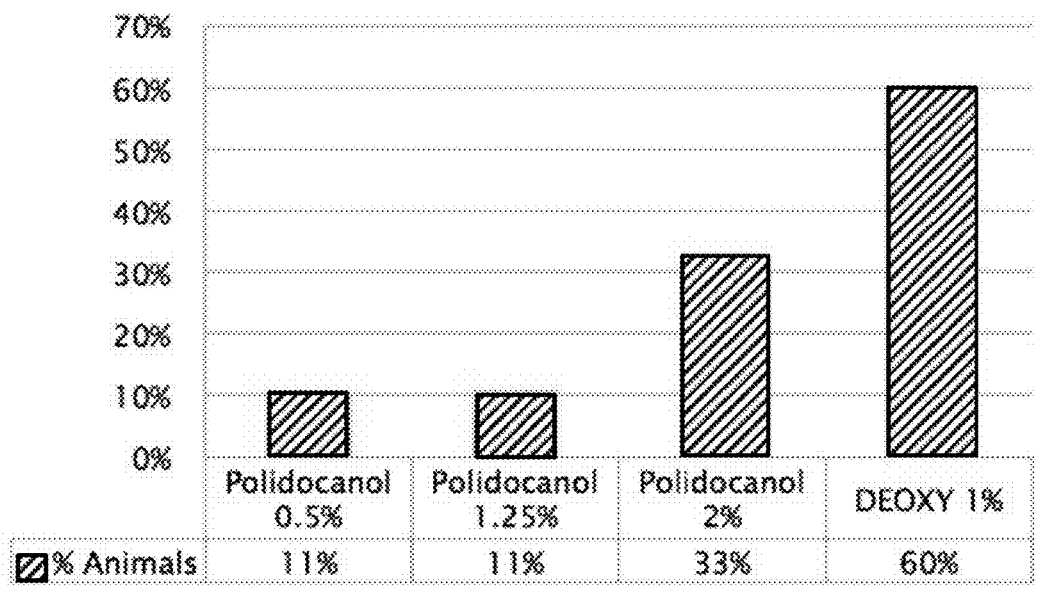
FIG. 6. Proportion of animals with skin necrosis in each group.
Figure 7:
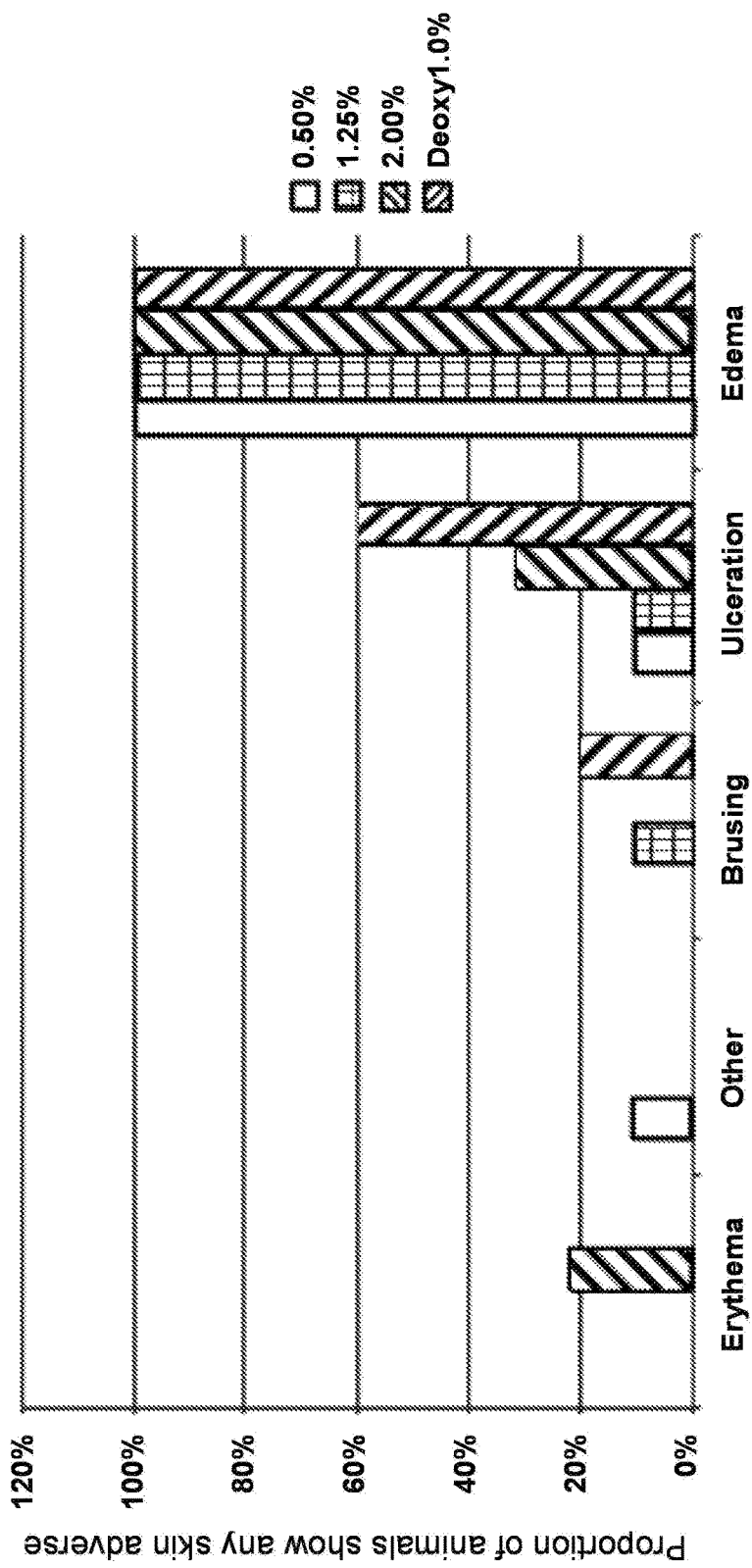
FIG. 7. Proportion of animals showing any skin adverse event. Histogram bins (left to right): erythema, other, bruising, ulceration, edema. With each bin (left to right): 0.50%, 1.25%, 2.00%, Deoxy 1.0%.
Figure 8A:
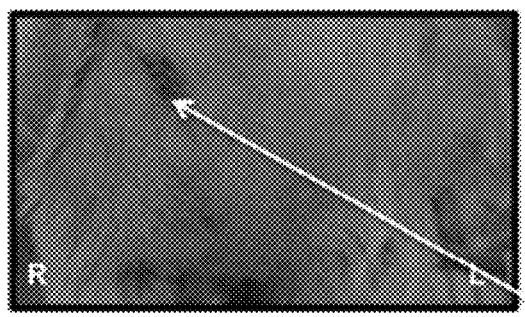
FIGS. 8A-8C. Documentation of skin necrosis side effect.
Figure 8B:
Figure 8C:
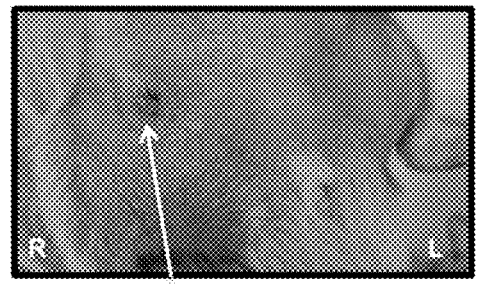

FIG. 6 shows that polidocanol selectively destroys fat tissue relative to skin tissue. When compared to the current detergent/surfactant standard for injectable subcutaneous fat destruction, deoxycholate (an ionic monomeric molecular species detergent), polidocanol injection at 0.5% and 1.25% resulted in 1 of 9 (11%) animals with mild skin breakdown whereas 3 of 5 (60%) of animals injected with 1% deoxycholate developed severe skin necrosis (FIG. 6). Moreover, 2% polidocanol produced less skin necrosis (33%) than deoxycholate. Thus, in embodiments, polidocanol is safer than deoxycholate for local fat reduction.

In some embodiments, in addition to treating a subject with any of the compositions described herein, a physician or other authorized medical caregiver prescribes a liposuction procedure to a subject, or performs a liposuction procedure on the subject to further reduce regional fat deposits.

In some embodiments, a liposuction procedure is performed on a subject to whom has been administered a composition including a therapeutically effective amount of a compound of Formula I or Formula II such as polidocanol or a pharmaceutically acceptable or cosmetically acceptable salt or other suitable form thereof. Without wishing to be bound by theory, administering any of the pharmaceutical and cosmetic compositions described herein to a subject prior to liposuction is likely to increase the efficacy of the liposuction procedure.

In embodiments, the method does not include administration of a lipase. In embodiments, the method does not include administration of a colipase.

In embodiments, the method includes a pharmaceutical formulation as described herein (including in an aspect, embodiment, claim, example, table, or figure). In embodiments, the method includes an injectable formulation as described herein (including in an aspect, embodiment, claim, example, table, or figure). In embodiments, the method includes a formulation as described herein (including in an aspect, embodiment, claim, example, table, or figure). In embodiments, the method includes a composition (e.g., a pharmaceutical composition, injectable composition) as described herein (including in an aspect, embodiment, claim, example, table, or figure).

Kits

In an aspect is provided a kit, including: a cosmetically or therapeutically effective amount, including for example a therapeutically or cosmetically effective amount, of a compound of Formula I or Formula II (e.g., polidocanol) or a pharmaceutically acceptable or cosmetically acceptable salt or other suitable form thereof; an injector; and instructions for use. In certain embodiments of the kit, the compound of Formula I or Formula II (e.g., polidocanol) or a pharmaceutically acceptable or cosmetically acceptable salt or other suitable form thereof is in an aqueous form. In certain embodiments of the kit, the polidocanol or a pharmaceutically acceptable or cosmetically acceptable salt or other suitable form thereof is in an aqueous form. In certain embodiments of the kit, the compound of Formula I or Formula II (e.g., polidocanol) or a pharmaceutically acceptable or cosmetically acceptable salt or other suitable form thereof is in crystalline phase. In certain other embodiments, the compound of Formula I or Formula II (e.g., polidocanol) or a pharmaceutically acceptable or cosmetically acceptable salt or other suitable form thereof is in an amorphous phase. In an embodiment, the compound of Formula I or Formula II (e.g., polidocanol) or a pharmaceutically acceptable or cosmetically acceptable salt or other suitable form thereof is in a semi-crystalline phase. In certain embodiments of the kit, the compound of Formula I or Formula II (e.g., polidocanol) or a pharmaceutically acceptable or cosmetically acceptable salt or other suitable form thereof is in a semi-amorphous phase. In some embodiments, a compound of Formula I or Formula II (e.g., polidocanol) or a pharmaceutically acceptable or cosmetically acceptable salt or other suitable form thereof is in a crystalline or amorphous form. In some embodiments of the kit described herein, the compound of Formula II is polidocanol. In certain embodiments of the kit, the injector contains a needle, is needleless, or includes a subcutaneous applicator.

In an aspect is provided a kit for treating adipose tissue including the described formulations and instructions for use. In some embodiments, described herein are kits for treating adipose tissue including a formulation including an effective amount, for example a therapeutically or cosmetically effective amount, of polidocanol and propylene glycol (e.g., from about 0.5% W/V to about 10% W/V) and instructions for use. In some embodiments, described herein are kits for treating adipose tissue including a formulation including an effective amount, for example a therapeutically or cosmetically effective amount, of polidocanol and glycerine (e.g., from about 0.5% W/V to about 10% W/V) and instructions for use. In some embodiments, the kits for treating adipose tissue include a formulation including an effective amount, for example a therapeutically or cosmetically effective amount, of polidocanol and propylene glycol (from about 0.5% W/V to about 10% W/V) wherein the formulation does not contain ethanol or an ether. In some embodiments, the kits for treating adipose tissue include a formulation including an effective amount, for example a therapeutically or cosmetically effective amount of polidocanol and glycerine (from about 0.5% W/V to about 10% W/V) wherein the formulation does not contain ethanol or an ether. In some embodiments, the kits for treating adipose tissue include a formulation including an effective amount, including for example a therapeutically or cosmetically effective amount, of polidocanol and propylene glycol (e.g., from about 0.5% W/V to about 10% W/V) wherein the formulation does not contain aliphatic polyethers, such as polyethylene glycol or poloxamers. In some embodiments, the kits for treating adipose tissue include a formulation including an effective amount, including for example a therapeutically or cosmetically effective amount, of polidocanol and glycerine (e.g., from about 0.5% W/V to about 10% W/V) wherein the formulation does not contain aliphatic polyethers, such as polyethylene glycol or poloxamers. In some embodiments, the formulations do not contain ethanol or an ether or aliphatic polyethers such as polyethylene glycol or poloxamers.

In an aspect is provided a kit for treating adipose tissue including the described formulations and instructions for use. In some embodiments, described herein are kits for treating adipose tissue including a formulation including an effective amount, for example a therapeutically or cosmetically effective amount, of polidocanol and propylene glycol (e.g., from 0.5% W/V to 10% W/V) and instructions for use. In some embodiments, described herein are kits for treating adipose tissue including a formulation including an effective amount, for example a therapeutically or cosmetically effective amount, of polidocanol and glycerine (e.g., from 0.5% W/V to 10% W/V) and instructions for use. In some embodiments, the kits for treating adipose tissue include a formulation including an effective amount, for example a therapeutically or cosmetically effective amount, of polidocanol and propylene glycol (from 0.5% W/V to 10% W/V) wherein the formulation does not contain ethanol or an ether. In some embodiments, the kits for treating adipose tissue include a formulation including an effective amount, for example a therapeutically or cosmetically effective amount of polidocanol and glycerine (from 0.5% W/V to 10% W/V) wherein the formulation does not contain ethanol or an ether. In some embodiments, the kits for treating adipose tissue include a formulation including an effective amount, including for example a therapeutically or cosmetically effective amount, of polidocanol and propylene glycol (e.g., from 0.5% W/V to 10% W/V) wherein the formulation does not contain aliphatic polyethers, such as polyethylene glycol or poloxamers. In some embodiments, the kits for treating adipose tissue include a formulation including an effective amount, including for example a therapeutically or cosmetically effective amount, of polidocanol and glycerine (e.g., from 0.5% W/V to 10% W/V) wherein the formulation does not contain aliphatic polyethers, such as polyethylene glycol or poloxamers. In some embodiments, the formulations do not contain ethanol or an ether or aliphatic polyethers such as polyethylene glycol or poloxamers.

In an aspect is provided a kit for treating adipose tissue including a formulation including an effective amount, for example a therapeutically or cosmetically effective amount, of polidocanol and an alcohol having 3 to 6 carbon atoms (e.g., from about 0.5% W/V to about 10% W/V) and instructions for use. In some embodiments, the alcohol having 3 to 6 carbon atoms is present in an amount of from about 1% W/V to about 5% W/V. In some embodiments, the alcohol having 3 to 6 carbon atoms is present in an amount of approximately 5% W/V. In some embodiments, the kit includes a formulation including polidocanol in an amount that is greater than 1.0% W/V and from about 0.5% W/V to about 10% W/V of an alcohol having 3 to 6 carbon atoms. In some embodiments, the kit includes a formulation including polidocanol in an amount from about 0.1% W/V to about 20.0% W/V and from about 0.5% W/V to about 10% W/V of an alcohol having 3 to 6 carbon atoms. In some embodiments, the kit includes a formulation including polidocanol in an amount from about 0.5% W/V to about 10.0% W/V and from about 0.5% W/V to about 10% W/V of an alcohol having 3 to 6 carbon atoms. In some embodiments, the kit includes a formulation including polidocanol in an amount from about 0.1% W/V to about 2.0% W/V and from about 0.5% W/V to about 10% W/V of an alcohol having 3 to 6 carbon atoms. In some embodiments, the kit includes a formulation including polidocanol in an amount of about 0.5% W/V, 1.25%, or 2.0% W/V and from about 0.5% W/V to about 10% W/V of an alcohol having 3 to 6 carbon atoms. In some embodiments, the formulation has a pH of from about 6 to 9. In some embodiments, the formulation has a pH of from about 7 to 8.

In an aspect is provided a kit for treating adipose tissue including a formulation including an effective amount, for example a therapeutically or cosmetically effective amount, of polidocanol and an alcohol having 3 to 6 carbon atoms (e.g., from 0.5% W/V to 10% W/V) and instructions for use. In some embodiments, the alcohol having 3 to 6 carbon atoms is present in an amount of from 1% W/V to 5% W/V. In some embodiments, the alcohol having 3 to 6 carbon atoms is present in an amount of 5% W/V. In some embodiments, the kit includes a formulation including polidocanol in an amount that is greater than 1.0% W/V and from 0.5% W/V to 10% W/V of an alcohol having 3 to 6 carbon atoms. In some embodiments, the kit includes a formulation including polidocanol in an amount from 0.1% W/V to 20.0% W/V and from 0.5% W/V to 10% W/V of an alcohol having 3 to 6 carbon atoms. In some embodiments, the kit includes a formulation including polidocanol in an amount from 0.5% W/V to 10.0% W/V and from 0.5% W/V to 10% W/V of an alcohol having 3 to 6 carbon atoms. In some embodiments, the kit includes a formulation including polidocanol in an amount from 0.1% W/V to 2.0% W/V and from 0.5% W/V to 10% W/V of an alcohol having 3 to 6 carbon atoms. In some embodiments, the kit includes a formulation including polidocanol in an amount of 0.5% W/V, 1.25%, or 2.0% W/V and from 0.5% W/V to 10% W/V of an alcohol having 3 to 6 carbon atoms. In some embodiments, the formulation has a pH of from 6 to 9. In some embodiments, the formulation has a pH of from 7 to 8.

In an aspect, provided herein is a kit, said kit including: a cosmetically or therapeutically effective amount of at least one of a compound of Formula I or Formula II such as polidocanol or a pharmaceutically acceptable or cosmetically acceptable salt or other suitable form thereof; an injector; and instructions for use. In certain embodiments, the kit includes polidocanol or a pharmaceutically acceptable or cosmetically acceptable salt or other suitable form thereof in an aqueous form. In some embodiments, the polidocanol or a pharmaceutically acceptable or cosmetically acceptable salt or other suitable form thereof is in crystalline phase. In an embodiment, the polidocanol or a pharmaceutically acceptable or cosmetically acceptable salt or other suitable form thereof is in an amorphous phase. In a certain embodiment, the polidocanol or a pharmaceutically acceptable or cosmetically acceptable salt or other suitable form thereof is in a semi-crystalline phase. In certain embodiments, the polidocanol or a pharmaceutically acceptable or cosmetically acceptable salt or other suitable form thereof is in a semi-amorphous phase. In an embodiment, the polidocanol or a pharmaceutically acceptable or cosmetically acceptable salt or other suitable form thereof is in a crystalline or amorphous form. In certain embodiments of the kit, the injector contains a needle, is needleless, or includes a subcutaneous applicator.

In certain embodiments, provided herein are kits, including: a cosmetically or therapeutically effective amount of polidocanol, a compound of Formula I, a compound of Formula II, a polidocanol-like compound of Formula II or a pharmaceutically acceptable or cosmetically acceptable salt or other suitable form thereof; an injector; and instructions for use. In embodiments, the kit does not include a lipase. In embodiments, the kit does not include a colipase.

While certain embodiments have been described, these embodiments have been presented by way of example only, and are not intended to limit the scope of the disclosure. The formulations, methods, and systems described herein may be embodied in a variety of other forms. Furthermore, various omissions, substitutions and changes in the form of the formulations, methods, and systems described herein may be made without departing from the spirit of this disclosure. The accompanying claims and their equivalents are intended to cover such forms or modifications.

In embodiments, the kit includes a pharmaceutical formulation as described herein (including in an aspect, embodiment, claim, example, table, or figure). In embodiments, the kit includes an injectable formulation as described herein (including in an aspect, embodiment, claim, example, table, or figure). In embodiments, the kit includes a formulation as described herein (including in an aspect, embodiment, claim, example, table, or figure). In embodiments, the kit includes a composition (e.g., pharmaceutical composition, injectable composition) as described herein (including in an aspect, embodiment, claim, example, table, or figure).

Additional Embodiments

1. A formulation comprising: (a) a therapeutically or cosmetically effective amount of polidocanol; and (b) from about 0.5% W/V to about 10% W/V of an alcohol having 3 to 6 carbon atoms.

2. The formulation of embodiment 1, wherein the alcohol having 3 to 6 carbon atoms is propylene glycol.

3. The formulation of embodiment 1, wherein the alcohol having 3 to 6 carbon atoms is glycerine.

4. The formulation of one of embodiments 1 to 3, wherein the formulation does not contain ethanol or an ether.

5. The formulation of one of embodiments 1 to 4, wherein the formulation does not contain aliphatic polyethers.

6. The formulation of one of embodiments 1 to 5, wherein the formulation does not contain polyethylene glycol.

7. The formulation of one of embodiments 1 to 6, wherein the formulation does not contain poloxamers.

8. The formulation of one of embodiments 1 to 7, wherein the formulation is formulated for subcutaneous injection.

9. The formulation of one of embodiments 1 to 8, wherein the alcohol having 3 to 6 carbon atoms is present in an amount of from about 1% W/V to about 5% W/V.

10. The formulation of one of embodiments 1 to 8, wherein the alcohol having 3 to 6 carbon atoms is present in an amount of approximately 5% W/V.

11. The formulation of one of embodiments 1 to 10, provided that polidocanol is present in an amount that is greater than 1.0% W/V.

12. The formulation of one of embodiments 1 to 10, provided that polidocanol is present in an amount from about 0.1% W/V to about 20.0% W/V.

13. The formulation of one of embodiments 1 to 10, provided that polidocanol is present in an amount from about 0.5% W/V to about 10.0% W/V.

14. The formulation of one of embodiments 1 to 10, provided that polidocanol is present in an amount from about 0.5% W/V to about 2.0% W/V.

15. The formulation of one of embodiments 1 to 10, provided that polidocanol is present in an amount of 0.5% W/V, 1.25% W/V, or 2.0% W/V.

16. The formulation of one of embodiments 1 to 15, provided that the formulation has a pH of from about 6 to 9.

17. The formulation of one of embodiments 1 to 15, provided that the formulation has a pH of about 7 to 8.

18. The formulation of one of embodiments 1 to 17, wherein the subcutaneous injection is injection into the submental region of a human in need.

19. The formulation of one of embodiments 1 to 17, wherein the subcutaneous injection is injection into a fat pad.

20. The formulation of one of embodiments 1-19, wherein the polidocanol is a mixture of at least three C12 alkyl ethoxylate homologues with surfactant properties.

21. The formulation of embodiment 20, wherein said at least three C12 alkyl ethoxylate homologues have a hydrophilic lipid balance (HLB) from 10-15

22. The formulation of one of embodiments 20 or 21, wherein said at least three C12 alkyl ethoxylate homologues are 15% of said mixture.

23. The formulation of one of embodiments 1 to 22, wherein said polidocanol is present at a concentration greater than 0.1% and less than 1.5%.

24. The formulation of one of embodiments 1 to 23, wherein said formulation is an aqueous formulation.

25. The formulation of one of embodiments 1 to 24, wherein the volume is less than about 0.5 cc per injection.

26. A method for treating adipose tissue comprising administering to a human or animal subject by subcutaneous injection the formulation of one of embodiments 1 to 25.

27. A method for the reduction and/or prevention of subcutaneous adipose tissue comprising administering to a human or animal subject by subcutaneous injection the formulation of one of embodiments 1 to 25.

28. The method of one of embodiments 26 or 27, wherein the formulation comprises polidocanol in an amount of from about 0.5% W/V to 2.0% W/V and propylene glycol in an amount of from about 1% W/V to 5% W/V, wherein the formulation does not contain polyethylene glycol or poloxamers.

29. The method of one of embodiments 26-28, wherein said administration is performed no more than once every 28 days.

30. A kit for treating adipose tissue comprising the formulation of one of embodiments 1 to 25 and instructions for use.

31. The kit of embodiment 30, further comprising a needle for subcutaneous injection.

32. The kit of embodiment 30 or 31, further comprising a syringe for subcutaneous injection.

33. The kit of one of embodiments 30-32, wherein the formulation is provided in a container designed for dispensation to a syringe.

EXAMPLES

Example 1: Pre-Clinical Study—Effect of Polidocanol on the Inguinal-Lateral Fat Pad (ILFP) of Hamsters Concentration of polidocanol solutions: 0.5%, 1.25% and 2%; Deoxycholate dose concentration: 1.0%
Species: LVG Syrian Golden Hamsters, retired breeders
Body weight: 165-187 grams (on first day of treatment period); Sex: Male; Vendor: Charles River; Diet: Standard lab chow; Randomization: Animals were grouped so that the mean body weights are approximately equal among the treatment subgroups
Model: The inguinal fat pads were used as a model tissue. In the golden hamster, these subcutaneous fat pads lying bilaterally in the inguinal region were continuous with fat pads located laterally on each respective flank, and thus were referenced here as inguinal-lateral fat pads or ILFPs. The length of each fat pad offered the opportunity for two injections spaced approximately 4 cm apart within each fat pad, and similarly placed control injections in the contralateral fat pad of the same animal. The unilateral experimental treatment in this model offered the advantage of paired comparison of treated and non-treated fat pads within individual animals, and served as a model to assess lipolytic effects of test compounds.
Test Articles: Polidocanol: Solutions provided by Advantar (or other), 0.5%, 1.25%, and 2.0%, formulated with propylene glycol.
Treatment: Under isoflurane anesthesia, the right ILFP was injected with 0.2 cc of drug solution at two sites (medial and lateral portions of the ILFP), spaced 0.5 cm apart. The left ILFP was injected in medial and lateral sites with filtered vehicle control solution. A total of 36 animals were divided into three dose groups, outlined in the following table:

TABLE 1

Division of animals in treatment groups

| Grp. | Polidocanol/ Deoxycholate dose (concentration) | Treatment(s) | Route, Dosing Regimes | Sacrifice and harvest | n |
|---|---|---|---|---|---|
| 1 | 0.5% | Days 0, 28 | 0.2 ml, subcutaneously into inguinal fat pad, 3 injection 0.5 cm apart | Day 28 (n = 4), 56 (n = 5) | 9 |
| 2 | 1.25% | Days 0, 28 | 0.2 ml, subcutaneously into inguinal fat pad, 3 injection 0.5 cm apart | Day 28 (n = 4), 56 (n = 5) | 9 |
| 3 | 2.0% | Days 0, 28 | 0.2 ml, subcutaneously into inguinal fat pad, 3 injection 0.5 cm apart | Day 28 (n = 4), 56 (n = 5) | 9 |
| 4 | 1.0% (Deoxycholate) | Day 0 | 0.2 ml, subcutaneously into inguinal fat pad, 3 injection 0.5 cm apart | Day 28 | 5 |

Harvesting: On day 28 (injections at Day 0) and 56 (injections at Day 0 and Day 28), the animals were sacrificed and the ILFPs excised and weighed (see "INGUINAL/LATERAL FAT PAD HARVESTING PROCEDURE," below). Medial and lateral portions of each ILFP were weighed together. After weighing, each portion was frozen separately on dry ice and stored frozen for histological analysis.
Fat weight analysis: Results were expressed primarily as the mean difference between the right and left ILFPs in grams ($\Delta$ R-L) and as the percent difference ($\Delta$ R-L %). Statistical analysis was performed.
Histological analysis: The right (polidocanol treated) medial injection sites of all six subjects, and one left (saline treated) site from each treatment group (animals #3 and #5), were analyzed histologically to determine evidence of necrosis within the adipose tissue. The selected samples were sectioned at a thickness of 20 microns taken at intervals of 0.5 mm through the tissue. The sections were mounted and stained with H&E and examined microscopically for evidence of necrosis or inflammation. Representative images of each tissue were recorded with a Carl Zeiss color camera. Although necrosis or inflammation cannot be determined definitively by visual inspection of the H&E stained sections, infiltration of the tissue by foreign (non-adipose) cells is interpreted as an inflammatory response (which can be suggestive of a necrotic event).
Histopathology of normal adipose tissue is nearly devoid of inflammatory cell infiltration and shows very thin cell membranes surrounding lipid droplets with occasional strands of connective tissue separating different lobules of fat cells. Histopathology of adipose tissue treated with polidocanol shows dose dependent changes of fat cell necrosis and apoptosis leading to large vacuolar areas separated by thicker fibrotic septa and generalized fibrotic changes. In addition, there is a lymphomononuclear inflammatory infiltrate with macrophage phagocytosis of lipid cell debris.

Injection and Harvesting Procedures
Inguinal Injection Procedure (0.2 cc Volume, 0.5 cm Apart)
The animals were injected percutaneously with 0.2 mL/injection of test article solution at up to four (4) sites (in the medial, central, and lateral portions of the ILFP) running superiorly to caudally, spaced 0.5 cm apart. The injections were carried out by inserting the needle into the right inguinal region, locating the tip of the needle in the middle of the fat pad between the peritoneal wall and the right leg. In hamsters, the fat could be roughly visualized as a light area beneath the skin. The tip of the needle was at a depth adequate to enter the inguinal fat (as discerned by the thickness of tissue when the needle tip is raised slightly upward while in its final position) while avoiding the leg muscle and the peritoneum. The needle tip was placed approximately 0.5 cm medial to a line drawn from the patella of the knee to the xyphoid appendix of the sternum.

Inguinal-Lateral Fat Pad Harvesting Procedure (Hamster)

With the animal lying ventral side up, skin was cut along abdominal midline from the umbilicus to a point caudal to the penis near the bottom of the scrotum. The skin was cut from the penile area in a posterior and lateral direction toward the posterior of the hindlimb. From the superior end of the midline incision (near umbilicus), skin was cut bilaterally along the flank in a dorsal direction to the spinal region, forming triangular skin flaps over the abdomen. An elipse was harvested of skin overlying the region of the ILFP, and placed in formalin for storage and. Carefully reflected each skin flap away from the fat (remove fat attached to skin), using blunt dissection combined with incision of fascia as needed. The peritoneum and scrotal sac were exposed, as well as the inguinal area to beyond the knee and along the flanks. The inguinal fat pad was tan in color and lied primarily in the inguinal crease between the abdomen and hind leg diagonally medially from the tail to laterally toward the head. The fat pad was contiguous with a thin sheet of subcutaneous fat that wraps dorsally over the lateral side of the animal and medially across to the contralateral fat pad. The fat along the abdominal midline was cut, separating the right and left fat pads. The inguinal fat was dissected away from the peritoneum in the crease. Using blunt dissection underneath the pad, the pad was separated from underlying attached muscle from the ventral midline section to the inferio medial and dorsal lateral end of the pad avoiding removal of the thin areas that begin to fan out dorsal laterally over the side of the animal. The superior border was cut parallel along a line from the knee to the xiphoid process. Care was taken to harvest both the right and left fat pad according to the same anatomical boundaries so to avoid harvesting excess fat on one side versus the other. The treated side was more fibrotic and reduced in size over the vehicle side.

Example 2: Phase III Clinical Study

A multicenter, phase III, randomized, double-blind, placebo-controlled, parallel-group study can evaluate the efficacy and safety of polidocanol administered at fixed doses of 0.5% W/V and 1.0% W/V. The study is divided into a screening period (week −8 to baseline; visit 1), followed by a 12-week treatment period (visits 2-5) and a 12-week efficacy and safety follow-up period (visits 6 and 7). Polidocanol formulations will be formulated as shown in Table 2.

TABLE 2

Exemplary Polidocanol Formulation

| | Percent | Mass |
|---|---|---|
| Polidocanol | 0.5% to 1.0% | 5.0 to 10.0 g |
| Propylene Glycol or Glycerine | 1% to 5% | 10.00 g to 50.00 g |
| Disodium Hydrogen Phosphate | 0.24% | 2.4 g |
| Potassium Di-hydrogen Phosphate | 0.085% | 0.85 g |
| 0.1M NaOH for pH adjust to 7.2-7.5 | q.s. | q.s. |
| 0.1M HCl for pH adjust | q.s. | q.s. |
| Sterile water for injection | to 100% | 981.75 g to 936.75 g |

TABLE 3

Exemplary Polidocanol Formulation

| | Percent | Mass |
|---|---|---|
| Polidocanol | 1.0% to 3.0% | 10.0 to 30.0 g |
| Propylene Glycol or Glycerine | 0.5% to 10% | 5.00 g to 100.00 g |
| Disodium Hydrogen Phosphate | 0.24% | 2.4 g |
| Potassium Di-hydrogen Phosphate | 0.085% | 0.85 g |
| 0.1M NaOH for pH adjust to 7.2-7.5 | q.s. | q.s. |
| 0.1M HCl for pH adjust | q.s. | q.s. |
| Sterile water for injection | to 100% | 981.75 g to 866.75 g |

TABLE 4

Exemplary Polidocanol Formulation

| | Percent | Mass |
|---|---|---|
| Polidocanol | 3.0% to 5.0% | 30.0 to 50.0 g |
| Propylene Glycol or Glycerine | 0.5% to 10% | 5.00 g to 100.00 g |
| Disodium Hydrogen Phosphate | 0.24% | 2.4 g |
| Potassium Di-hydrogen Phosphate | 0.085% | 0.85 g |
| 0.1M NaOH for pH adjust to 7.2-7.5 | q.s. | q.s. |
| 0.1M HCl for pH adjust | q.s. | q.s. |
| Sterile water for injection | to 100% | 961.75 g to 846.75 g |

TABLE 5

Exemplary Polidocanol Formulation

| | Percent | Mass |
|---|---|---|
| Polidocanol | 5.0% to 10.0% | 50.0 to 100.0 g |
| Propylene Glycol or Glycerine | 0.5% to 10% | 5.00 g to 100.00 g |
| Disodium Hydrogen Phosphate | 0.24% | 2.4 g |
| Potassium Di-hydrogen Phosphate | 0.085% | 0.85 g |
| 0.1M NaOH for pH adjust to 7.2-7.5 | q.s. | q.s. |
| 0.1M HCl for pH adjust | q.s. | q.s. |
| Sterile water for injection | to 100% | 941.75 g to 796.75 g |

TABLE 6

Exemplary Polidocanol Formulation

| | Percent | Mass |
|---|---|---|
| Polidocanol | 0.25% to 1.25% | 2.5 to 12.5 g |
| Propylene Glycol or Glycerine | 2.5% to 5.0% | 25.0 g to 50.0 g |

TABLE 6-continued

Exemplary Polidocanol Formulation

| | Percent | Mass |
|---|---|---|
| Disodium Hydrogen Phosphate | 0.24% | 2.4 g |
| Potassium Di-hydrogen Phosphate | 0.085% | 0.85 g |
| 0.1M NaOH for pH adjust to 7.2-7.5 | q.s. | q.s. |
| 0.1M HCl for pH adjust | q.s. | q.s. |
| Sterile water for injection | to 100% | 969.25 g to 959.25 g |

In embodiments of the above formulations, glycerine is substituted for propylene glycol in whole or in part.

Inclusion and Exclusion Criteria

Men and women aged 18-65 years are eligible to participate if they present with moderate or severe sub-mental fat ("SMF") [grade 2 or 3 on the 5-point Clinician-Reported Sub-mental Fat Rating Scale (CR-SMFRS)] and express dissatisfaction with the appearance of their sub-mental area [Subject Self-Rating Scale (SSRS) score 0-3] at visit 2. Patients will agree to undergo clinical evaluations and laboratory tests and to maintain stable body weight, diet and exercise practices during the study. Women of reproductive age are required not to be pregnant or lactating and to practice birth control during the study. The principal exclusion criteria will be: previous intervention to treat SMF; anatomical features or previous trauma liable to interfere with SMF evaluation or result in an aesthetically unacceptable outcome after treatment; evidence of any cause of sub-mental enlargement other than SMF; and any medical condition likely to affect safety or efficacy assessments or the patient's ability to undergo study procedures or provide informed consent. Patients with a body mass index (BMI) >30 kg m$^{-2}$, those undergoing or considering a weight-reduction program, and patients with a history of sensitivity to any components of the study material or topical or local anaesthetics will also be excluded.

Randomization

Patients will be randomized (1:1:1) at visit 2, after completion of baseline evaluations, through allocation of a unique randomization number using a computerized web/voice-response system. Polidocanol and placebo treatment kits will have an identical appearance and carried a blinded label with a random kit number; these will be assigned to patients using the computerized system.

Interventions

All randomized patients will have at least one treatment session, with a maximum of four sessions, separated by 28±5 day intervals (visits 2-5). Patients will receive up to 10 mL of the study drug per treatment session, and the number of sessions will be dependent on the amount of remaining SMF and each patient's satisfaction with the appearance of their face and chin. Injections will be administered subcutaneously directly into the pre-platysma SMF at a volume of 0.2 mL per injection and spaced approximately 1 cm apart using a grid to provide even coverage. Topical anesthesia will be provided, if needed. Premature treatment discontinuation could occur owing to adverse events (AEs), early therapeutic success or at the patient's request. The treatment area will be evaluated 7±3 days after each treatment and concomitant medication use was reported. Patients will attend two follow-up visits (visits 6 and 7) 4 weeks (±5 days) and 12 weeks (±7 days) after the final treatment session.

Efficacy Outcome Measures

Efficacy endpoints will be evaluated at visit 7 (12 weeks after final treatment). There will be two co-primary efficacy endpoints: the proportion of treatment responders, i.e. with a reduction in SMF of ≥1 point on the 5-point CR-SMFRS relative to baseline, and the proportion of patients satisfied with their appearance in association with their face and chin (i.e. with a score of ≥4 on the 7-point SSRS rating scale). To confirm the primary endpoint results, sensitivity analyses will be conducted on the secondary parameters of change from baseline in CR-SMFRS and SSRS scores, and changes in caliper measurements of SMF thickness, by treatment session. The effect of treatment on skin laxity (Skin Laxity Rating Scale, SLRS) will also be evaluated, and patient-reported outcomes were assessed using the Patient-Reported Submental Fat Rating Scale (PR-SMFRS) and Patient-Reported Submental Fat Impact Scale (PR-SMFIS). Additional patient-reported instruments will also be used.

Safety Outcome Measures

AEs will be evaluated at each visit and approximately 7 days after each treatment session, and were characterized descriptively by the day on which they started and stopped, and by severity and intensity. Treatment-emergent AEs will be defined as those with onset or exacerbation after the first treatment dose. Changes from baseline in clinical laboratory parameters and other tests, and variations in vital signs, body temperature and body weight, will also be measured.

Statistical Methodology

Using 80% of the effect size observed in two previous placebo-controlled and a 10% dropout rate per treatment group with a Pearson chi-square test for two proportions (two-sided test with α=0.025), a conservatively rounded sample size of 120 patients per treatment group will be used to guarantee a power of 90%.

The efficacy analyses is based on the intention-to-treat population (all randomized patients who had at least one efficacy assessment at baseline), with missing values at visit 7 imputed using last observation carried forward. The null hypothesis for the treatment comparisons is that there was no difference between each dose of polidocanol and placebo for the two co-primary efficacy endpoints. Comparisons of the two polidocanol dose groups with placebo is made via odds ratios from binary logistic regression. An adjustment for multiplicity was performed. Because there were two co-primary endpoints, the null hypotheses for both variables had to be rejected at the same significance level (α=0.05). This is accounted for by using the larger of the two P-values in the Bonferroni-Holm procedure.

For the secondary endpoints, changes from baseline in CR-SMFRS and caliper scores are analyzed using a mixed-models repeated-measures analysis. Changes from baseline in SSRS scores are analyzed by an analysis of variance (ANOVA). PR-SMFRS improvements of ≥1 point are analyzed by binary logistic regression. Changes from baseline in SLRS scores are recorded in frequency tables and Pearson's chi-square test was applied to compare each polidocanol group with placebo. Descriptive statistics were calculated for PR-SMFIS scores, with the change from baseline analyzed by a post hoc Fisher's least-square difference test for continuous variables, only if ANOVA show an overall treatment effect. Statistical summaries for AEs are based on treatment-emergent AEs in the safety population (all patients who received at least one treatment with study drug). The numbers of AEs and patients presenting with each AE are categorized according to association with treatment, study withdrawal, death, severity, intensity, system organ class and preferred term.

The examples and embodiments described herein are for illustrative purposes only and various modifications or changes are included within the spirit and purview of this application and scope of the appended claims. All publications, patents, and patent applications cited herein are hereby incorporated by reference for all purposes.

What is claimed is:

1. A pharmaceutical formulation comprising:
   (i) polidocanol in an amount from about 0.5% W/V to about 2.0% W/V; and
   (ii) a $C_3$-$C_6$ alcohol in an amount from about 0.5% W/V to about 10% W/V.

2. The pharmaceutical formulation of claim 1, wherein said polidocanol is in an amount from about 0.5% W/V to about 1.25% W/V.

3. The pharmaceutical formulation of claim 1, wherein said $C_3$-$C_6$ alcohol is propylene glycol.

4. The pharmaceutical formulation of claim 1, wherein the pharmaceutical formulation is a subcutaneous injection formulation.

5. The pharmaceutical formulation of claim 1, wherein the pharmaceutical formulation is an aqueous formulation.

6. The pharmaceutical formulation of claim 1, wherein said $C_3$-$C_6$ alcohol is present in an amount from about 2.0% W/V to about 5.0% W/V.

7. The pharmaceutical formulation of claim 1 having an osmolality of less than about 400 milliosmoles/kg.

8. The pharmaceutical formulation of claim 1 having a pH of about 7 to about 8.

9. The pharmaceutical formulation of claim 1 having a volume from about 1.0 to about 2.0 cc.

* * * * *